United States Patent
Hara et al.

(10) Patent No.: US 12,364,159 B2
(45) Date of Patent: Jul. 15, 2025

(54) ORGANIC COMPOUND, LIGHT-EMITTING DEVICE, LIGHT-EMITTING APPARATUS, ELECTRONIC DEVICE, AND LIGHTING DEVICE

(71) Applicant: Semiconductor Energy Laboratory Co., Ltd., Kanagawa-ken (JP)

(72) Inventors: Tomoka Hara, Kanagawa (JP); Hideko Yoshizumi, Kanagawa (JP); Toshiki Sasaki, Kanagawa (JP); Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 844 days.

(21) Appl. No.: 17/601,797

(22) PCT Filed: Apr. 1, 2020

(86) PCT No.: PCT/IB2020/053072
§ 371 (c)(1),
(2) Date: Oct. 6, 2021

(87) PCT Pub. No.: WO2020/208475
PCT Pub. Date: Oct. 15, 2020

(65) Prior Publication Data
US 2022/0173327 A1 Jun. 2, 2022

(30) Foreign Application Priority Data

Apr. 12, 2019 (JP) ................... 2019-076333

(51) Int. Cl.
*H01L 51/00* (2006.01)
*C07D 491/048* (2006.01)
(Continued)

(52) U.S. Cl.
CPC ....... *H10K 85/657* (2023.02); *C07D 491/048* (2013.01); *C09K 11/06* (2013.01);
(Continued)

(58) Field of Classification Search
None
See application file for complete search history.

(56) References Cited

U.S. PATENT DOCUMENTS

| 6,602,618 B2 | 8/2003 | Watanabe et al. |
| 9,553,274 B2 | 1/2017 | Xia et al. |

(Continued)

FOREIGN PATENT DOCUMENTS

| CN | 104292241 A | 1/2015 |
| CN | 106661006 A | 5/2017 |

(Continued)

OTHER PUBLICATIONS

International Search Report (Application No. PCT/IB2020/053072) Dated Jun. 30, 2020.

(Continued)

*Primary Examiner* — Tae H Yoon
(74) *Attorney, Agent, or Firm* — Husch Blackwell LLP

(57) ABSTRACT

A benzofuropyrimidine derivative or a benzothienopyrimidine derivative, which is a novel organic compound, is provided. The organic compound is represented by General Formula (G1) below. In General Formula (G1), Q represents oxygen or sulfur. A represents any one of a substituted or unsubstituted condensed aromatic hydrocarbon ring having 6 to 13 carbon atoms in the ring and a substituted or unsubstituted π-electron rich condensed heteroaromatic ring having 6 to 13 carbon atoms in the ring; and R1 to R19 each independently represent any one of hydrogen, an alkyl group having 1 to 6 carbon atoms, a substituted or unsubstituted (Continued)

cycloalkyl group having 3 to 7 carbon atoms in the ring, and a substituted or unsubstituted aryl group having 6 to 13 carbon atoms in the ring.

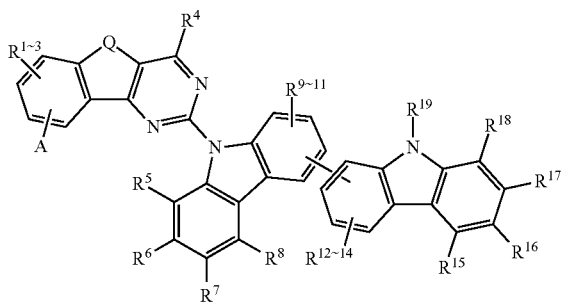

(G1)

10 Claims, 22 Drawing Sheets

(51) Int. Cl.
C09K 11/06 (2006.01)
H10K 85/60 (2023.01)
H10K 50/16 (2023.01)
H10K 101/30 (2023.01)

(52) U.S. Cl.
CPC ....... H10K 85/615 (2023.02); H10K 85/6572 (2023.02); H10K 85/6576 (2023.02); C09K 2211/1018 (2013.01); H10K 50/16 (2023.02); H10K 2101/30 (2023.02)

(56) References Cited

U.S. PATENT DOCUMENTS

| 10,868,258 | B2 | 12/2020 | Kurihara et al. |
| 2007/0159083 | A1 | 7/2007 | Matsuura et al. |
| 2008/0091012 | A1* | 4/2008 | Egawa ................ H10K 85/626 313/504 |
| 2010/0231568 | A1 | 9/2010 | Yamashita et al. |
| 2013/0140549 | A1 | 6/2013 | Xia et al. |
| 2014/0291645 | A1 | 10/2014 | Inoue et al. |
| 2015/0021555 | A1 | 1/2015 | Kwong et al. |
| 2015/0021556 | A1 | 1/2015 | Xia et al. |
| 2016/0093818 | A1 | 3/2016 | Inoue et al. |
| 2016/0336517 | A1 | 11/2016 | Hirose et al. |
| 2016/0351829 | A1 | 12/2016 | Hosoumi et al. |
| 2016/0351833 | A1 | 12/2016 | Hosoumi et al. |
| 2017/0069852 | A1 | 3/2017 | Kanamoto et al. |
| 2017/0170409 | A1 | 6/2017 | Xia et al. |
| 2017/0186971 | A1 | 6/2017 | Kanamoto et al. |
| 2017/0207399 | A1 | 7/2017 | Parham et al. |
| 2018/0182976 | A1 | 6/2018 | Kurihara et al. |
| 2020/0024282 | A1 | 1/2020 | Parham et al. |
| 2020/0028091 | A1 | 1/2020 | Parham et al. |
| 2021/0057667 | A1 | 2/2021 | Ohsawa et al. |
| 2021/0249619 | A1 | 8/2021 | Seo et al. |

FOREIGN PATENT DOCUMENTS

| CN | 109689658 A | 4/2019 |
| CN | 109790173 A | 5/2019 |
| EP | 2 826 781 A1 | 1/2015 |
| EP | 3 174 954 A | 6/2017 |
| EP | 3 519 415 A | 8/2019 |
| EP | 3 519 417 A | 8/2019 |
| JP | 2010-182699 A | 8/2010 |
| JP | 2011-084531 A | 4/2011 |
| JP | 2015-021007 A | 2/2015 |
| JP | 2017-524707 | 8/2017 |
| JP | 2019-532951 | 11/2019 |
| JP | 2019-532952 | 11/2019 |
| JP | 6918068 | 8/2021 |
| KR | 2015-0009462 A | 1/2015 |
| KR | 2015-0133998 A | 12/2015 |
| KR | 2016-0114526 A | 10/2016 |
| KR | 2017-0039209 A | 4/2017 |
| KR | 2018-0074582 A | 7/2018 |
| KR | 2019-0053948 A | 5/2019 |
| KR | 2019-0059949 A | 5/2019 |
| TW | 201343639 | 11/2013 |
| WO | WO 2013/102992 A1 | 7/2013 |
| WO | WO 2016/015810 A1 | 2/2016 |
| WO | WO 2016/153283 A1 | 9/2016 |
| WO | WO 2018/060218 A1 | 4/2018 |
| WO | WO 2018/060307 A1 | 4/2018 |
| WO | WO 2019/215535 A1 | 11/2019 |
| WO | WO-2020/075014 | 4/2020 |

OTHER PUBLICATIONS

Written Opinion (Application No. PCT/IB2020/053072) Dated Jun. 30, 2020.

* cited by examiner

ORGANIC COMPOUND, LIGHT-EMITTING DEVICE, LIGHT-EMITTING APPARATUS, ELECTRONIC DEVICE, AND LIGHTING DEVICE

This application is a 371 of international application PCT/IB2020/053072 filed on Apr. 1, 2020 which is incorporated herein by reference.

TECHNICAL FIELD

One embodiment of the present invention relates to an organic compound, a light-emitting device, a light-emitting apparatus, an electronic device, and a lighting device. Note that one embodiment of the present invention is not limited to the above technical field. That is, one embodiment of the present invention relates to an object, a method, a manufacturing method, or a driving method. Alternatively, one embodiment of the present invention relates to a process, a machine, manufacture, or a composition of matter. Specific examples include a semiconductor device, a display device, and a liquid crystal display device.

BACKGROUND ART

A light-emitting device including an EL layer between a pair of electrodes (also referred to as an organic EL device or a light-emitting element) has characteristics such as thinness, light weight, high-speed response to input signals, and low power consumption; thus, a display including such a light-emitting device has attracted attention as a next-generation flat panel display.

In a light-emitting device, voltage application between a pair of electrodes causes, in an EL layer, recombination of electrons and holes injected from the electrodes, which brings a light-emitting substance (an organic compound) contained in the EL layer into an excited state; light is emitted when the light-emitting substance returns to the ground state from the excited state. The excited state can be a singlet excited state (S*) and a triplet excited state (T*): light emission from a singlet excited state is referred to as fluorescence, and light emission from a triplet excited state is referred to as phosphorescence. The statistical generation ratio thereof in the light-emitting device is considered to be S*:T*=1:3. Since the emission spectrum obtained from a light-emitting substance depends on the light-emitting substance, the use of different types of organic compounds as light-emitting substances offers light-emitting devices exhibiting various emission colors.

In order to improve device characteristics of such a light-emitting device, improvement of a device structure, development of a material, and the like have been actively carried out (see Patent Document 1, for example).

REFERENCE

Patent Document

[Patent Document 1] Japanese Published Patent Application No. 2010-182699

SUMMARY OF THE INVENTION

Problems to be Solved by the Invention

Thus, in one embodiment of the present invention, a novel organic compound is provided. In another embodiment of the present invention, a benzofuropyrimidine derivative or a benzothienopyrimidine derivative, which is a novel organic compound, is provided. In another embodiment of the present invention, a novel organic compound that can be used in a light-emitting device is provided. In another embodiment of the present invention, a novel organic compound that can be used in an EL layer of a light-emitting device is provided. In addition, a highly reliable and novel light-emitting device using a novel organic compound of one embodiment of the present invention is provided. In addition, a novel light-emitting apparatus, a novel electronic device, or a novel lighting device is provided. Note that the description of these objects does not preclude the existence of other objects. In one embodiment of the present invention, there is no need to achieve all of these objects. Objects other than these are apparent from the description of the specification, the drawings, the claims, and the like, and objects other than these can be derived from the description of the specification, the drawings, the claims, and the like.

Means for Solving the Problems

One embodiment of the present invention is a benzofuropyrimidine derivative or a benzothienopyrimidine derivative, which is an organic compound represented by General Formula (G1) below. The organic compound has a structure in which, as shown in General Formula (G1) below, a nitrogen atom of a first carbazole skeleton is bonded to the 2-position of a benzofuropyrimidine skeleton or a benzothienopyrimidine skeleton, and a second carbazole skeleton is bonded to a benzene ring of the first carbazole skeleton.

[Chemical Formula 1]

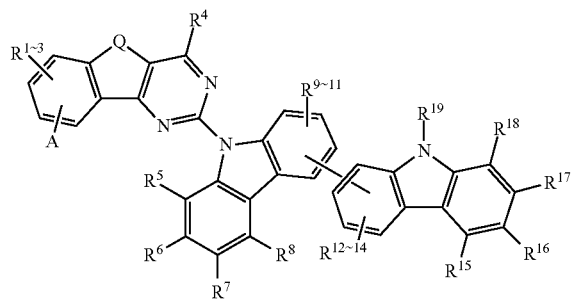

(G1)

In General Formula (G1) above, Q represents oxygen or sulfur. A represents any one of a substituted or unsubstituted condensed aromatic hydrocarbon ring having 6 to 13 carbon atoms in the ring and a substituted or unsubstituted π-electron rich condensed heteroaromatic ring having 6 to 13 carbon atoms in the ring; and $R^1$ to $R^{19}$ each independently represent any one of hydrogen, an alkyl group having 1 to 6 carbon atoms, a substituted or unsubstituted cycloalkyl group having 3 to 7 carbon atoms in the ring, and a substituted or unsubstituted aryl group having 6 to 13 carbon atoms in the ring.

Another embodiment of the present invention is a benzofuropyrimidine derivative or a benzothienopyrimidine derivative, which is an organic compound represented by General Formula (G2) below. The organic compound has a structure in which, as shown in General Formula (G2) below, a nitrogen atom of a first carbazole skeleton is bonded to the 2-position of a benzofuropyrimidine skeleton or a benzothienopyrimidine skeleton, a second carbazole skeleton is bonded to a benzene ring of the first carbazole skeleton, and any one of a condensed aromatic hydrocarbon ring and a π-electron rich condensed heteroaromatic ring, which is represented as A in the formula, is bonded to the 8-position of the benzofuropyrimidine skeleton or the benzothienopyrimidine skeleton.

[Chemical Formula 2]

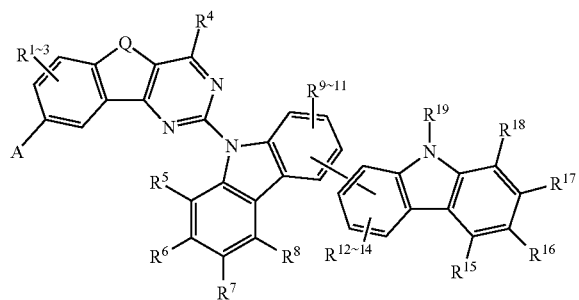

(G2)

In General Formula (G2) above, Q represents oxygen or sulfur. A represents any one of a substituted or unsubstituted condensed aromatic hydrocarbon ring having 6 to 13 carbon atoms in the ring and a substituted or unsubstituted π-electron rich condensed heteroaromatic ring having 6 to 13 carbon atoms in the ring; and $R^1$ to $R^{19}$ each independently represent any one of hydrogen, an alkyl group having 1 to 6 carbon atoms, a substituted or unsubstituted cycloalkyl group having 3 to 7 carbon atoms in the ring, and a substituted or unsubstituted aryl group having 6 to 13 carbon atoms in the ring.

Another embodiment of the present invention is a benzofuropyrimidine derivative or a benzothienopyrimidine derivative, which is an organic compound represented by General Formula (G3) below. The organic compound has a structure in which, as shown in General Formula (G3) below, a nitrogen atom of a first carbazole skeleton is bonded to the 2-position of a benzofuropyrimidine skeleton or a benzothienopyrimidine skeleton, a second carbazole skeleton is bonded to a benzene ring of the first carbazole skeleton, and a naphthalene skeleton is bonded to the 8-position of the benzofuropyrimidine skeleton or the benzothienopyrimidine skeleton.

[Chemical Formula 3]

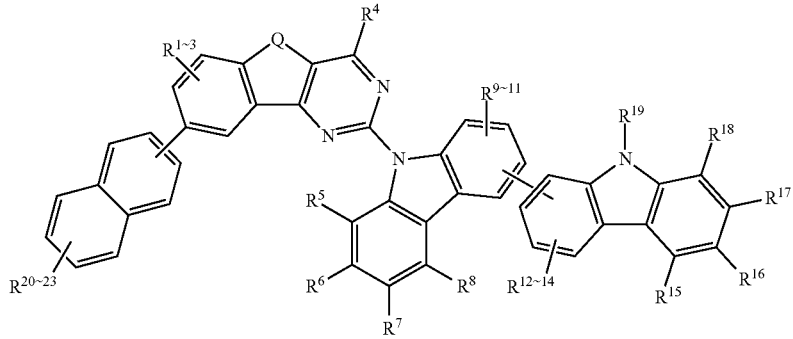

(G3)

In General Formula (G3) above, Q represents oxygen or sulfur. $R^1$ to $R^{23}$ each independently represent any one of hydrogen, an alkyl group having 1 to 6 carbon atoms, a substituted or unsubstituted cycloalkyl group having 3 to 7 carbon atoms in the ring, and a substituted or unsubstituted aryl group having 6 to 13 carbon atoms in the ring.

Another embodiment of the present invention is a benzofuropyrimidine derivative or a benzothienopyrimidine derivative, which is an organic compound represented by General Formula (G4) below. The organic compound has a structure in which, as shown in General Formula (G4) below, a nitrogen atom of a first carbazole skeleton is bonded to the 2-position of a benzofuropyrimidine skeleton or a benzothienopyrimidine skeleton, a second carbazole skeleton is bonded to a benzene ring of the first carbazole skeleton, and a dibenzothiophene skeleton is bonded to the 8-position of the benzofuropyrimidine skeleton or the benzothienopyrimidine skeleton.

[Chemical Formula 4]

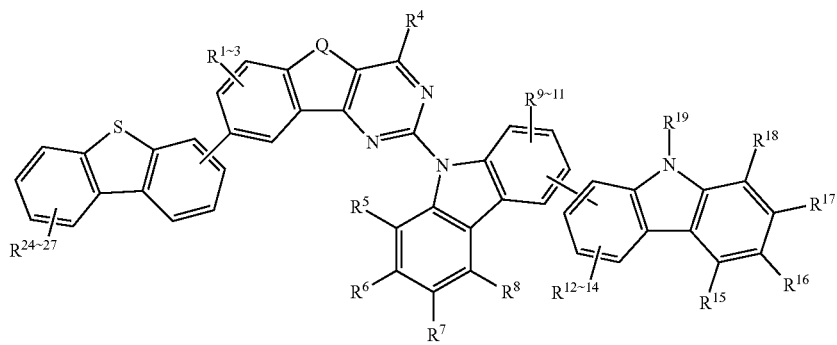

(G4)

In General Formula (G4) above, Q represents oxygen or sulfur. $R^1$ to $R^{19}$ and $R^{24}$ to $R^{27}$ each independently represent any one of hydrogen, an alkyl group having 1 to 6 carbon atoms, a substituted or unsubstituted cycloalkyl group having 3 to 7 carbon atoms in the ring, and a substituted or unsubstituted aryl group having 6 to 13 carbon atoms in the ring.

Another embodiment of the present invention is an organic compound represented by any one of Structural Formulae (100) and (101) below.

[Chemical Formula 5]

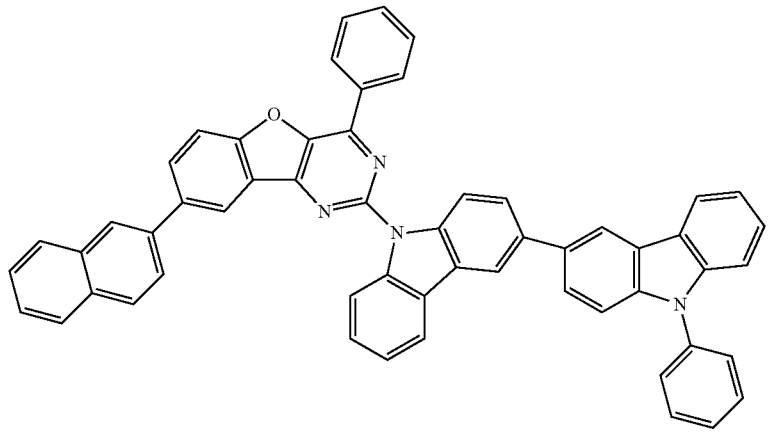

(100)

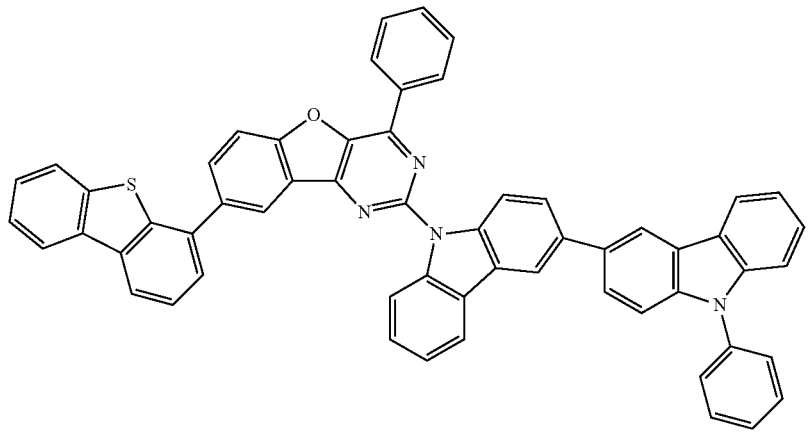

(101)

Another embodiment of the present invention is a light-emitting device using the above-described organic compound of one embodiment of the present invention. The present invention also includes a light-emitting device including a guest material in addition to the above-described organic compound. The present invention also includes a light-emitting device including a phosphorescent material in addition to the above-described organic compound.

Note that the present invention also includes a light-emitting device that is formed using the organic compound of one embodiment of the present invention for an EL layer between a pair of electrodes or a light-emitting layer included in the EL layer. In addition to the above-described light-emitting elements, the present invention includes a light-emitting device including a layer (e.g., a cap layer) that is in contact with an electrode and contains an organic compound. In addition to the light-emitting devices, a light-emitting apparatus including a transistor, a substrate, and the like is also included in the scope of the invention. Furthermore, in addition to the light-emitting apparatus, an electronic device and a lighting device that include a microphone, a camera, an operation button, an external connection portion, a housing, a cover, a support, a speaker, or the like are also included in the scope of the invention.

In addition, the scope of one embodiment of the present invention includes a light-emitting apparatus including a light-emitting device, and a lighting device including the light-emitting apparatus. Accordingly, the light-emitting apparatus in this specification refers to an image display device or a light source (including a lighting device). In addition, a light-emitting apparatus includes a module in which a light-emitting apparatus is connected to a connector such as an FPC (Flexible printed circuit) or a TCP (Tape Carrier Package), a module in which a printed wiring board is provided on the tip of a TCP, or a module in which an IC (integrated circuit) is directly mounted on a light-emitting device by a COG (Chip On Glass) method.

Effect of the Invention

In one embodiment of the present invention, a novel organic compound can be provided. In another embodiment of the present invention, a benzofuropyrimidine derivative or a benzothienopyrimidine derivative that is a novel organic compound can be provided. In one embodiment of the present invention, a novel organic compound that can be used in a light-emitting device can be provided. In one embodiment of the present invention, a novel organic compound that can be used in an EL layer of a light-emitting device can be provided. In addition, a highly reliable and novel light-emitting device can be provided by using a novel organic compound of one embodiment of the present invention. In addition, a novel light-emitting apparatus, a novel electronic device, or a novel lighting device can be provided.

MODE FOR CARRYING OUT THE INVENTION

Figure 1A:
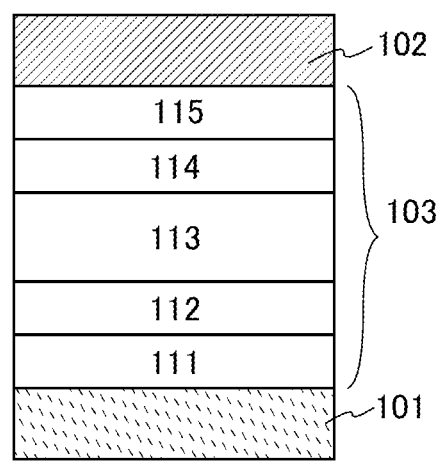
FIG. 1A is a diagram illustrating a structure of a light-emitting device.

Embodiments of the present invention will be described in detail below with reference to drawings. Note that the present invention is not limited to the following description, and the modes and details of the present invention can be modified in various ways without departing from the spirit and scope of the present invention. Thus, the present invention should not be construed as being limited to the descriptions in the following embodiments.

Note that the position, size, range, or the like of each component shown in drawings and the like is not accurately represented in some cases for easy understanding. Therefore, the disclosed invention is not necessarily limited to the position, size, range, or the like disclosed in drawings and the like.

In describing structures of the invention in this specification and the like with reference to drawings, common numerals are used for the same components in different drawings.

Embodiment 1

In this embodiment, organic compounds of embodiments of the present invention will be described. Note that an organic compound of one embodiment of the present invention is a benzofuropyrimidine derivative or a benzothienopyrimidine derivative represented by General Formula (G1) below. Note that the organic compound of one embodiment of the present invention has a structure in which, as shown in General Formula (G1) below, a nitrogen atom of a first carbazole skeleton is bonded to the 2-position of a benzofuropyrimidine skeleton or a benzothienopyrimidine skeleton, and a second carbazole skeleton is bonded to a benzene ring of the first carbazole skeleton.

13 carbon atoms in the ring; and $R^1$ to $R^{19}$ each independently represent any one of hydrogen, an alkyl group having 1 to 6 carbon atoms, a substituted or unsubstituted cycloalkyl group having 3 to 7 carbon atoms in the ring, and a substituted or unsubstituted aryl group having 6 to 13 carbon atoms in the ring.

The organic compound represented by General Formula (G1) above can have a low LUMO because of having a structure in which a nitrogen atom of a first carbazole skeleton is directly bonded to the 2-position of a benzofuropyrimidine skeleton or a benzothienopyrimidine skeleton. This is effective in improving the electron injection and transport properties in any of functional layers in an EL layer. The organic compound represented by General Formula (G1) above, which has a condensed ring as the substituent A, has improved chemical and physical stability and hardly interacts with a peripheral molecule, thereby maintaining a stable structure. When the condensed ring as the substituent A is positioned away from a pyrimidine ring, the T1 level can be easily adjusted. This facilitates the design of a host material based on the T1 level of a phosphorescent material (a guest material); the host material having an appropriate T1 level effectively improves the efficiency and reliability of an element.

Another embodiment of the present invention is a benzofuropyrimidine derivative or a benzothienopyrimidine derivative, which is an organic compound represented by General Formula (G2) below. The organic compound represented by General Formula (G2) below has a structure in which a nitrogen atom of a first carbazole skeleton is bonded to the 2-position of a benzofuropyrimidine skeleton or a benzothienopyrimidine skeleton, a second carbazole skeleton is bonded to a benzene ring of the first carbazole skeleton, and any one of a condensed aromatic hydrocarbon ring and a π-electron rich condensed heteroaromatic ring, which is represented as A in the formula, is bonded to the 8-position of the benzofuropyrimidine skeleton or the benzothienopyrimidine skeleton.

[Chemical Formula 6]

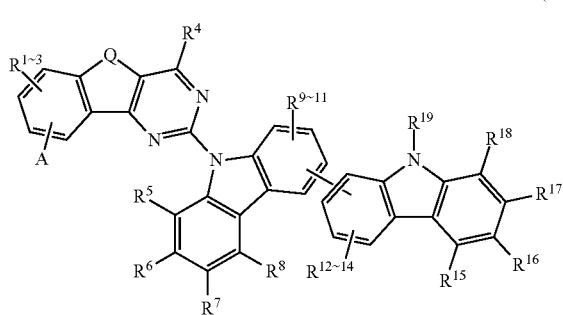

(G1)

[Chemical Formula 7]

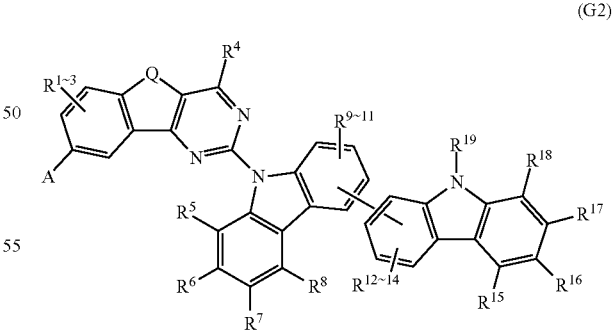

(G2)

Note that in General Formula (G1), Q represents oxygen or sulfur. A represents any one of a substituted or unsubstituted condensed aromatic hydrocarbon ring having 6 to 13 carbon atoms in the ring and a substituted or unsubstituted π-electron rich condensed heteroaromatic ring having 6 to In General Formula (G2) above, Q represents oxygen or sulfur. A represents any one of a substituted or unsubstituted condensed aromatic hydrocarbon ring having 6 to 13 carbon atoms in the ring and a substituted or unsubstituted π-electron rich condensed heteroaromatic ring having 6 to 13 carbon atoms in the ring; and $R^1$ to $R^{19}$ each independently represent any one of hydrogen, an alkyl group having 1 to 6 carbon atoms, a substituted or unsubstituted cycloalkyl group having 3 to 7 carbon atoms in the ring, and a substituted or unsubstituted aryl group having 6 to 13 carbon atoms in the ring.

The organic compound represented by General Formula (G2) above can have a low LUMO because of having a structure in which a nitrogen atom of a first carbazole skeleton is directly bonded to the 2-position of a benzofuropyrimidine skeleton or a benzothienopyrimidine skeleton. This is effective in improving the electron injection and transport properties in any of functional layers in an EL layer. The organic compound represented by General Formula (G2) above, which has a condensed ring as the substituent A, has improved chemical and physical stability and hardly interacts with a peripheral molecule, thereby maintaining a stable structure. When the condensed ring as the substituent A is positioned away from a pyrimidine ring, the T1 level can be easily adjusted. This facilitates the design of a host material based on the T1 level of a phosphorescent material (a guest material); the host material having an appropriate T1 level effectively improves the efficiency and reliability of an element. The condensed ring as the substituent A is preferably bonded to the 8-position of the benzofuropyrimidine skeleton or the benzothienopyrimidine skeleton, in which case the T1 level can be adjusted while the HOMO level and the LUMO level are maintained.

Another embodiment of the present invention is an organic compound represented by General Formula (G3) below. The organic compound represented by General Formula (G3) below has a structure in which a nitrogen atom of a first carbazole skeleton is bonded to the 2-position of a benzofuropyrimidine skeleton or a benzothienopyrimidine skeleton, a second carbazole skeleton is bonded to a benzene ring of the first carbazole skeleton, and a naphthalene skeleton is bonded to the 8-position of the benzofuropyrimidine skeleton or the benzothienopyrimidine skeleton.

In General Formula (G3) above, Q represents oxygen or sulfur. $R^1$ to $R^{23}$ each independently represent any one of hydrogen, an alkyl group having 1 to 6 carbon atoms, a substituted or unsubstituted cycloalkyl group having 3 to 7 carbon atoms in the ring, and a substituted or unsubstituted aryl group having 6 to 13 carbon atoms in the ring.

The organic compound represented by General Formula (G3) above can have a low LUMO because of having a structure in which a nitrogen atom of a first carbazole skeleton is directly bonded to the 2-position of a benzofuropyrimidine skeleton or a benzothienopyrimidine skeleton. This is effective in improving the electron injection and transport properties in any of functional layers in an EL layer. The organic compound, which has a structure in which a naphthalene skeleton is bonded to the 8-position of the benzofuropyrimidine skeleton or the benzothienopyrimidine skeleton, hardly interacts with a peripheral molecule, thereby maintaining a stable structure.

Another embodiment of the present invention is a benzofuropyrimidine derivative or a benzothienopyrimidine derivative, which is an organic compound represented by General Formula (G4) below. The organic compound represented by General Formula (G4) below has a structure in which a nitrogen atom of a first carbazole skeleton is bonded to the 2-position of a benzofuropyrimidine skeleton or a benzothienopyrimidine skeleton, a second carbazole skeleton is bonded to a benzene ring of the first carbazole skeleton, and a dibenzothiophene skeleton is bonded to the 8-position of the benzofuropyrimidine skeleton or the benzothienopyrimidine skeleton.

[Chemical Formula 8]

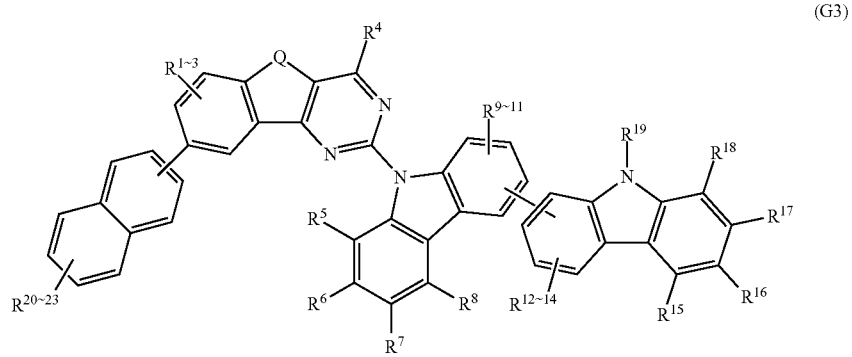

(G3)

[Chemical Formula 9]

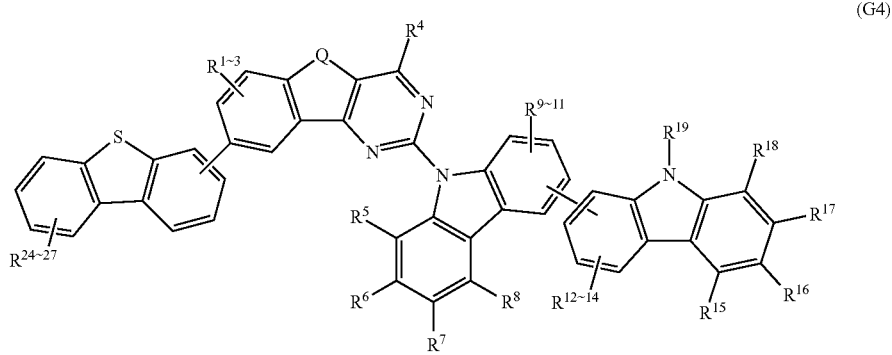

(G4)

In General Formula (G4) above, Q represents oxygen or sulfur. $R^1$ to $R^{19}$ and $R^{24}$ to $R^{27}$ each independently represent any one of hydrogen, an alkyl group having 1 to 6 carbon atoms, a substituted or unsubstituted cycloalkyl group having 3 to 7 carbon atoms in the ring, and a substituted or unsubstituted aryl group having 6 to 13 carbon atoms in the ring.

The organic compound represented by General Formula (G4) above can have a low LUMO because of having a structure in which a nitrogen atom of a first carbazole skeleton is directly bonded to the 2-position of a benzofuropyrimidine skeleton or a benzothienopyrimidine skeleton. This is effective in improving the electron injection and transport properties in any of functional layers in an EL layer. The organic compound, which has a structure in which a dibenzothiophene skeleton is bonded to the 8-position of the benzofuropyrimidine skeleton or the benzothienopyrimidine skeleton, hardly interacts with a peripheral molecule, thereby maintaining a stable structure.

Note that in the case where the substituted or unsubstituted condensed aromatic hydrocarbon ring having 6 to 13 carbon atoms in the ring or the substituted or unsubstituted π-electron rich condensed heteroaromatic ring having 6 to 13 carbon atoms in the ring in General Formulae (G1) and (G2) above has a substituent, examples of the substituent include an alkyl group having 1 to 6 carbon atoms, an alkoxy group having 1 to 6 carbon atoms, a monocyclic saturated hydrocarbon group having 5 to 7 carbon atoms, a polycyclic saturated hydrocarbon group having 7 to 10 carbon atoms, and a cyano group. More specifically, a methyl group, an ethyl group, a propyl group, an isopropyl group, a butyl group, an isobutyl group, a sec-butyl group, a tert-butyl group, a pentyl group, a methoxy group, an ethoxy group, a propoxy group, a cyclopentyl group, a cyclohexyl group, a cycloheptyl group, a 8,9,10-trinorbornanyl group, an adamantyl group, and the like are given.

In the case where the substituted or unsubstituted cycloalkyl group having 3 to 7 carbon atoms in the ring or the substituted or unsubstituted aryl group having 6 to 13 carbon atoms in the ring, which is $R^1$ to $R^{19}$ in General Formulae (G1) and (G2) above, $R^1$ to $R^{23}$ in General Formula (G3) above, or $R^1$ to $R^{19}$ and $R^{24}$ to $R^{27}$ in General Formula (G4) above, has a substituent, examples of the substituent include an alkyl group having 1 to 6 carbon atoms, an alkoxy group having 1 to 6 carbon atoms, a monocyclic saturated hydrocarbon group having 5 to 7 carbon atoms, a polycyclic saturated hydrocarbon group having 7 to 10 carbon atoms, and a cyano group. More specifically, a methyl group, an ethyl group, a propyl group, an isopropyl group, a butyl group, an isobutyl group, a sec-butyl group, a tert-butyl group, a pentyl group, a methoxy group, an ethoxy group, a propoxy group, a cyclopentyl group, a cyclohexyl group, a cycloheptyl group, a 8,9,10-trinorbornanyl group, an adamantyl group, and the like are given.

In the case where any one of $R^1$ to $R^{19}$ in General Formulae (G1) and (G2) above, $R^1$ to $R^{23}$ in General Formula (G3) above, and $R^1$ to $R^{19}$ and $R^{24}$ to $R^{27}$ in General Formula (G4) above represents an alkyl group having 1 to 6 carbon atoms, specific examples thereof include a methyl group, an ethyl group, a propyl group, an isopropyl group, a butyl group, a sec-butyl group, an isobutyl group, a tert-butyl group, a pentyl group, an isopentyl group, a sec-pentyl group, a tert-pentyl group, a neopentyl group, a hexyl group, an isohexyl group, a 3-methylpentyl group, a 2-methylpentyl group, a 2-ethylbutyl group, a 1,2-dimethylbutyl group, and a 2,3-dimethylbutyl group.

In the case where any one of $R^1$ to $R^{19}$ in General Formulae (G1) and (G2) above, $R^1$ to $R^{23}$ in General Formula (G3) above, and $R^1$ to $R^{19}$ and $R^{24}$ to $R^{27}$ in General Formula (G4) above represents a cycloalkyl group having 3 to 7 carbon atoms in the ring, specific examples thereof include a cyclopropyl group, a cyclobutyl group, a cyclopentyl group, a cyclohexyl group, a 1-methylcyclohexyl group, and a cycloheptyl group.

In the case where any one of $R^1$ to $R^{19}$ in General Formulae (G1) and (G2) above, $R^1$ to $R^{23}$ in General Formula (G3) above, and $R^1$ to $R^{19}$ and $R^{24}$ to $R^{27}$ in General Formula (G4) above represents an aryl group having 6 to 13 carbon atoms, specific examples thereof include a phenyl group, an o-tolyl group, a m-tolyl group, a p-tolyl group, a mesityl group, an o-biphenyl group, a m-biphenyl group, a p-biphenyl group, a 1-naphthyl group, a 2-naphthyl group, and a fluorenyl group.

Next, specific structural formulae of the above-described organic compound of one embodiment of the present invention are shown below. Note that the present invention is not limited to these formulae.

[Chemical Formula 10]
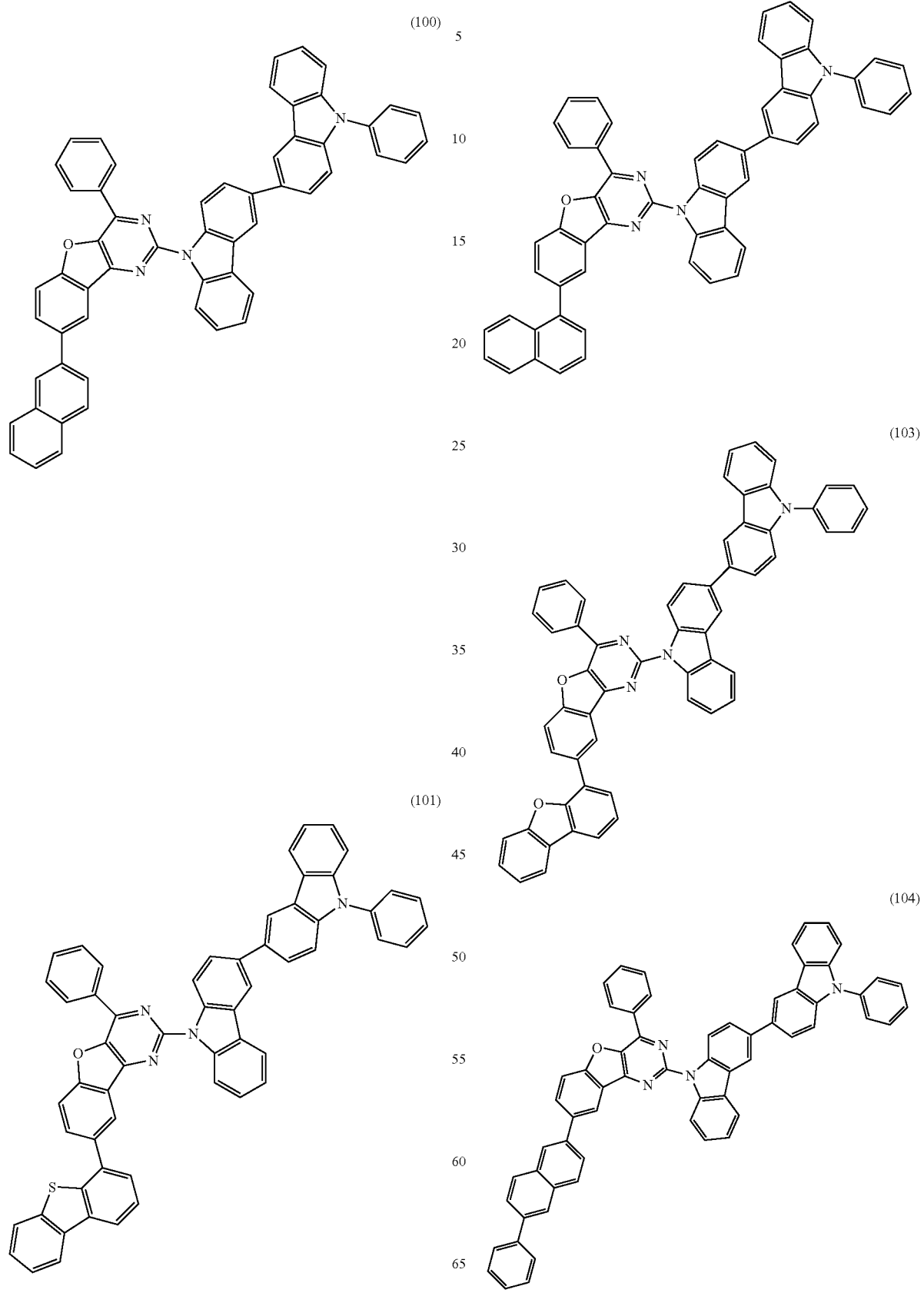

(105)
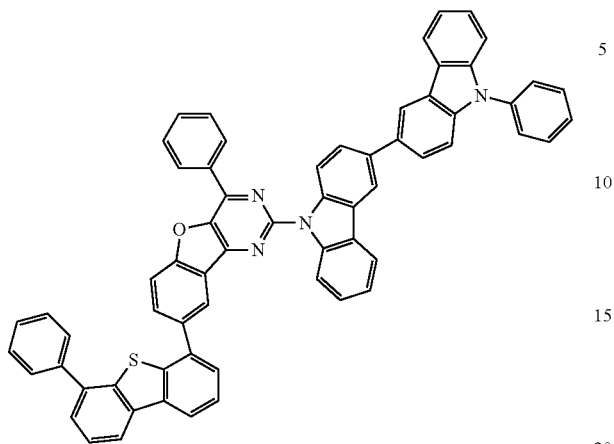
(106)
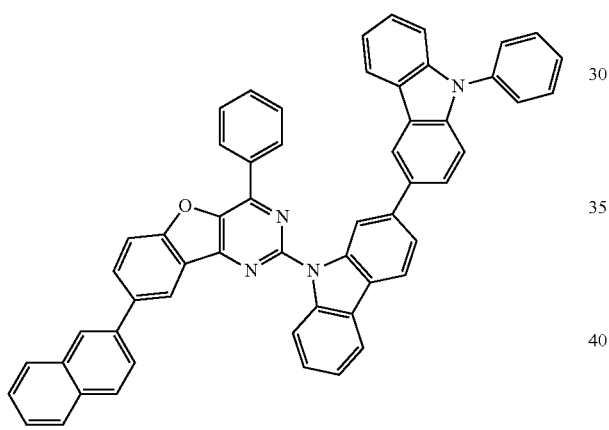
(107)
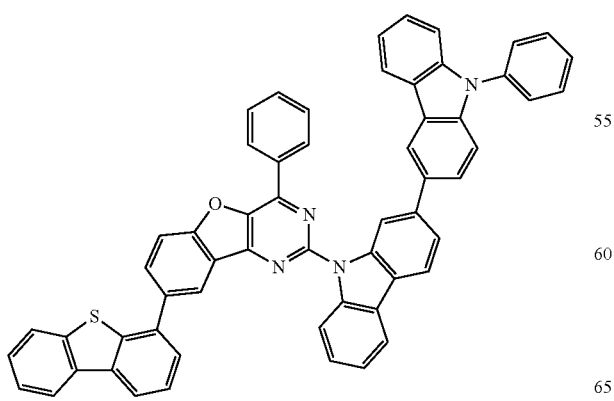
(108)
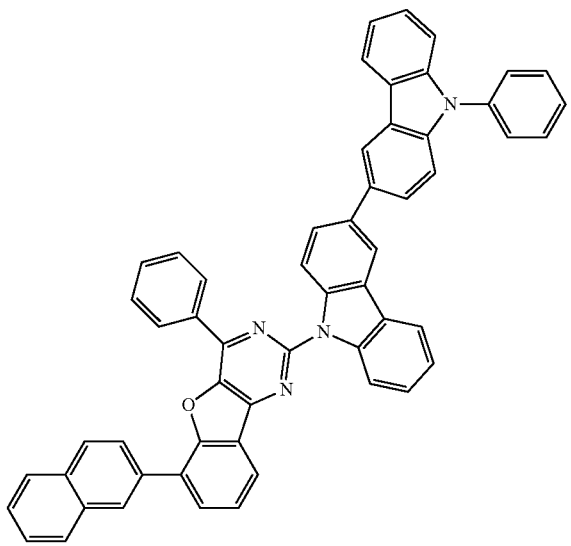
[Chemical Formula 11]
(109)
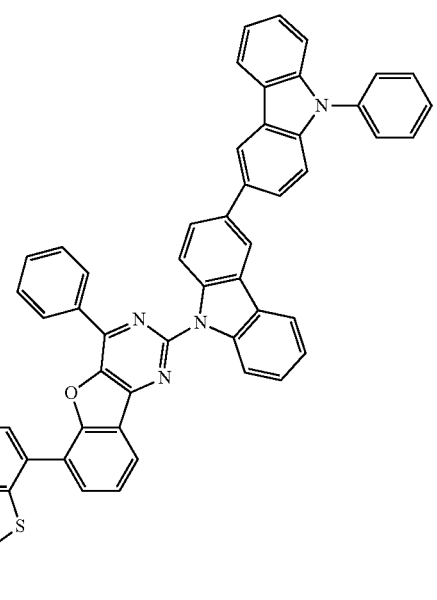

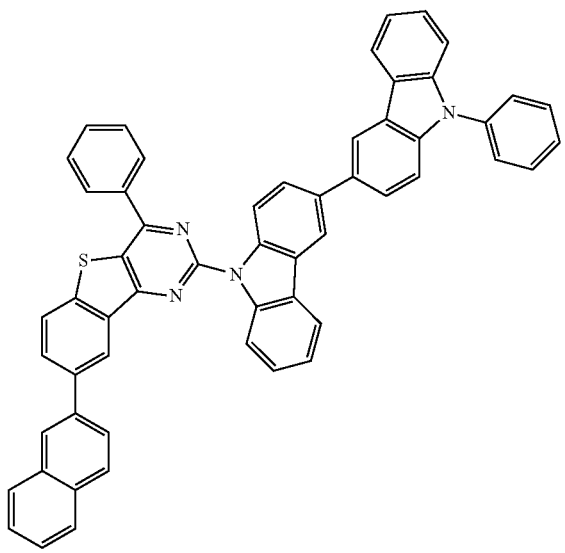

(110)

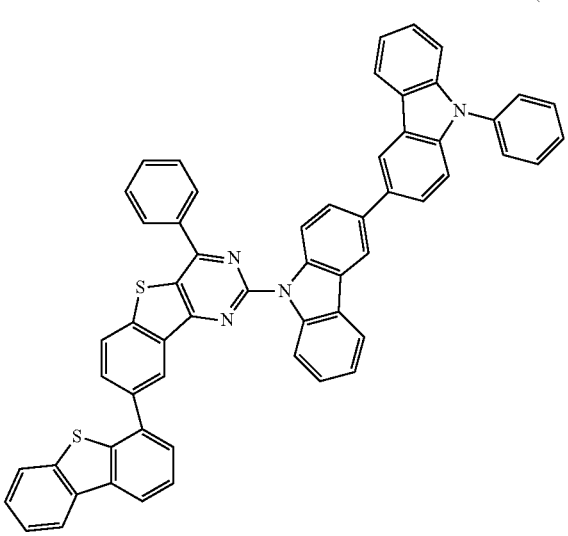

(111)

Note that the organic compounds represented by Structural Formulae (100) to (111) above are examples of the organic compound represented by General Formula (G1) above, but the organic compound of one embodiment of the present invention is not limited thereto.

Next, a synthesis method of a benzofuropyrimidine derivative or a benzothienopyrimidine derivative, which is one embodiment of the present invention and represented by General Formula (G1) below, will be described.

[Chemical Formula 12]

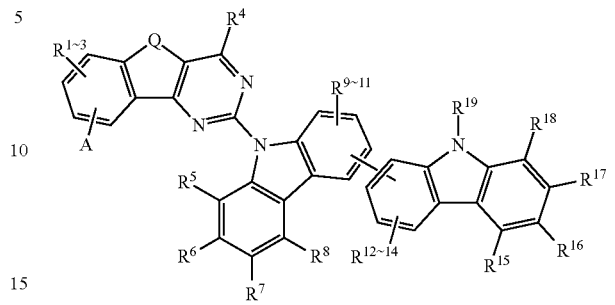

(G1)

In General Formula (G1), Q represents oxygen or sulfur. A represents any one of a substituted or unsubstituted condensed aromatic hydrocarbon ring having 6 to 13 carbon atoms in the ring and a substituted or unsubstituted π-electron rich condensed heteroaromatic ring having 6 to 13 carbon atoms in the ring; and $R^1$ to $R^{19}$ each independently represent any one of hydrogen, an alkyl group having 1 to 6 carbon atoms, a substituted or unsubstituted cycloalkyl group having 3 to 7 carbon atoms in the ring, and a substituted or unsubstituted aryl group having 6 to 13 carbon atoms in the ring.

<<Method for Synthesizing Organic Compound Represented by General Formula (G1)>>

An example of the synthesis method of a benzofuropyrimidine derivative or a benzothienopyrimidine derivative, which is represented by General Formula (G1), will be described below. A variety of reactions can be used for the synthesis of these organic compounds. For example, as shown in Synthesis Scheme (A), an intermediate (A3), which is obtained by the reaction of a trihalogen compound (A1) having a benzofuropyrimidine skeleton or a benzothienopyrimidine skeleton and a boronic acid compound (A2) as $R^4$, is reacted with a bicarbazole compound (A4), so that an intermediate (A5) is formed; then, the intermediate (A5) is reacted with a boronic acid compound (A6) as A, whereby the organic compound represented by General Formula (G1) can be obtained.

[Chemical Formula 13]

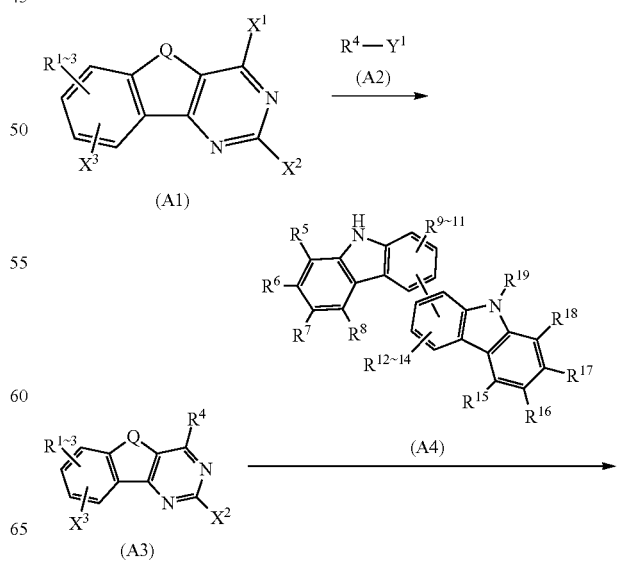

-continued

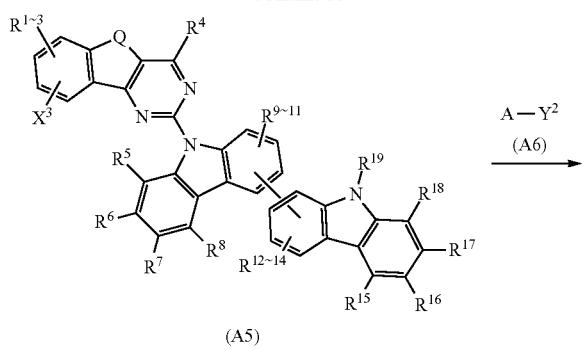

(A5)

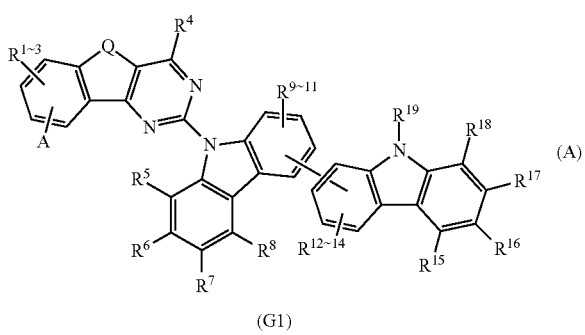

(G1)

Alternatively, the organic compound represented by General Formula (G1) may be obtained in the following manner: as shown in Synthesis Scheme (B) below, a dihalogen compound (B1) having a benzofuropyrimidine skeleton or a benzothienopyrimidine skeleton, to which A is bonded, is reacted with the boronic acid compound (A2) as $R^4$, so that an intermediate (B2) is formed; then, the intermediate (B2) is reacted with the bicarbazole compound (A4).

[Chemical Formula 14]

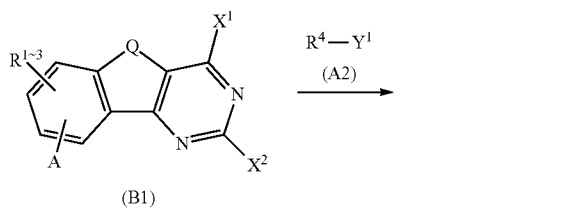

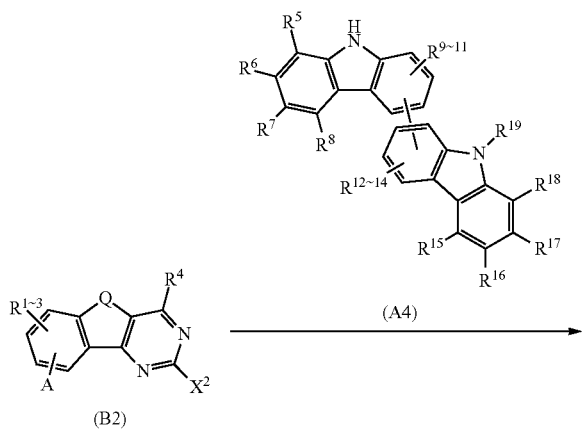

-continued

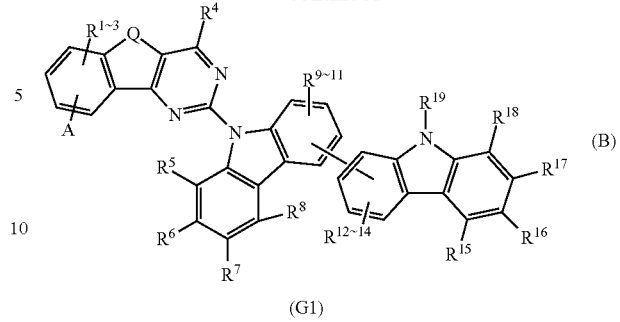

(B)

Note that in Synthesis Schemes (A) and (B) above, Q represents oxygen or sulfur. A represents any one of a substituted or unsubstituted condensed aromatic hydrocarbon ring having 6 to 13 carbon atoms in the ring and a substituted or unsubstituted π-electron rich condensed heteroaromatic ring having 6 to 13 carbon atoms in the ring; and $R^1$ to $R^{19}$ each independently represent any one of hydrogen, an alkyl group having 1 to 6 carbon atoms, a substituted or unsubstituted cycloalkyl group having 3 to 7 carbon atoms in the ring, and a substituted or unsubstituted aryl group having 6 to 13 carbon atoms in the ring. Furthermore, $X^1$ to $X^3$ represent a halogen element, which is preferably chlorine, bromine, or iodine. $Y^1$ and $Y^2$ represent a boronic acid, a boronic ester, a cyclic-triolborate salt, or the like. As the cyclic-triolborate salt, a lithium salt, a potassium salt, or a sodium salt may be used.

In Synthesis Schemes (A) and (B) above, various kinds of compounds (A1), (A2), (A3), (A4), (A6), (B1), and (B2) are commercially available or can be synthesized, which makes it possible to synthesize many kinds of the organic compound represented by General Formula (G1). Thus, the organic EL material of the present invention is characterized by having numerous variations.

Examples of the synthesis method of the organic compound of one embodiment of the present invention are described above; however, the present invention is not limited thereto and the organic compound may be synthesized by any other synthesis method.

The structures described in this embodiment can be used in an appropriate combination with the structures described in the other embodiments.

Embodiment 2

In this embodiment, light-emitting devices of embodiments of the present invention will be described.

<Structure Example of Light-Emitting Device>

FIG. 1A shows an example of a light-emitting device including, between a pair of electrodes, an EL layer including a light-emitting layer. Specifically, the light-emitting device has a structure in which an EL layer 103 is provided between a first electrode 101 and a second electrode 102. For example, in the case where the first electrode 101 is an anode, the EL layer 103 has a structure in which a hole-injection layer 111, a hole-transport layer 112, a light-emitting layer 113, an electron-transport layer 114, and an electron-injection layer 115 are stacked as functional layers in this order.

Figure 1B:
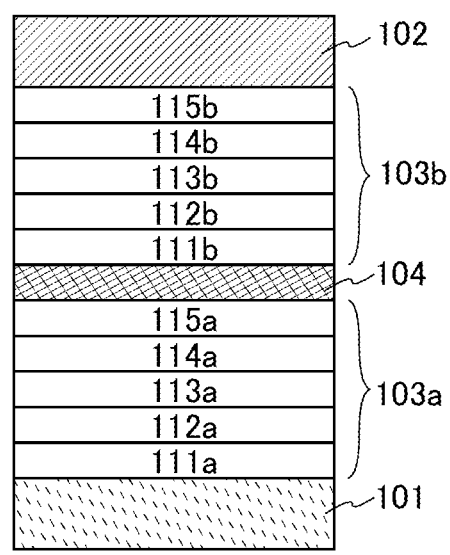
FIG. 1B is a diagram illustrating a structure of a light-emitting device.

Embodiments of the present invention also include light-emitting devices having other structures, such as a light-emitting device that can be driven at low voltage by having a structure (a tandem structure) in which between a pair of electrodes, a plurality of EL layers are provided with a charge-generation layer therebetween as shown in FIG. 1B, and a light-emitting device having a micro-optical resonator (microcavity) structure between a pair of electrodes and thus having improved optical characteristics. The charge-generation layer has a function of injecting electrons into one of the adjacent EL layers and injecting holes into the other of the EL layers when a voltage is applied between the first electrode 101 and the second electrode 102.

Note that at least one of the first electrode 101 and the second electrode 102 of the light-emitting device is a light-transmitting electrode (e.g., a transparent electrode or a transflective electrode). In the case where the light-transmitting electrode is a transparent electrode, the transparent electrode has a visible light transmittance higher than or equal to 40%. In the case where the light-transmitting electrode is a transflective electrode having both a transmitting property and a reflective property, the transflective electrode has a visible light reflectance higher than or equal to 20% and lower than or equal to 80%, preferably higher than or equal to 40% and lower than or equal to 70%. These electrodes preferably have a resistivity of $1\times10^{-2}$ Ωcm or less.

When one of the first electrode 101 and the second electrode 102 is an electrode having a reflective property (a reflective electrode) in the above-described light-emitting device of one embodiment of the present invention, the visible light reflectance of the electrode having a reflective property is higher than or equal to 40% and lower than or equal to 100%, preferably higher than or equal to 70% and lower than or equal to 100%. This electrode preferably has a resistivity of $1\times10^{-2}$ Ωcm or less.

The above-described tandem structure includes a plurality of EL layers between which a charge-generation layer is formed; the plurality of EL layers each include a light-emitting layer; and emission colors of the light-emitting layers can be combined freely. For example, the emission color of a first light-emitting layer included in a first EL layer stacked over the first electrode 101 can be any of red, green, yellow, and blue; the emission color of a second light-emitting layer included in a second EL layer stacked over the first EL layer with a charge-generation layer therebetween can be any of red, green, yellow, and blue; and the emission color of a third light-emitting layer included in a third EL layer stacked over the second EL layer with a charge-generation layer therebetween can be any of red, green, yellow, and blue.

The above-described micro-optical resonator (microcavity) structure can be obtained when a reflective electrode is formed as the first electrode 101 of the light-emitting device and a transflective electrode is formed as the second electrode 102, for example. In other words, when the first electrode 101 of the light-emitting device is a reflective electrode having a stacked structure of a reflective conductive material and a light-transmitting conductive material (a transparent conductive film), optical adjustment can be performed by adjusting the thickness of the transparent conductive film. Specifically, when the wavelength of light obtained from the light-emitting layer 113 is λ, the distance between the first electrode 101 and the second electrode 102 is preferably adjusted to be in the neighborhood of mλ/2 (m is a natural number). Thus, light emitted by the EL layer 103 can be intensified.

To amplify desired light (wavelength: λ) obtained from the light-emitting layer 113, the optical path length from the first electrode 101 to a region where the desired light is obtained in the light-emitting layer 113 (a light-emitting region) and the optical path length from the second electrode 102 to the region where the desired light is obtained in the light-emitting layer 113 (a light-emitting region) are preferably adjusted to be in the neighborhood of (2m'+1)λ/4 (m' is a natural number). Here, the light-emitting region means a region where holes and electrons are recombined in the light-emitting layer 113.

By performing such optical adjustment, the spectrum of specific monochromatic light obtained from the light-emitting layer 113 can be narrowed and light emission with high color purity can be obtained.

Note that in the above case, the optical path length between the first electrode 101 and the second electrode 102 is, to be exact, the total thickness from a reflective region in the first electrode 101 to a reflective region in the second electrode 102. However, it is difficult to precisely determine the reflective regions in the first electrode 101 and the second electrode 102; thus, it is assumed that the above effect can be sufficiently obtained wherever the reflective regions may be set in the first electrode 101 and the second electrode 102. Furthermore, the optical path length between the first electrode 101 and the light-emitting layer that emits the desired light is, to be exact, the optical path length between the reflective region in the first electrode 101 and the light-emitting region in the light-emitting layer that emits the desired light. However, it is difficult to precisely determine the reflective region in the first electrode 101 and the light-emitting region in the light-emitting layer that emits the desired light; thus, it is assumed that the above effect can be sufficiently obtained wherever the reflective region and the light-emitting region may be set in the first electrode 101 and the light-emitting layer that emits the desired light, respectively.

In the case where the light-emitting device has a microcavity structure as described above, even when an EL layer is shared, light (monochromatic light) with different wavelengths can be extracted by changing the optical path length between electrodes. Thus, side-by-side patterning to obtain different emission colors (e.g., RGB) is not needed, leading to higher resolution. Furthermore, a combination with coloring layers (color filters) is also possible. Moreover, the emission intensity of light with a specific wavelength in the front direction can be increased, so that power consumption can be reduced.

<First Electrode and Second Electrode>

As materials for forming the first electrode 101 and the second electrode 102, any of the following materials can be used in an appropriate combination as long as the functions of the electrodes described above can be fulfilled. For example, a metal, an alloy, an electrically conductive compound, and a mixture of these can be used as appropriate. Specific examples include In—Sn oxide (also referred to as ITO), In—Si—Sn oxide (also referred to as ITSO), In—Zn oxide, and In—W—Zn oxide. It is also possible to use a metal such as aluminum (Al), titanium (Ti), chromium (Cr), manganese (Mn), iron (Fe), cobalt (Co), nickel (Ni), copper (Cu), gallium (Ga), zinc (Zn), indium (In), tin (Sn), molybdenum (Mo), tantalum (Ta), tungsten (W), palladium (Pd), gold (Au), platinum (Pt), silver (Ag), yttrium (Y), or neodymium (Nd) or an alloy containing an appropriate combination of any of these metals. It is also possible to use an element belonging to Group 1 or Group 2 in the periodic table, which is not listed above as an example (e.g., lithium (Li), cesium (Cs), calcium (Ca), or strontium (Sr)), a rare earth metal such as europium (Eu) or ytterbium (Yb), an alloy containing an appropriate combination of any of these elements, graphene, or the like.

For fabrication of these electrodes, a sputtering method or a vacuum evaporation method can be used.

<Hole-Injection Layer>

The hole-injection layer 111 injects holes from the first electrode 101 that is an anode and a charge-generation layer 104 to EL layers (103, 103a, and 103b) and contains an organic acceptor material (an electron-accept material).

For the hole-injection layer 111, an organic acceptor material (an electron-accept material) and a hole-transport material can be used. In that case, the organic acceptor material exhibits an electron-accepting property with respect to the hole-transport material. Specifically, transition metal oxides such as molybdenum oxide, vanadium oxide, ruthenium oxide, tungsten oxide, and manganese oxide can be given. It is also possible to use a phthalocyanine-based compound such as phthalocyanine (abbreviation: $H_2Pc$) or copper phthalocyanine (abbreviation: CuPc), a low-molecular compound, a high-molecular compound, or the like. As the hole-transport material, a material having a deep HOMO level, specifically, a substance with a relatively deep HOMO level higher than or equal to −5.7 eV and lower than or equal to −5.4 eV is preferable. The hole-transport material with such a relatively deep HOMO level facilitates hole injection into the hole-transport layer 112.

As the organic acceptor material, an organic compound having an electron-withdrawing group (particularly a cyano group or a halogen group such as a fluoro group) can be used, for example. The hole-injection layer 111 may be formed of such an organic acceptor material alone or in combination with a hole-transport material.

Examples of the organic compound having an electron-withdrawing group include 7,7,8,8-tetracyano-2,3,5,6-tetrafluoroquinodimethane (abbreviation: $F_4$-TCNQ), chloranil, 2,3,6,7,10,11-hexacyano-1,4,5,8,9,12-hexaazatriphenylene (abbreviation: HAT-CN), 1,3,4,5,7,8-hexafluorotetracyano-naphthoquinodimethane (abbreviation: F6-TCNNQ), and 2-(7-dicyanomethylene-1,3,4,5,6,8,9,10-octafluoro-7H-pyren-2-ylidene)malononitrile. A compound in which electron-withdrawing groups are bonded to a condensed aromatic ring having a plurality of heteroatoms, such as HAT-CN, is particularly preferable because it is thermally stable. A [3]radialene derivative having an electron-withdrawing group (in particular, a cyano group or a halogen group such as a fluoro group) is preferable because of having a very high electron-accepting property. Specific examples include α,α',α"-1,2,3-cyclopropanetriylidenetris[4-cyano-2,3,5,6-tetrafluorobenzeneacetonitrile], α,α',α"-1,2,3-cyclopropanetriylidenetris[2,6-dichloro-3,5-difluoro-4-(trifluoromethyl)benzeneacetonitrile], and α,α',α"-1,2,3-cyclopropanetriylidenetris[2,3,4,5,6-pentafluorobenzeneacetonitrile].

As the hole-transport material, a known material can be used; particularly in the case of using a hole-transport material with a deep HOMO level, the hole-transport material preferably has any of a carbazole skeleton, a dibenzofuran skeleton, a dibenzothiophene skeleton, and an anthracene skeleton. In particular, an aromatic amine having a substituent that includes a dibenzofuran ring or a dibenzothiophene ring, an aromatic monoamine that includes a naphthalene ring, or an aromatic monoamine in which a 9-fluorenyl group is bonded to nitrogen of amine through an arylene group may be used.

As the hole-transport material (including the hole-transport material with a deep HOMO level), it is preferable to use a substance having a hole mobility higher than or equal to $1 \times 10^{-6}$ cm$^2$/Vs in the case where the square root of the electric field strength [V/cm] is 600. Note that other substances can also be used as long as they have a property of transporting more holes than electrons. Note that the materials preferably have an N,N-bis(4-biphenyl)amino group, in which case a light-emitting device with a long lifetime can be fabricated.

Specific examples of the hole-transport material include N-(4-biphenyl)-6,N-diphenylbenzo[b]naphtho[1,2-d]furan-8-amine (abbreviation: BnfABP), N,N-bis(4-biphenyl)-6-phenylbenzo[b]naphtho[1,2-d]furan-8-amine (abbreviation: BBABnf), 4,4'-bis(6-phenylbenzo[b]naphtho[1,2-d]furan-8-yl)-4"-phenyltriphenylamine (abbreviation: BnfBB1BP), N,N-bis(4-biphenyl)benzo[b]naphtho[1,2-d]furan-6-amine (abbreviation: BBABnf(6)), N,N-bis(4-biphenyl)benzo[b]naphtho[1,2-d]furan-8-amine (abbreviation: BBABnf(8)), N,N-bis(4-biphenyl)benzo[b]naphtho[2,3-d]furan-4-amine (abbreviation: BBABnf(II)(4)), N,N-bis[4-(dibenzofuran-4-yl)phenyl]-4-amino-p-terphenyl (abbreviation: DBfBB1TP), N-[4-(dibenzothiophen-4-yl)phenyl]-N-phenyl-4-biphenylamine (abbreviation: ThBA1BP), 4-(2-naphthyl)-4',4"-diphenyltriphenylamine (abbreviation: BBAβNB), 4-[4-(2-naphthyl)phenyl]-4',4"-diphenyltriphenylamine (abbreviation: BBAβNBi), 4,4'-diphenyl-4"-(6;1'-binaphthyl-2-yl)triphenylamine (abbreviation: BBAαNβNB), 4,4'-diphenyl-4"-(7;1'-binaphthyl-2-yl)triphenylamine (abbreviation: BBAαNβNB-03), 4,4'-diphenyl-4"-(7-phenyl)naphthyl-2-yl)triphenylamine (abbreviation: BBAPβNB-03), 4,4'-diphenyl-4"-(6;2'-binaphthyl-2-yl)triphenylamine (abbreviation: BBA(βN2)B), 4,4'-diphenyl-4"-(7;2'-binaphthyl-2-yl)triphenylamine (abbreviation: BBA(βN2)B-03), 4,4'-diphenyl-4"-(4;2'-binaphthyl-1-yl)triphenylamine (abbreviation: BBAβNαNB), 4,4'-diphenyl-4"-(5;2'-binaphthyl-1-yl)triphenylamine (abbreviation: BBAβNαNB-02), 4-(4-biphenylyl)-4'-(2-naphthyl)-4"-phenyltriphenylamine (abbreviation: TPBiAβNB), 4-(3-biphenylyl)-4'-[4-(2-naphthyl)phenyl]-4"-phenyltriphenylamine (abbreviation: mTPBiAβNBi), 4-(4-biphenylyl)-4'-[4-(2-naphthyl)phenyl]-4"-phenyltriphenylamine (abbreviation: TPBiAβNBi), 4-phenyl-4'-(1-naphthyl)triphenylamine (abbreviation: αNBA1BP), 4,4'-bis(1-naphthyl)triphenylamine (abbreviation: αNBB1BP), 4,4'-diphenyl-4"-[4'-(carbazol-9-yl)biphenyl-4-yl]triphenylamine (abbreviation: YGTBi1BP), 4'-[4-(3-phenyl-9H-carbazol-9-yl)phenyl]tris(1,1'-biphenyl-4-yl)amine (abbreviation: YGTBi1BP-02), 4-[4'-(carbazol-9-yl)biphenyl-4-yl]-4'-(2-naphthyl)-4"-phenyltriphenylamine (abbreviation: YGTBiβNB), N-[4-(9-phenyl-9H-carbazol-3-yl)phenyl]-N-[4-(1-naphthyl)phenyl]-9,9'-spirobi(9H-fluoren)-2-amine (abbreviation: PCBNBSF), N,N-bis(4-biphenylyl)-9,9'-spirobi[9H-fluoren]-2-amine (abbreviation: BBASF), N,N-bis(1,1'-biphenyl-4-yl)-9,9'-spirobi[9H-fluoren]-4-amine (abbreviation: BBASF(4)), N-(1,1'-biphenyl-2-yl)-N-(9,9-dimethyl-9H-fluoren-2-yl)-9,9'-spirobi(9H-fluoren)-4-amine (abbreviation: oFBiSF), N-(4-biphenyl)-N-(9,9-dimethyl-9H-fluoren-2-yl)dibenzofuran-4-amine (abbreviation: FrBiF), N-[4-(1-naphthyl)phenyl]-N-[3-(6-phenyldibenzofuran-4-yl)phenyl]-1-naphthylamine (abbreviation: mPDBfBNBN), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), 4-phenyl-4'-[4-(9-phenylfluoren-9-yl)phenyl]triphenylamine (abbreviation: BPAFLBi), 4-phenyl-4'-(9-phenyl-9H-carbazol-3-yl)triphenylamine (abbreviation: PCBA1BP), 4,4'-diphenyl-4"-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4"-(9-phenyl-9H-carbazol-3-yl)triphenylamine (abbreviation: PCBNBB), N-phenyl-N-[4-(9-phenyl-9H-carbazol-3-yl)phenyl]spiro-9,9'-bifluoren-2-amine (abbreviation: PCBASF), and N-(1,1'-biphenyl-4-yl)-9,9-dimethyl-N-[4-(9-phenyl-9H-carbazol-3-yl)phenyl]-9H-fluoren-2-amine (abbreviation: PCBBiF).

Note that the hole-injection layer 111 can be formed by any of various known deposition methods, and can be formed by a vacuum evaporation method, for example.

<Hole-Transport Layer>

The hole-transport layer 112 transports holes, which are injected from the first electrode 101 by the hole-injection layer 111, to the light-emitting layer 113.

For the hole-transport layer 112, a known hole-transport material as well as the above-described hole-transport material can be used. The hole-transport layer 112 may have a stacked-layer structure. Note that in the case where the hole-transport layer 112 has a stacked-layer structure, a layer on the light-emitting layer side may have a function of an electron-blocking layer.

When the HOMO level of the hole-transport material used in the hole-injection layer 111 and the HOMO level of the hole-transport material used in the hole-transport layer 112 are compared to each other, the materials are preferably selected so that the HOMO level of the hole-transport material used in the hole-transport layer 112 is deeper than the HOMO level of the hole-transport material used in the hole-injection layer 111 and the difference in HOMO level is less than or equal to 0.2 eV. It is further preferable that these hole-transport materials be the same material, in which case holes can be injected smoothly.

In the case where the hole-transport layer 112 has a stacked-layer structure, when the HOMO level of the hole-transport material used in the hole-transport layer formed on the hole-injection layer 111 side and the HOMO level of the hole-transport material used in the hole-transport layer formed on the light-emitting layer 113 side are compared to each other, the latter HOMO level is preferably deeper than the former HOMO level. Furthermore, the materials are preferably selected so that the difference in HOMO level is less than or equal to 0.2 eV. Owing to the above-described relation between the HOMO levels of the hole-transport materials used in the hole-injection layer 111 and the hole-transport layer 112 having a stacked-layer structure, holes are injected into each layer smoothly, which prevents an increase in driving voltage and deficiency of holes in the light-emitting layer 113.

Preferably, the hole-transport materials used in the hole-injection layer 111 and the hole-transport layer 112 each have a hole-transport skeleton. The hole-transport skeleton is preferably a carbazole skeleton, a dibenzofuran skeleton, a dibenzothiophene skeleton, and an anthracene skeleton, with which the HOMO levels of these hole-transport materials do not become too shallow. The hole-transport materials used for the adjacent layers in the hole-injection layer 111 and the hole-transport layer 112 having a stacked-layer structure preferably have the same hole-transport skeleton, in which case holes can be injected smoothly. In particular, the hole-transport skeleton for these layers is preferably a dibenzofuran skeleton.

The hole-transport materials used for the adjacent layers in the hole-injection layer 111 and the hole-transport layer 112 having a stacked-layer structure are preferably the same, in which case holes can be injected more smoothly into the adjacent layer in the cathode direction.

<Light-Emitting Layer>

In the light-emitting device of one embodiment of the present invention, the light-emitting layer 113 may have a single-layer structure or a stacked-layer structure of a plurality of light-emitting layers. In the case where a plurality of light-emitting layers are stacked, the light-emitting layers are preferably formed to have functions different from each other.

The light-emitting layer 113 includes a light-emitting substance (a guest material) and a host material in which the light-emitting substance is dispersed.

Note that as the light-emitting substance (the guest material), a substance exhibiting fluorescence (a fluorescent substance), a substance exhibiting phosphorescence (a phosphorescent substance), a thermally activated delayed fluorescent (TADF) material exhibiting thermally activated delayed fluorescence, other light-emitting substances, or the like can be used. As the organic compound (the host material), various carrier-transport materials such as the TADF material as well as an electron-transport material and a hole-transport material can be used. As a specific example of a hole-transport material, an electron-transport material, and the like, one or more kinds of the materials described in this specification and known materials can be used as appropriate.

Examples of the fluorescent substance that can be used as the guest material in the light-emitting layer 113 are as follows. Fluorescent substances other than those given below can also be used.

Examples include 5,6-bis[4-(10-phenyl-9-anthryl)phenyl]-2,2'-bipyridine (abbreviation: PAP2BPy), 5,6-bis[4'-(10-phenyl-9-anthryl)biphenyl-4-yl]-2,2'-bipyridine (abbreviation: PAPP2BPy), N,N-diphenyl-N,N-bis[4-(9-phenyl-9H-fluoren-9-yl)phenyl]pyrene-1,6-diamine (abbreviation: 1,6FLPAPrn), N,N-bis(3-methylphenyl)-N,N-bis[3-(9-phenyl-9H-fluoren-9-yl)phenyl]pyrene-1,6-diamine (abbreviation: 1,6mMemFLPAPrn), N,N-bis[4-(9H-carbazol-9-yl)phenyl]-N,N-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), perylene, 2,5,8,11-tetra(tert-butyl)perylene (abbreviation: TBP), 4-(10-phenyl-9-anthryl)-4'-(9-phenyl-9H-carbazol-3-yl)triphenylamine (abbreviation: PCBAPA), N,N'-(2-tert-butylanthracene-9,10-diyldi-4,1-phenylene)bis[N,N',N'-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N',N'-triphenyl-1,4-phenylenediamine (abbreviation: 2DPAPPA), N,N,N',N',N'',N'',N''',N'''-octaphenyldibenzo[g,p]rysene-2,7,10,15-tetraamine (abbreviation: DBC1), coumarin 30, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N,N-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), 9,10-bis(1,1'-biphenyl-2-yl)-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), coumarin 545T, N,N'-diphenylquinacridone, (abbreviation: DPQd), rubrene, 5,12-bis(1,1'-biphenyl-4-yl)-6,11-diphenyltetracene (abbreviation: BPT), 2-(2-{2-[4-(dimethylamino)phenyl]ethenyl}-6-methyl-4H-pyran-4-ylidene)propanedinitrile (abbreviation: DCM1), 2-{2-methyl-6-[2-(2,3,6,7-tetrahydro-1H,5H-benzo[i]quinolizin- 9-yl)ethenyl]-4H-pyran-4-ylidene}propanedinitrile (abbreviation: DCM2), N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-a]fluoranthene-3,10-diamine (abbreviation: p-mPhAFD), 2-{2-isopropyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTI), 2-{2-tert-butyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTB), 2-(2,6-bis{2-[4-(dimethylamino)phenyl]ethenyl}-4H-pyran-4-ylidene)propanedinitrile (abbreviation: BisDCM), 2-{2,6-bis[2-(8-methoxy-1,1,7,7-tetramethyl-2,3,6,7-tetrahydro-1H,5H-benzo[ij]quinolizin-9-yl)ethenyl]-4H-pyran-4-ylidene}propanedinitrile (abbreviation: BisDCJTM), N,N-diphenyl-N,N-(1,6-pyrene-diyl)bis[(6-phenylbenzo[b]naphtho[1,2-d]furan)-8-amine] (abbreviation: 1,6BnfAPrn-03), 3,10-bis[N-(9-phenyl-9H-carbazol-2-yl)-N-phenylamino]naphtho[2,3-b;6,7-b']bisbenzofuran (abbreviation: 3,10PCA2Nbf(IV)-02), and 3,10-bis[N-(dibenzofuran-3-yl)-N-phenylamino]naphtho[2,3-b;6,7-b']bisbenzofuran (abbreviation: 3,10FrA2Nbf(IV)-02). Condensed aromatic diamine compounds typified by pyrenediamine compounds such as 1,6FLPAPrn, 1,6mMemFLPAPrn, and 1,6BnfAPrn-03 are particularly preferable because of their high hole-trapping properties, high emission efficiency, and high reliability.

Examples of the phosphorescent substance that can be used as the guest material in the light-emitting layer 113 are as follows.

Examples include organometallic iridium complexes having a 4H-triazole skeleton, such as tris{2-[5-(2-methylphenyl)-4-(2,6-dimethylphenyl)-4H-1,2,4-triazol-3-yl-$N^2$]phenyl-κC}iridium(III) (abbreviation: [Ir(mpptz-dmp)$_3$]), tris(5-methyl-3,4-diphenyl-4H-1,2,4-triazolato)iridium(III) (abbreviation: [Ir(Mptz)$_3$]), and tris[4-(3-biphenyl)-5-isopropyl-3-phenyl-4H-1,2,4-triazolato]iridium(III) (abbreviation: [Ir(iPrptz-3b)$_3$]); organometallic iridium complexes having a 1H-triazole skeleton, such as tris[3-methyl-1-(2-methylphenyl)-5-phenyl-1H-1,2,4-triazolato]iridium(III) (abbreviation: [Ir(Mptz1-mp)$_3$]) and tris(1-methyl-5-phenyl-3-propyl-1H-1,2,4-triazolato)iridium(III) (abbreviation: [Ir(Prptz1-Me)$_3$]); organometallic iridium complexes having an imidazole skeleton, such as fac-tris[1-(2,6-diisopropylphenyl)-2-phenyl-1H-imidazole]iridium(III) (abbreviation: [Ir(iPrpmi)$_3$]) and tris[3-(2,6-dimethylphenyl)-7-methylimidazo[1,2-f]phenanthridinato]iridium(III) (abbreviation: [Ir(dmpimpt-Me)$_3$]); and organometallic iridium complexes in which a phenylpyridine derivative having an electron-withdrawing group is a ligand, such as bis[2-(4',6'-difluorophenyl)pyridinato-N,$C^{2'}$]iridium(III) tetrakis(1-pyrazolyl)borate (abbreviation: FIr6), bis[2-(4',6'-difluorophenyl)pyridinato-N,$C^{2'}$]iridium(III) picolinate (abbreviation: FIrpic), bis{2-[3',5'-bis(trifluoromethyl)phenyl]pyridinato-N,$C^{2'}$}iridium(III) picolinate (abbreviation: [Ir(CF$_3$ppy)$_2$(pic)]), and bis[2-(4',6'-difluorophenyl)pyridinato-N,$C^{2'}$]iridium(III) acetylacetonate (abbreviation: FIracac). These compounds exhibit blue phosphorescence and have an emission peak at 440 nm to 520 nm.

Other examples include organometallic iridium complexes having a pyrimidine skeleton, such as tris(4-methyl-6-phenylpyrimidinato)iridium(III) (abbreviation: [Ir(mppm)$_3$]), tris(4-t-butyl-6-phenylpyrimidinato)iridium(III) (abbreviation: [Ir(tBuppm)$_3$]), (acetylacetonato)bis(6-methyl-4-phenylpyrimidinato)iridium(III) (abbreviation: [Ir(mppm)$_2$(acac)]), (acetylacetonato)bis(6-tert-butyl-4-phenylpyrimidinato)iridium(III) (abbreviation: [Ir(tBuppm)$_2$(acac)]), (acetylacetonato)bis[6-(2-norbornyl)-4-phenylpyrimidinato]iridium(III) (abbreviation: [Ir(nbppm)$_2$(acac)]), (acetylacetonato)bis[5-methyl-6-(2-methylphenyl)-4-phenylpyrimidinato]iridium(III) (abbreviation: [Ir(mpmppm)$_2$(acac)]), and (acetylacetonato)bis(4,6-diphenylpyrimidinato)iridium(III) (abbreviation: [Ir(dppm)$_2$(acac)]); organometallic iridium complexes having a pyrazine skeleton, such as (acetylacetonato)bis(3,5-dimethyl-2-phenylpyrazinato)iridium(III) (abbreviation: [Ir(mppr-Me)$_2$(acac)]) and (acetylacetonato)bis(5-isopropyl-3-methyl-2-phenylpyrazinato)iridium(III) (abbreviation: [Ir(mppr-iPr)$_2$(acac)]); organometallic iridium complexes having a pyridine skeleton, such as tris(2-phenylpyridinato-N,$C^{2'}$)iridium(III) (abbreviation: [Ir(ppy)$_3$]), bis(2-phenylpyridinato-N,$C^{2'}$)iridium(III) acetylacetonate (abbreviation: [Ir(ppy)$_2$(acac)]), bis(benzo[h]quinolinato)iridium(III) acetylacetonate (abbreviation: [Ir(bzq)$_2$(acac)]), tris(benzo[h]quinolinato)iridium(III) (abbreviation: [Ir(bzq)$_3$]), tris(2-phenylquinolinato-N,$C^{2'}$)iridium(III) (abbreviation: [Ir(pq)$_3$]), and bis(2-phenylquinolinato-N,$C^{2'}$)iridium(III) acetylacetonate (abbreviation: [Ir(pq)$_2$(acac)]); and rare earth metal complexes such as tris(acetylacetonato) (monophenanthroline)terbium(III) (abbreviation: [Tb(acac)$_3$(Phen)]). These are mainly compounds that exhibit green phosphorescence and have an emission peak at 500 nm to 600 nm. Note that organometallic iridium complexes having a pyrimidine skeleton have distinctively high reliability and emission efficiency and thus are particularly preferable.

Other examples include organometallic iridium complexes having a pyrimidine skeleton, such as (diisobutyrylmethanato)bis[4,6-bis(3-methylphenyl)pyrimidinato]iridium(III) (abbreviation: [Ir(5mdppm)$_2$(dibm)]), bis[4,6-bis(3-methylphenyl)pyrimidinato](dipivaloylmethanato)iridium(III) (abbreviation: [Ir(5mdppm)$_2$(dpm)]), and bis[4,6-di(naphthalen-1-yl)pyrimidinato](dipivaloylmethanato)iridium(III) (abbreviation: [Ir(dlnpm)$_2$(dpm)]); organometallic iridium complexes having a pyrazine skeleton, such as (acetylacetonato)bis(2,3,5-triphenylpyrazinato)iridium(III) (abbreviation: [Ir(tppr)$_2$(acac)]), bis(2,3,5-triphenylpyrazinato)(dipivaloylmethanato)iridium(III) (abbreviation: [Ir(tppr)$_2$(dpm)]), and (acetylacetonato)bis[2,3-bis(4-fluorophenyl)quinoxalinato]iridium(III) (abbreviation: [Ir(Fdpq)$_2$(acac)]); organometallic iridium complexes having a pyridine skeleton, such as tris(1-phenylisoquinolinato-N,$C^{2'}$)iridium(III) (abbreviation: [Ir(piq)$_3$]) and bis(1-phenylisoquinolinato-N,$C^2$)iridium(III) acetylacetonate (abbreviation: [Ir(piq)$_2$(acac)]); platinum complexes such as 2,3,7,8,12,13,17,18-octaethyl-21H,23H-porphyrinplatinum (II) (abbreviation: PtOEP); and rare earth metal complexes such as tris(1,3-diphenyl-1,3-propanedionato) (monophenanthroline)europium(III) (abbreviation: [Eu(DBM)$_3$(Phen)]) and tris[i-(2-thenoyl)-3,3,3-trifluoroacetonato](monophenanthroline)europium(III) (abbreviation: [Eu(TTA)$_3$(Phen)]). These compounds exhibit red phosphorescence and have an emission peak at 600 nm to 700 nm. Furthermore, organometallic iridium complexes having a pyrazine skeleton can provide red light emission with favorable chromaticity.

Besides the above-described materials, known phosphorescent substances can also be used.

Examples of the TADF material that can be used as the guest material in the light-emitting layer 113 are as follows.

A fullerene, a derivative thereof, an acridine, a derivative thereof, an eosin derivative, or the like can be used. Furthermore, a metal-containing porphyrin, such as a porphyrin containing magnesium (Mg), zinc (Zn), cadmium (Cd), tin (Sn), platinum (Pt), indium (In), or palladium (Pd), can be given. Examples of the metal-containing porphyrin include a protoporphyrin-tin fluoride complex ($SnF_2$(Proto IX)), a mesoporphyrin-tin fluoride complex ($SnF_2$(Meso IX)), a hematoporphyrin-tin fluoride complex ($SnF_2$(Hemato IX)), a coproporphyrin tetramethyl ester-tin fluoride complex ($SnF_2$(Copro III-4Me)), an octaethylporphyrin-tin fluoride complex ($SnF_2$(OEP)), an etioporphyrin-tin fluoride complex ($SnF_2$(Etio I)), and an octaethylporphyrin-platinum chloride complex ($PtCl_2$OEP), which are represented by the following structural formulae.

[Chemical Formula 15]

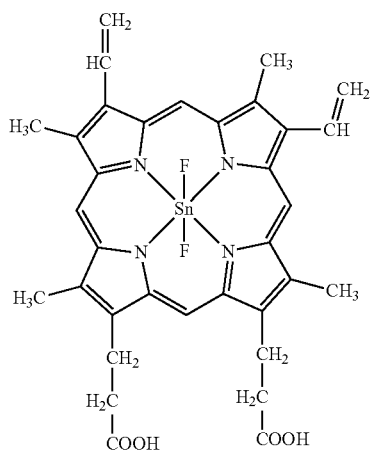

$SnF_2$(Proto IX)

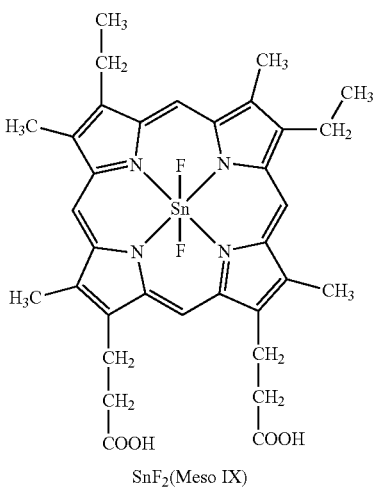

$SnF_2$(Meso IX)

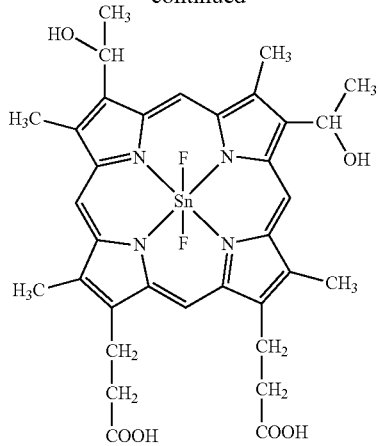

$SnF_2$(Hemato IX)

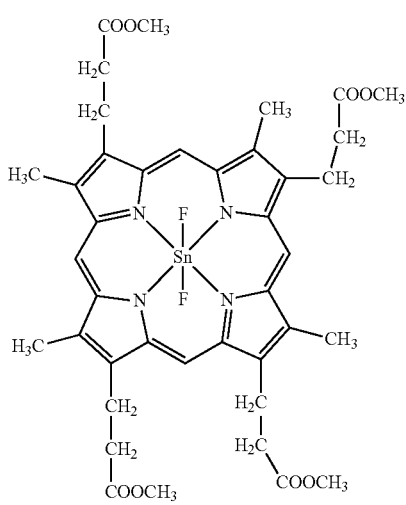

$SnF_2$(Copro III-4Me)

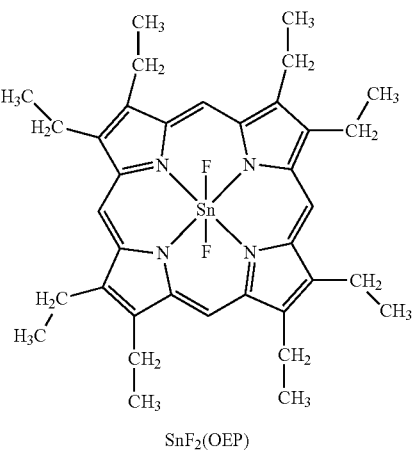

$SnF_2$(OEP)

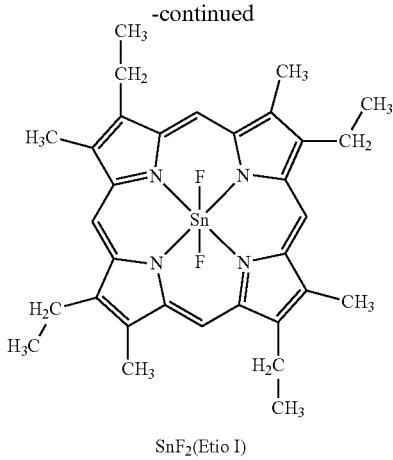

SnF₂(Etio I)

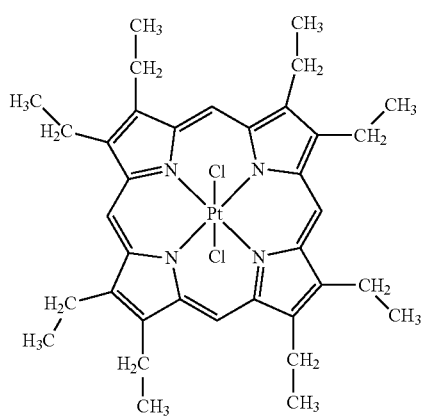

PtCl₂OEP

In addition, a heterocyclic compound having a π-electron rich heteroaromatic ring and a π-electron deficient heteroaromatic ring, such as 2-(biphenyl-4-yl)-4,6-bis(12-phenylindolo[2,3-a]carbazol-11-yl)-1,3,5-triazine (abbreviation: PIC-TRZ), 2-{4-[3-(N-phenyl-9H-carbazol-3-yl)-9H-carbazol-9-yl]phenyl}-4,6-diphenyl-1,3,5-triazine (abbreviation: PCCzPTzn), 2-[4-(10H-phenoxazin-10-yl)phenyl]-4,6-diphenyl-1,3,5-triazine (abbreviation: PXZ-TRZ), 3-[4-(5-phenyl-5,10-dihydrophenazin-10-yl)phenyl]-4,5-diphenyl-1,2,4-triazole (abbreviation: PPZ-3TPT), 3-(9,9-dimethyl-9H-acridin-10-yl)-9H-xanthen-9-one (abbreviation: ACRXTN), bis[4-(9,9-dimethyl-9,10-dihydroacridine)phenyl]sulfone (abbreviation: DMAC-DPS), 10-phenyl-10H,10'H-spiro[acridin-9,9'-anthracen]-10'-one (abbreviation: ACRSA), 4-(9'-phenyl-3,3'-bi-9H-carbazol-9-yl)benzofuro[3,2-d]pyrimidine (abbreviation: 4PCCzBfpm), 4-[4-(9'-phenyl-3,3'-bi-9H-carbazol-9-yl)phenyl]benzofuro[3,2-d]pyrimidine (abbreviation: 4PCCzPBfpm), and 9-[3-(4,6-diphenyl-1,3,5-triazin-2-yl)phenyl]-9'-phenyl-2,3'-bi-9H-carbazole (abbreviation: mPCCzPTzn-02), which are represented by the following structural formulae, may be used.

[Chemical Formula 16]

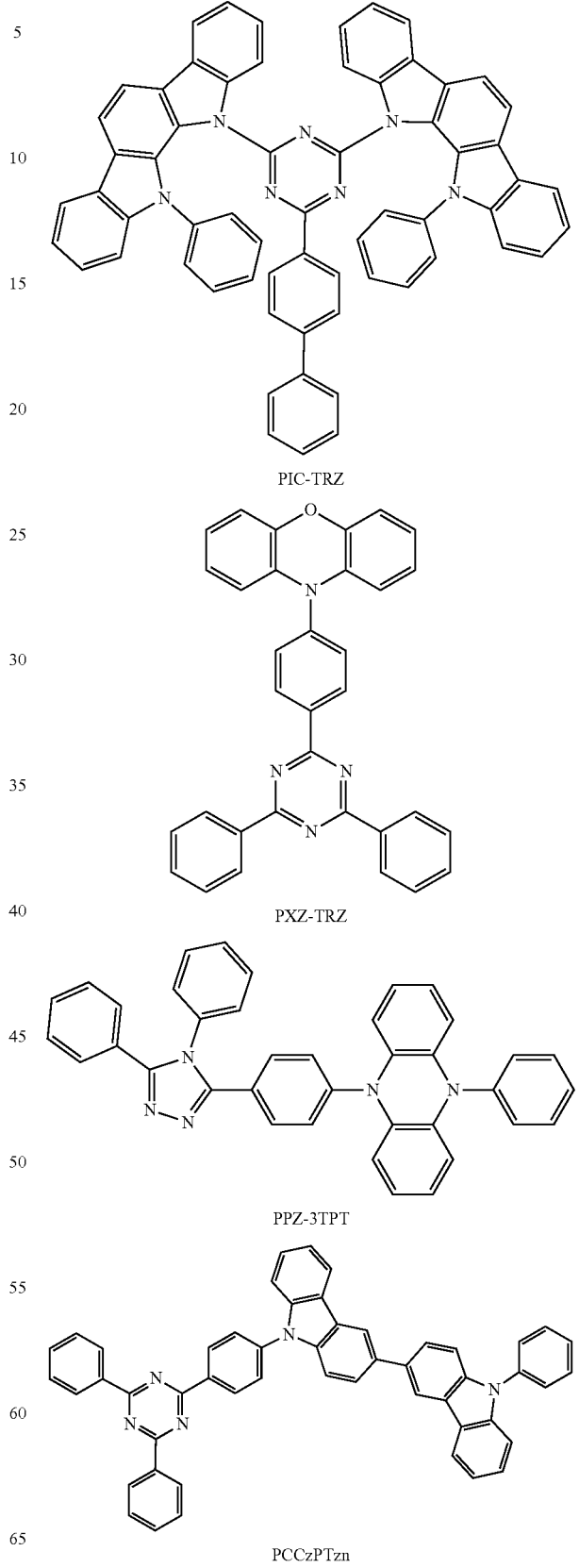

PIC-TRZ

PXZ-TRZ

PPZ-3TPT

PCCzPTzn

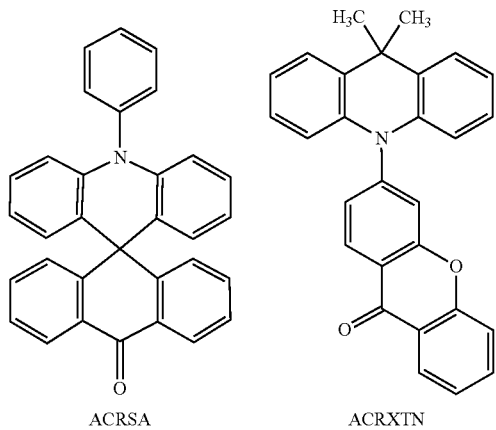

ACRSA

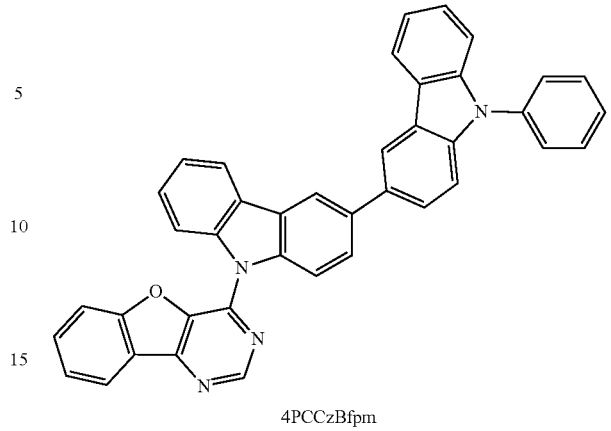

ACRXTN

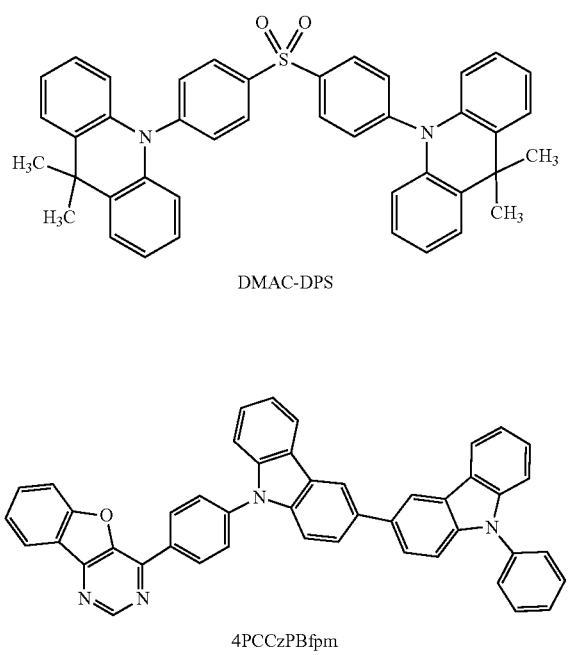

DMAC-DPS

4PCCzPBfpm

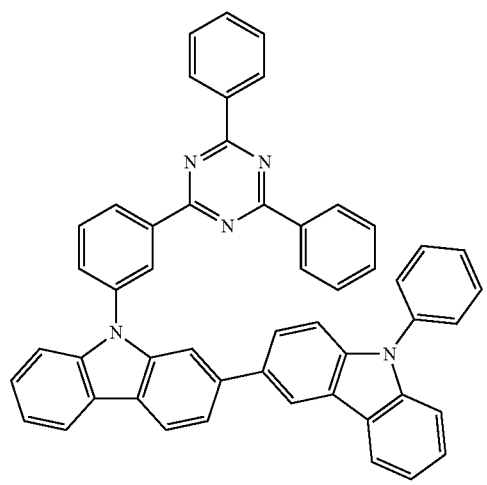

mPCCzPTzn-02

4PCCzBfpm

The heterocyclic compound is preferable because of having both a high electron-transport property and a high hole-transport property owing to a π-electron rich heteroaromatic ring and a π-electron deficient heteroaromatic ring. Among skeletons having a π-electron deficient heteroaromatic ring, a pyridine skeleton, a diazine skeleton (a pyrimidine skeleton, a pyrazine skeleton, and a pyridazine skeleton) and a triazine skeleton are particularly preferable because of their high stability and reliability. In particular, a benzofuropyrimidine skeleton, a benzothienopyrimidine skeleton, a benzofuropyrazine skeleton, and a benzothienopyrazine skeleton are preferable because of their high acceptor properties and reliability.

Among skeletons having a π-electron rich heteroaromatic ring, an acridine skeleton, a phenoxazine skeleton, a phenothiazine skeleton, a furan skeleton, a thiophene skeleton, and a pyrrole skeleton have high stability and reliability; therefore, at least one of these skeletons is preferably included. Note that a dibenzofuran skeleton and a dibenzothiophene skeleton are preferable as the furan skeleton and the thiophene skeleton, respectively. As the pyrrole skeleton, an indole skeleton, a carbazole skeleton, an indolocarbazole skeleton, a bicarbazole skeleton, and a 3-(9-phenyl-9H-carbazol-3-yl)-9H-carbazole skeleton are particularly preferable.

Note that a substance in which a π-electron rich heteroaromatic ring and a π-electron deficient heteroaromatic ring are directly bonded to each other is particularly preferable because the electron-donating property of the π-electron rich heteroaromatic ring and the electron-accepting property of the π-electron deficient heteroaromatic ring are both increased and the energy difference between the S1 level and the T1 level becomes small, and thus thermally activated delayed fluorescence can be obtained efficiently. Note that an aromatic ring to which an electron-withdrawing group such as a cyano group is bonded may be used instead of the π-electron deficient heteroaromatic ring. As a π-electron rich skeleton, an aromatic amine skeleton, a phenazine skeleton, or the like can be used. As a π-electron deficient skeleton, a xanthene skeleton, a thioxanthene dioxide skeleton, an oxadiazole skeleton, a triazole skeleton, an imidazole skeleton, an anthraquinone skeleton, a boron-containing skeleton such as phenylborane or boranthrene, an aromatic ring or a heteroaromatic ring having a nitrile group or a cyano group, such as benzonitrile or cyanobenzene, a carbonyl skeleton such as benzophenone, a phosphine oxide skeleton, a sulfone skeleton, or the like can be used.

As described above, a π-electron deficient skeleton and a π-electron rich skeleton can be used instead of at least one of the π-electron deficient heteroaromatic ring and the π-electron rich heteroaromatic ring.

Note that the TADF material is a material that has a small difference between the S1 level and the T1 level and has a function of converting triplet excitation energy into singlet excitation energy by reverse intersystem crossing. Thus, it is possible to upconvert triplet excitation energy into singlet excitation energy (reverse intersystem crossing) using a little thermal energy and to efficiently generate a singlet excited state. In addition, the triplet excitation energy can be converted into luminescence.

An exciplex whose excited state is formed by two kinds of substances has an extremely small difference between the S1 level and the T1 level and has a function of a TADF material that can convert triplet excitation energy into singlet excitation energy.

Note that a phosphorescent spectrum observed at low temperatures (e.g., 77 K to 10 K) is used for an index of the T1 level. When the level of energy with a wavelength of the line obtained by extrapolating a tangent to the fluorescent spectrum at a tail on the short wavelength side is the S1 level and the level of energy with a wavelength of the line obtained by extrapolating a tangent to the phosphorescent spectrum at a tail on the short wavelength side is the T1 level, the difference between S1 and T1 of the TADF material is preferably smaller than or equal to 0.3 eV, further preferably smaller than or equal to 0.2 eV.

In the case where the TADF material is used as the guest material in the light-emitting layer 113, the S1 level of the host material is preferably higher than the S1 level of the TADF material. In addition, the T1 level of the host material is preferably higher than the T1 level of the TADF material.

As the hole-transport material that can be used as the host material in the light-emitting layer 113, it is preferable to use a substance having a hole mobility higher than or equal to $1 \times 10^{-6}$ cm$^2$/Vs in the case where the square root of the electric field strength [V/cm] is 600. Examples of the substance are shown below.

Examples include compounds having an aromatic amine skeleton, such as 4,4'-bis[N-(1-naphthyl)-N-phenylamino]biphenyl (abbreviation: NPB), N,N'-bis(3-methylphenyl)-N,N-diphenyl-[1,1'-biphenyl]-4,4'-diamine (abbreviation: TPD), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), 4-phenyl-4'-(9-phenyl-9H-carbazol-3-yl)triphenylamine (abbreviation: PCBA1BP), 4,4'-diphenyl-4"-(9-phenyl-9H-carbazol-3-yl)triphenylamine (abbreviation: PCBBi1BP), 4-(1-naphthyl)-4'-(9-phenyl-9H-carbazol-3-yl)triphenylamine (abbreviation: PCBANB), 4,4'-di(1-naphthyl)-4"-(9-phenyl-9H-carbazol-3-yl)triphenylamine (abbreviation: PCBNBB), 9,9-dimethyl-N-phenyl-N-[4-(9-phenyl-9H-carbazol-3-yl)phenyl]fluoren-2-amine (abbreviation: PCBAF), and N-phenyl-N-[4-(9-phenyl-9H-carbazol-3-yl)phenyl]spiro-9,9'-bifluoren-2-amine (abbreviation: PCBASF); compounds having a carbazole skeleton, such as 1,3-bis(N-carbazolyl)benzene (abbreviation: mCP), 4,4'-di(N-carbazolyl)biphenyl (abbreviation: CBP), 3,6-bis(3,5-diphenylphenyl)-9-phenylcarbazole (abbreviation: CzTP), and 3,3'-bis(9-phenyl-9H-carbazole) (abbreviation: PCCP); compounds having a thiophene skeleton, such as 4,4',4"-(benzene-1,3,5-triyl)tri(dibenzothiophene) (abbreviation: DBT3P-II), 2,8-diphenyl-4-[4-(9-phenyl-9H-fluoren-9-yl)phenyl]dibenzothiophene (abbreviation: DBTFLP-III), and 4-[4-(9-phenyl-9H-fluoren-9-yl)phenyl]-6-phenyldibenzothiophene (abbreviation: DBTFLP-IV); and compounds having a furan skeleton, such as 4,4',4"-(benzene-1,3,5-triyl)tri(dibenzofuran) (abbreviation: DBF3P-II) and 4-{3-[3-(9-phenyl-9H-fluoren-9-yl)phenyl]phenyl}dibenzofuran (abbreviation: mmDBFFLBi-II). Among the above, the compound having an aromatic amine skeleton and the compound having a carbazole skeleton are preferable because these compounds are highly reliable and have high hole-transport properties to contribute to a reduction in driving voltage. In addition, the organic compounds given as examples of the above hole-transport material can also be used.

As the electron-transport material that can be used as the host material in the light-emitting layer 113, it is preferable to use a substance having an electron mobility higher than or equal to $1 \times 10^{-6}$ cm$^2$/Vs in the case where the square root of the electric field strength [V/cm] is 600. Examples of the substance are shown below. In addition, an electron-transport material that can be used in the electron-transport layer 114, which will be described later, can also be used.

Examples include metal complexes such as bis(10-hydroxybenzo[h]quinolinato)beryllium(II) (abbreviation: BeBq2), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), and bis[2-(2-benzothiazolyl)phenolato]zinc(II) (abbreviation: ZnBTZ); heterocyclic compounds having a polyazole skeleton, such as 2-(4-biphenylyl)-5-(4-tert-butylphenyl)-1,3,4-oxadiazole (abbreviation: PBD), 3-(4-biphenylyl)-4-phenyl-5-(4-tert-butylphenyl)-1,2,4-triazole (abbreviation: TAZ), 1,3-bis[5-(p-tert-butylphenyl)-1,3,4-oxadiazol-2-yl]benzene (abbreviation: OXD-7), 9-[4-(5-phenyl-1,3,4-oxadiazol-2-yl)phenyl]-9H-carbazole (abbreviation: CO11), 2,2',2"-(1,3,5-benzenetriyl)tris(1-phenyl-1H-benzimidazole) (abbreviation: TPBI), and 2-[3-(dibenzothiophen-4-yl)phenyl]-1-phenyl-1H-benzimidazole (abbreviation: mDBTBIm-II); heterocyclic compounds having a diazine skeleton, such as 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[3'-(9H-carbazol-9-yl)biphenyl-3-yl]dibenzo[f,h]quinoxaline (abbreviation: 2mCzBPDBq), 4,6-bis[3-(phenanthren-9-yl)phenyl]pyrimidine (abbreviation: 4,6mPnP2Pm), and 4,6-bis[3-(4-dibenzothienyl)phenyl]pyrimidine (abbreviation: 4,6mDBTP2Pm-II), and heterocyclic compounds having a pyridine skeleton, such as 3,5-bis[3-(9H-carbazol-9-yl)phenyl]pyridine (abbreviation: 35DCzPPy) and 1,3,5-tri[3-(3-pyridyl)phenyl]benzene (abbreviation: TmPyPB). Among the above, the heterocyclic compound having a diazine skeleton and the heterocyclic compound having a pyridine skeleton are preferable because of having high reliability. In particular, the heterocyclic compound having a diazine (pyrimidine or pyrazine) skeleton has a high electron-transport property and contributes to a reduction in driving voltage.

In the case where the TADF material is used as the host material in the light-emitting layer 113, the above-described materials can also be used. Note that when the TADF material is used as the host material, triplet excitation energy generated in the TADF material is converted into singlet excitation energy by reverse intersystem crossing and transferred to the emission center substance, whereby the emission efficiency of the light-emitting element can be increased. At this time, the TADF material functions as an energy donor, and the emission center substance functions as an energy acceptor. Therefore, the use of the TADF material as the host material is very effective in the case where a fluorescent substance is used as the guest material. In that case, the S1 level of the TADF material is preferably higher than the S1 level of the fluorescent substance in order to achieve high emission efficiency. Furthermore, the T1 level of the TADF material is preferably higher than the S1 level of the fluorescent substance. Therefore, the T1 level of the TADF material is preferably higher than the T1 level of the fluorescent substance.

It is also preferable to use a TADF material that emits light whose wavelength overlaps with the wavelength on a lowest-energy-side absorption band of the fluorescent substance. This enables smooth transfer of excitation energy from the TADF material to the fluorescent substance and accordingly enables efficient light emission, which is preferable.

In order that singlet excitation energy is efficiently generated from the triplet excitation energy by reverse intersystem crossing, carrier recombination preferably occurs in the TADF material. It is also preferable that the triplet excitation energy generated in the TADF material not be transferred to the triplet excitation energy of the fluorescent substance. For that reason, the fluorescent substance preferably has a protective group around a luminophore (a skeleton that causes light emission) of the fluorescent substance. As the protective group, a substituent having no π bond and saturated hydrocarbon are preferably used. Specific examples include an alkyl group having 3 to 10 carbon atoms, a substituted or unsubstituted cycloalkyl group having 3 to 10 carbon atoms, and a trialkylsilyl group having 3 to 10 carbon atoms. It is further preferable that the fluorescent substance have a plurality of protective groups. The substituent having no π bond has a poor carrier-transport property; thus, the TADF material and the luminophore of the fluorescent substance can be made away from each other with little influence on carrier transportation or carrier recombination. Here, the luminophore refers to an atomic group (a skeleton) that causes light emission in a fluorescent substance. The luminophore is preferably a skeleton having a π bond, further preferably includes an aromatic ring, and still further preferably includes a condensed aromatic ring or a condensed heteroaromatic ring. Examples of the condensed aromatic ring or the condensed heteroaromatic ring include a phenanthrene skeleton, a stilbene skeleton, an acridone skeleton, a phenoxazine skeleton, and a phenothiazine skeleton. Specifically, a fluorescent substance having any of a naphthalene skeleton, an anthracene skeleton, a fluorene skeleton, a chrysene skeleton, a triphenylene skeleton, a tetracene skeleton, a pyrene skeleton, a perylene skeleton, a coumarin skeleton, a quinacridone skeleton, and a naphthobisbenzofuran skeleton is preferable because of its high fluorescence quantum yield.

In the case where a fluorescent substance is used as the guest material in the light-emitting layer 113, a material having an anthracene skeleton is favorably used as the host material. The use of a substance having an anthracene skeleton makes it possible to obtain a light-emitting layer with high emission efficiency and high durability. Note that as the substance having an anthracene skeleton, a substance having a diphenylanthracene skeleton, in particular, a 9,10-diphenylanthracene skeleton is chemically stable and thus is preferable.

The host material preferably has a carbazole skeleton, in which case the hole injection and transport properties are improved; further preferably, the host material has a benzo-carbazole skeleton where a benzene ring is further condensed to carbazole, in which case the HOMO level thereof is shallower than that in the case of using carbazole by approximately 0.1 eV and thus holes enter the host material easily. In particular, the host material preferably has a dibenzocarbazole skeleton, in which case the HOMO level thereof is shallower than that in the case of using carbazole by approximately 0.1 eV so that holes enter the host material easily, the hole-transport property is improved, and the heat resistance is increased.

Thus, a substance having both of a 9,10-diphenylanthracene skeleton, which is an anthracene skeleton, and a carbazole skeleton (or a benzocarbazole skeleton or a dibenzocarbazole skeleton) is further preferable as the host material. Note that in terms of improving the hole injection and transport properties described above, a benzofluorene skeleton or a dibenzo fluorene skeleton may be used instead of a carbazole skeleton. Examples of such a substance include 9-phenyl-3-[4-(10-phenyl-9-anthryl)phenyl]-9H-carbazole (abbreviation: PCzPA), 3-[4-(1-naphthyl)-phenyl]-9-phenyl-9H-carbazole (abbreviation: PCPN), 9-[4-(10-phenyl-9-anthracenyl)phenyl]-9H-carbazole (abbreviation: CzPA), 7-[4-(10-phenyl-9-anthryl)phenyl]-7H-dibenzo[c,g]carbazole (abbreviation: cgDBCzPA), 6-[3-(9,10-diphenyl-2-anthryl)phenyl]-benzo[b]naphtho[1,2-d]furan (abbreviation: 2mBnfPPA), 9-phenyl-10-{4-(9-phenyl-9H-fluoren-9-yl)biphenyl-4'-yl}anthracene (abbreviation: FLPPA), and 9-(1-naphthyl)-10-[4-(2-naphthyl)phenyl]anthracene (abbreviation: α,N-βNPAnth). In particular, CzPA, cgDBCzPA, 2mBnfPPA, and PCzPA are preferable because they exhibit excellent characteristics.

Note that the host material may be a mixture of a plurality of kinds of substances; in the case of using a mixed host material, it is preferable to mix an electron-transport material and a hole-transport material. By mixing the electron-transport material and the hole-transport material, the transport properties of the light-emitting layer 113 can be easily adjusted and a recombination region can be easily controlled. The weight ratio of the content of the hole-transport material to the content of the electron-transport material is the hole-transport material: the electron-transport material=1:19 to 19:1.

Note that a phosphorescent substance can be used as part of the host material in the case where the host material is formed by mixing a plurality of kinds of substances as described above. When a fluorescent substance is used as the emission center material, a phosphorescent substance can be used as an energy donor for supplying excitation energy to the fluorescent substance.

The materials mixed in the above manner may form an exciplex. When a combination of materials in this case is selected so as to form an exciplex that exhibits light emission whose wavelength overlaps with the wavelength on a lowest-energy-side absorption band of the light-emitting substance, energy can be transferred smoothly and light emission can be obtained efficiently. The use of such a structure is preferable because the driving voltage can be reduced.

Note that at least one of the materials forming an exciplex may be a phosphorescent substance. In this case, triplet excitation energy can be efficiently converted into singlet excitation energy by reverse intersystem crossing.

Note that a combination of materials forming an exciplex is preferably such that the HOMO level of a hole-transport material is higher than or equal to the HOMO level of an electron-transport material. In addition, the LUMO level of the hole-transport material is preferably higher than or equal to the LUMO level of the electron-transport material. Note that the LUMO levels and the HOMO levels of the materials can be derived from the electrochemical characteristics (the reduction potentials and the oxidation potentials) of the materials that are measured by cyclic voltammetry (CV).

Note that the formation of an exciplex can be confirmed by a phenomenon in which the emission spectrum of a mixed film of a hole-transport material and an electron-transport material is shifted to the longer wavelength side than the emission spectrum of each of the materials (or has another peak on the longer wavelength side), observed by comparison of the emission spectra of the hole-transport material, the electron-transport material, and the mixed film of these materials, for example. Alternatively, the formation of an exciplex can be confirmed by a difference in transient response, such as a phenomenon in which the transient photoluminescence (PL) lifetime of the mixed film has a longer lifetime component or has a larger proportion of delayed components than that of each of the materials, observed by comparison of transient PL of the hole-transport material, the electron-transport material, and the mixed film of these materials. The transient PL can be rephrased as transient electroluminescence (EL). That is, the formation of an exciplex can also be confirmed by a difference in transient response observed by comparison of the transient EL of the hole-transport material, the material having an electron-transport property, and the mixed film of the materials.

<Electron-Transport Layer>

The electron-transport layer 114 transports electrons, which are injected from the second electrode 102, to the light-emitting layer 113 and is provided in contact with the light-emitting layer 113. Note that the electron-transport layer 114 includes an electron-transport material. The electron-transport material used in the electron-transport layer 114 is preferably a substance having an electron mobility higher than or equal to $1 \times 10^{-6}$ cm$^2$/Vs. Note that other substances can also be used as long as they have a property of transporting more electrons than holes. An electron-transport material and an organometallic complex that is an alkali metal or an alkaline earth metal may be used for the electron-transport layer 114. In that case, an electron-transport material having a HOMO level higher than or equal to −6.0 eV is preferably used as the electron-transport material. The electron mobility of the electron-transport material with a HOMO level higher than or equal to −6.0 eV is preferably higher than or equal to $1 \times 10^{-7}$ cm$^2$/Vs and lower than or equal to $1 \times 10^{-5}$ cm$^2$/Vs, further preferably higher than or equal to $1 \times 10^{-7}$ cm$^2$/Vs and lower than or equal to $5 \times 10^{-5}$ cm$^2$/Vs in the case where the square root of the electric field strength [V/cm] is 600.

Note that the electron-transport material with a HOMO level higher than or equal to −6.0 eV is preferably an organic compound having an anthracene skeleton, an organic compound having an anthracene skeleton and a heterocyclic skeleton, or the like. It is thus preferable to use a quinoxaline derivative of one embodiment of the present invention as the electron-transport material. In addition, some of the above-described electron-transport materials that can be used as the host material, or the materials that are listed above as the host material used in combination with the fluorescent substance can be used in the electron-transport layer 114.

As the organometallic complex of an alkali metal or an alkaline earth metal, an organic complex of lithium, sodium, or the like is preferable, and 8-hydroxyquinolinato-lithium (abbreviation: Liq) is particularly preferable.

The electron mobility of the electron-transport material with a HOMO level higher than or equal to −6.0 eV that is used for the electron-transport layer 114 (the electron mobility in the case where the square root of the electric field strength [V/cm] is 600) is preferably lower than the electron mobility of the host material used in the light-emitting layer 113. Lowering the electron-transport property of the electron-transport layer enables control of the amount of electrons injected into the light-emitting layer and can prevent the light-emitting layer from having excess electrons.

In the case where the electron-transport layer 114 includes an organic metal complex of an alkali metal or an alkaline earth metal, the electron-transport layer 114 may be formed of two or more layers with different amounts of the organic metal complex; it is particularly preferable to employ a structure in which the amount of the organic metal complex is large at an interface with the light-emitting layer.

<Electron-Injection Layer>

The electron-injection layer 115 is a layer for increasing the efficiency of electron injection from the second electrode (a cathode) 102 and is preferably formed using a material whose LUMO level value has a small difference (0.5 eV or less) from the work function value of the material of the second electrode (the cathode) 102. Thus, the electron-injection layer 115 can be formed using an alkali metal, an alkaline earth metal, or a compound thereof, such as lithium, cesium, lithium fluoride (LiF), cesium fluoride (CsF), calcium fluoride (CaF$_2$), 8-hydroxyquinolinato-lithium (abbreviation: Liq), 2-(2-pyridyl)phenolatolithium (abbreviation: LiPP), 2-(2-pyridyl)-3-pyridinolatolithium (abbreviation: LiPPy), 4-phenyl-2-(2-pyridyl)phenolatolithium (abbreviation: LiPPP), lithium oxide (LiO$_x$), or cesium carbonate. A rare earth metal compound like erbium fluoride (ErF$_3$) can also be used.

When the charge-generation layer 104 is provided between the two EL layers (103a and 103b) as in the light-emitting device shown in FIG. 1B, a structure in which a plurality of EL layers are stacked between the pair of electrodes (also referred to as a tandem structure) can be achieved. Note that in this embodiment, functions and materials of the hole-injection layer (111), the hole-transport layer (112), the light-emitting layer (113), the electron-transport layer (114), and the electron-injection layer (115) that are illustrated in FIG. 1A are the same as those of hole-injection layers (111a and 111b), hole-transport layers (112a and 112b), light-emitting layers (113a and 113b), electron-transport layers (114a and 114b), and electron-injection layers (115a and 115b) that are illustrated in FIG. 1B.

<Charge-Generation Layer>

In the light-emitting device of FIG. 1B, the charge-generation layer 104 has a function of injecting electrons into the EL layer 103a closer to the first electrode 101 serving as the anode and injecting holes into the EL layer 103b closer to the second electrode 102 serving as the cathode when a voltage is applied between the first electrode (the anode) 101 and the second electrode (the cathode) 102. Note that the charge-generation layer 104 may have either a structure in which an electron acceptor (an acceptor) is added to a hole-transport material (a P-type layer) or a structure in which an electron donor (a donor) is added to an electron-transport material (an N-type layer). Alternatively, both of these structures may be stacked. Alternatively, the P-type layer may be formed in combination with either one or both of an electron-relay layer and an electron-injection buffer layer that will be described later. Note that forming the charge-generation layer 104 with the use of any of the above materials can inhibit the increase in driving voltage that would occur when the EL layers are stacked.

In the case where the charge-generation layer 104 has a structure in which an electron acceptor is added to a hole-transport material (a P-type layer), any of the materials described in this embodiment can be used as the hole-transport material. Examples of the electron acceptor include 7,7,8,8-tetracyano-2,3,5,6-tetrafluoroquinodimethane (abbreviation: $F_4$-TCNQ) and chloranil. Other examples include oxides of metals that belong to Group 4 to Group 8 of the periodic table. Specific examples include vanadium oxide, niobium oxide, tantalum oxide, chromium oxide, molybdenum oxide, tungsten oxide, manganese oxide, and rhenium oxide.

In the case where the charge-generation layer 104 has a structure in which an electron donor is added to an electron-transport material (an N-type layer), any of the materials described in this embodiment can be used as the electron-transport material. As the electron donor, it is possible to use an alkali metal, an alkaline earth metal, a rare earth metal, metals that belong to Groups 2 and 13 of the periodic table, or an oxide or carbonate thereof. Specifically, lithium (Li), cesium (Cs), magnesium (Mg), calcium (Ca), ytterbium (Yb), indium (In), lithium oxide, cesium carbonate, or the like is preferably used. An organic compound such as tetrathianaphthacene may be used as the electron donor.

The electron-relay layer, which is described above as preferably being combined with the P-type layer, has a function of preventing an interaction between the electron-injection buffer layer and the P-type layer and smoothly transferring electrons when provided between the electron-injection buffer layer and the P-type layer. It is preferable that the electron-relay layer include at least an electron-transport material and the LUMO level of the electron-transport material included in the electron-relay layer be between the LUMO level of the electron-accepting substance in the P-type layer and the LUMO level of a substance included in the electron-injection buffer layer. A specific energy level of the LUMO level of the electron-transport material used in the electron-relay layer is preferably higher than or equal to −5.0 eV, further preferably higher than or equal to −5.0 eV and lower than or equal to −3.0 eV. Note that as the electron-transport material used in the electron-relay layer, a phthalocyanine-based material or a metal complex having a metal-oxygen bond and an aromatic ligand is preferably used.

A substance having a high electron-injection property, such as an alkali metal, an alkaline earth metal, a rare earth metal, or a compound thereof (an alkali metal compound (including an oxide such as lithium oxide, a halide, and a carbonate such as lithium carbonate and cesium carbonate), an alkaline earth metal compound (including an oxide, a halide, and a carbonate), or a rare earth metal compound (including an oxide, a halide, and a carbonate)), can be used for the electron-injection buffer layer.

In the case where the electron-injection buffer layer contains the electron-transport material and an electron-donating substance, an organic compound such as tetrathianaphthacene (abbreviation: TTN), nickelocene, or decamethylnickelocene, as well as an alkali metal, an alkaline earth metal, a rare earth metal, or a compound thereof (an alkali metal compound (including an oxide such as lithium oxide, a halide, and a carbonate such as lithium carbonate and cesium carbonate), an alkaline earth metal compound (including an oxide, a halide, and a carbonate), or a rare earth metal compound (including an oxide, a halide, and a carbonate)), can be used as the electron-donating substance. As the electron-transport material, a material similar to the above-described material for the electron-transport layer can be used.

Although the light-emitting device shown in FIG. 1B has a structure in which the two EL layers 103 are stacked, it may have a stacked structure of three or more EL layers with charge-generation layers each provided between different EL layers.

The above-described charge-generation layer can be used instead of the above-described electron-injection layer. In that case, it is preferable that the electron-injection buffer layer, the electron-relay layer, and the P-type layer be stacked in this order from the anode side.

<Substrate>

The light-emitting device described in this embodiment can be formed over a variety of substrates. Note that the type of the substrate is not limited to a certain type. Examples of the substrate include semiconductor substrates (e.g., a single crystal substrate and a silicon substrate), an SOI substrate, a glass substrate, a quartz substrate, a plastic substrate, a metal substrate, a stainless steel substrate, a substrate including stainless steel foil, a tungsten substrate, a substrate including tungsten foil, a flexible substrate, a laminate film, paper including a fibrous material, and a base material film. Examples of the glass substrate include barium borosilicate glass, aluminoborosilicate glass, and soda lime glass. Examples of the flexible substrate, the laminate film, and the base material film include plastics typified by polyethylene terephthalate (PET), polyethylene naphthalate (PEN), and polyether sulfone (PES), a synthetic resin such as an acrylic resin, polypropylene, polyester, polyvinyl fluoride, polyvinyl chloride, polyamide, polyimide, an aramid resin, an epoxy resin, an inorganic vapor deposition film, and paper.

For fabrication of the light-emitting device in this embodiment, a vacuum process such as an evaporation method or a solution process such as a spin coating method or an ink-jet method can be used. In the case of using an evaporation method, a physical vapor deposition method (a PVD method) such as a sputtering method, an ion plating method, an ion beam evaporation method, a molecular beam evaporation method, or a vacuum evaporation method, a chemical vapor deposition method (a CVD method), or the like can be used. Specifically, the functional layers (the hole-injection layers (111, 111a, and 111b), the hole-transport layers (112, 112a, and 112b), the light-emitting layers (113, 113a, and 113b), the electron-transport layers (114, 114a, and 114b), and the electron-injection layers (115, 115a, and 115b)) included in the EL layers and the charge-generation layer 104 of the light-emitting device can be formed by an evaporation method (e.g., a vacuum evaporation method), a coating method (e.g., a dip coating method, a die coating method, a bar coating method, a spin coating method, or a spray coating method), a printing method (e.g., an ink-jet method, a screen printing (stencil) method, an offset printing (planography) method, a flexography (relief printing) method, a gravure printing method, a micro-contact printing method, or a nanoimprinting method), or the like.

Note that materials that can be used for the functional layers (the hole-injection layers (111, 111a, and 111b), the hole-transport layers (112, 112a, and 112b), the light-emitting layers (113, 113a, 113b, and 113c), the electron-transport layers (114, 114a, and 114b), and the electron-injection layers (115, 115a, and 115b)) included in the EL layers (103, 103a, and 103b) and the charge-generation layers (104, 104a, and 104b) of the light-emitting device described in this embodiment are not limited to the above materials, and other materials can also be used in combination as long as the functions of the layers are fulfilled. For example, a high molecular compound (e.g., an oligomer, a dendrimer, and a polymer), a middle molecular compound (a compound between a low molecular compound and a high molecular compound with a molecular weight of 400 to 4000), or an inorganic compound (e.g., a quantum dot material) can be used. As the quantum dot material, a colloidal quantum dot material, an alloyed quantum dot material, a core-shell quantum dot material, a core quantum dot material, or the like can be used.

The light-emitting device of one embodiment of the present invention that has the above-described structure and is used in a light-emitting apparatus can have a long lifetime.

The structures described in this embodiment can be used in an appropriate combination with the structures described in the other embodiments.

Embodiment 3

Figure 2A:
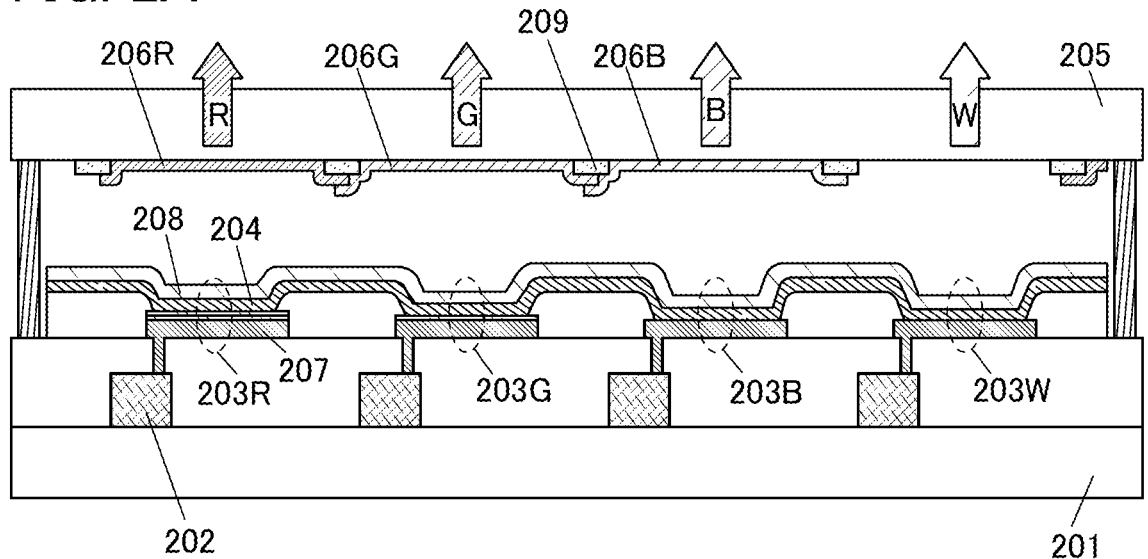
FIG. 2A is a diagram illustrating a light-emitting apparatus.

In this embodiment, a light-emitting apparatus of one embodiment of the present invention will be described. Note that a light-emitting apparatus shown in FIG. 2A is an active-matrix light-emitting apparatus in which transistors (FETs) 202 over a first substrate 201 are electrically connected to light-emitting devices (203R, 203G, 203B, and 203W); the light-emitting devices (203R, 203G, 203B, and 203W) include a common EL layer 204 and each have a microcavity structure in which the optical path length between electrodes of each light-emitting device is adjusted according to the emission color of the light-emitting device. In addition, the light-emitting apparatus is a top-emission light-emitting apparatus in which light is emitted from the EL layer 204 through color filters (206R, 206G, and 206B) formed on a second substrate 205.

In the light-emitting apparatus shown in FIG. 2A, the first electrode 207 is formed so as to function as a reflective electrode. The second electrode 208 is formed so as to function as a transflective electrode. Note that description in any of the other embodiments can be referred to for electrode materials forming the first electrode 207 and the second electrode 208 and appropriate materials can be used.

Figure 2B:
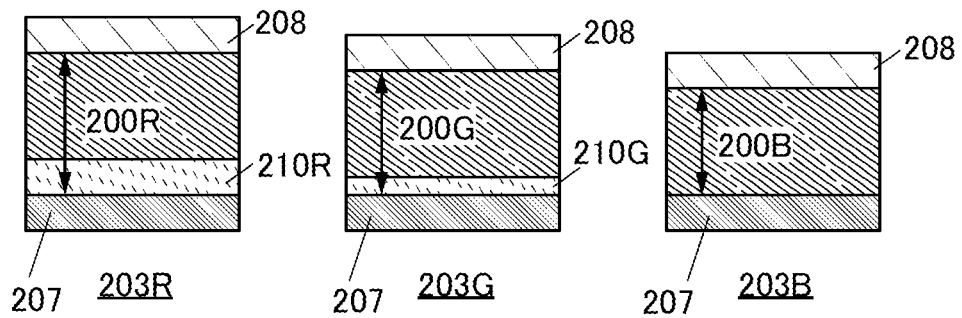
FIG. 2B is a diagram illustrating a light-emitting apparatus.

In the case where the light-emitting device 203R is a red-light-emitting device, the light-emitting device 203G is a green-light-emitting device, the light-emitting device 203B is a blue-light-emitting device, and the light-emitting device 203W is a white-light-emitting device in FIG. 2A, for example, the gap between the first electrode 207 and the second electrode 208 in the light-emitting device 203R is adjusted to have an optical path length 200R, the gap between the first electrode 207 and the second electrode 208 in the light-emitting device 203G is adjusted to have an optical path length 200G, and the gap between the first electrode 207 and the second electrode 208 in the light-emitting device 203B is adjusted to have an optical path length 200B as shown in FIG. 2B. Note that optical adjustment can be performed in such a manner that a conductive layer 210R is stacked over the first electrode 207 in the light-emitting device 203R and a conductive layer 210G is stacked over the first electrode 207 in the light-emitting device 203G as shown in FIG. 2B.

The color filters (206R, 206G, and 206B) are formed on the second substrate 205. Note that the color filters each transmit visible light in a specific wavelength range and blocks visible light in a specific wavelength range. Thus, as shown in FIG. 2A, the color filter 206R that transmits only light in the red wavelength range is provided in a position overlapping with the light-emitting device 203R, whereby red light emission can be obtained from the light-emitting device 203R. The color filter 206G that transmits only light in the green wavelength range is provided in a position overlapping with the light-emitting device 203G, whereby green light emission can be obtained from the light-emitting device 203G. The color filter 206B that transmits only light in the blue wavelength range is provided in a position overlapping with the light-emitting device 203B, whereby blue light emission can be obtained from the light-emitting device 203B. Note that the light-emitting device 203W can emit white light without a color filter. Note that a black layer (a black matrix) 209 may be provided at an end portion of one type of color filter. The color filters (206R, 206G, and 206B) and the black layer 209 may be covered with an overcoat layer using a transparent material.

Figure 2C:
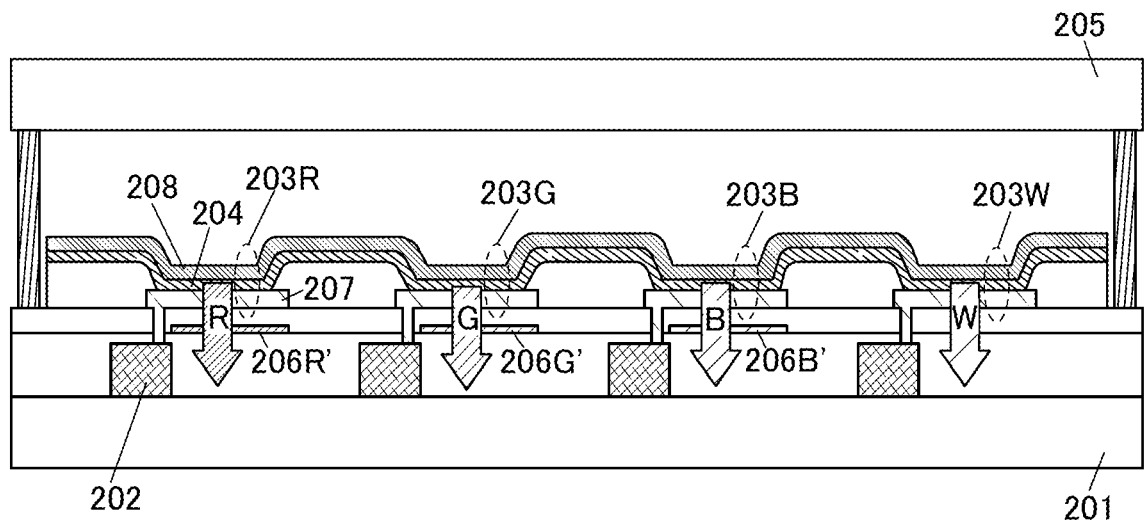
FIG. 2C is a diagram illustrating a light-emitting apparatus.

Although the light-emitting apparatus shown in FIG. 2A has a structure in which light is extracted from the second substrate 205 side (atop emission structure), the light-emitting apparatus may have a structure in which light is extracted from the first substrate 201 side where the FETs 202 are formed (a bottom emission structure) as shown in FIG. 2C. For a bottom-emission light-emitting apparatus, the first electrode 207 is formed so as to function as a transflective electrode and the second electrode 208 is formed so as to function as a reflective electrode. As the first substrate 201, a substrate having at least a light-transmitting property is used. As shown in FIG. 2C, color filters (206R', 206G', and 206B') are provided closer to the first substrate 201 than the light-emitting devices (203R, 203G, and 203B) are.

FIG. 2A shows the case where the light-emitting devices are the red-light-emitting device, the green-light-emitting device, the blue-light-emitting device, and the white-light-emitting device; however, the light-emitting devices of embodiments of the present invention are not limited to the above structures, and a yellow-light-emitting device or an orange-light-emitting device may be included. Note that description in any of the other embodiments can be referred to for materials that are used for the EL layers (a light-emitting layer, a hole-injection layer, a hole-transport layer, an electron-transport layer, an electron-injection layer, a charge-generation layer, and the like) to fabricate each of the light-emitting devices and appropriate materials can be used. In that case, a color filter needs to be appropriately selected according to the emission color of the light-emitting device.

With the above structure, a light-emitting apparatus including light-emitting devices that exhibit a plurality of emission colors can be obtained.

Note that the structures described in this embodiment can be used in an appropriate combination with any of the structures described in the other embodiments.

Embodiment 4

In this embodiment, a light-emitting apparatus of one embodiment of the present invention will be described.

The use of the device structure of the light-emitting device of one embodiment of the present invention allows fabrication of an active-matrix light-emitting apparatus or a passive-matrix light-emitting apparatus. Note that an active-matrix light-emitting apparatus has a structure including a combination of a light-emitting device and a transistor (FET). Thus, each of a passive-matrix light-emitting apparatus and an active-matrix light-emitting apparatus is included in one embodiment of the present invention. Note that any of the light-emitting devices described in the other embodiments can be used in the light-emitting apparatus described in this embodiment.

In this embodiment, an active-matrix light-emitting apparatus will be described with reference to FIG. 3.

Figure 3A:
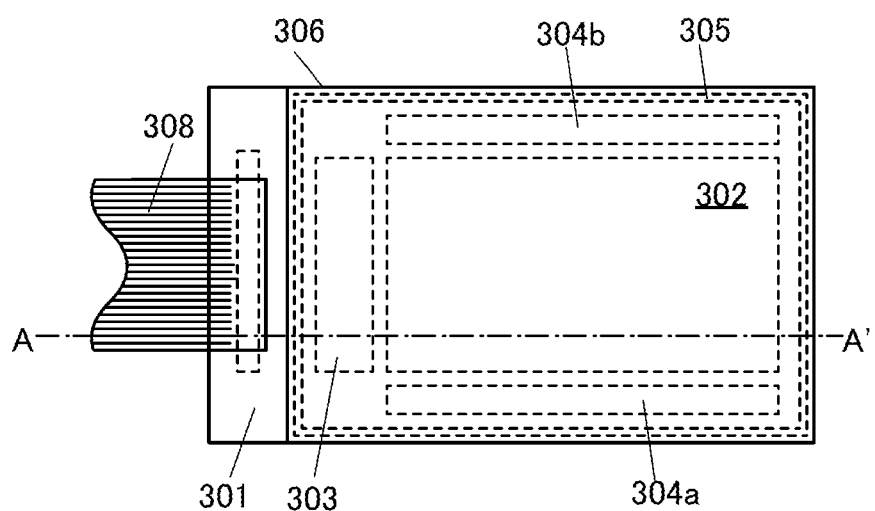
FIG. 3A is a top view illustrating a light-emitting apparatus.
Figure 3B:
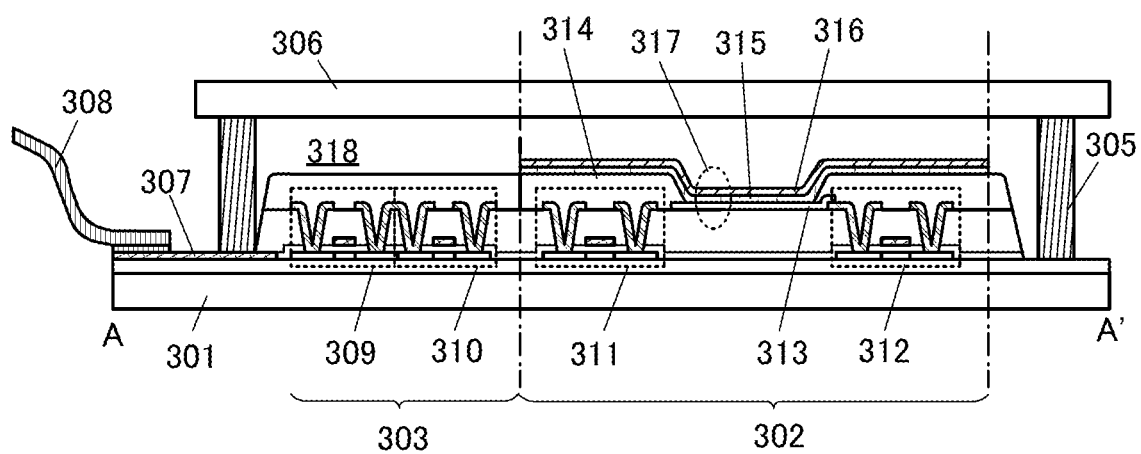
FIG. 3B is a cross-sectional view illustrating a light-emitting apparatus.

FIG. 3A is a top view showing a light-emitting apparatus, and FIG. 3B is a cross-sectional view taken along a chain line A-A' in FIG. 3A. The active-matrix light-emitting apparatus includes a pixel portion 302, a driver circuit portion (a source line driver circuit) 303, and driver circuit portions (gate line driver circuits) (304a and 304b) that are provided over a first substrate 301. The pixel portion 302 and the driver circuit portions (303, 304a, and 304b) are sealed between the first substrate 301 and a second substrate 306 with a sealant 305.

A lead wiring 307 is provided over the first substrate 301. The lead wiring 307 is electrically connected to an FPC 308 which is an external input terminal. Note that the FPC 308 transmits a signal (e.g., a video signal, a clock signal, a start signal, or a reset signal) or a potential from the outside to the driver circuit portions (303, 304a, and 304b). The FPC 308 may be provided with a printed wiring board (PWB). Note that the light-emitting apparatus provided with an FPC or a PWB is included in the category of a light-emitting apparatus.

Next, the cross-sectional structure is shown in FIG. 3B.

The pixel portion 302 is made up of a plurality of pixels each of which includes an FET (a switching FET) 311, an FET (a current control FET) 312, and a first electrode 313 electrically connected to the FET 312. Note that the number of FETs included in each pixel is not particularly limited and can be set appropriately as needed.

As FETs 309, 310, 311, and 312, for example, a staggered transistor or an inverted staggered transistor can be used without particular limitation. A top-gate transistor, a bottom-gate transistor, or the like may be used.

Note that there is no particular limitation on the crystallinity of a semiconductor that can be used for the FETs 309, 310, 311, and 312, and an amorphous semiconductor or a semiconductor having crystallinity (a microcrystalline semiconductor, a polycrystalline semiconductor, a single crystal semiconductor, or a semiconductor partly including crystal regions) may be used. The use of a semiconductor having crystallinity is preferable because deterioration of the transistor characteristics can be inhibited.

For these semiconductors, a Group 14 element, a compound semiconductor, an oxide semiconductor, an organic semiconductor, or the like can be used, for example. Typically, a semiconductor containing silicon, a semiconductor containing gallium arsenide, an oxide semiconductor containing indium, or the like can be used.

The driver circuit portion 303 includes the FET 309 and the FET 310. The driver circuit portion 303 may be formed with a circuit including transistors having the same conductivity type (either n-channel transistors or p-channel transistors) or a CMOS circuit including an n-channel transistor and a p-channel transistor. Furthermore, a structure including a driver circuit outside may be employed.

An end portion of the first electrode 313 is covered with an insulator 314. For the insulator 314, an organic compound such as a negative photosensitive resin or a positive photosensitive resin (an acrylic resin), or an inorganic compound such as silicon oxide, silicon oxynitride, or silicon nitride can be used. An upper end portion or a lower end portion of the insulator 314 preferably has a curved surface with curvature. In that case, favorable coverage with a film formed over the insulator 314 can be obtained.

An EL layer 315 and a second electrode 316 are stacked over the first electrode 313. The EL layer 315 includes a light-emitting layer, a hole-injection layer, a hole-transport layer, an electron-transport layer, an electron-injection layer, a charge-generation layer, and the like.

The structure and materials described in any of the other embodiments can be used for the structure of a light-emitting device 317 described in this embodiment. Although not shown here, the second electrode 316 is electrically connected to the FPC 308 which is an external input terminal.

Although the cross-sectional view in FIG. 3B shows only one light-emitting device 317, a plurality of light-emitting devices are arranged in a matrix in the pixel portion 302. Light-emitting devices from which light of three kinds of colors (R, G, and B) is obtained are selectively formed in the pixel portion 302, whereby a light-emitting apparatus capable of full-color display can be formed. In addition to the light-emitting devices from which light of three kinds of colors (R, G, and B) is obtained, for example, light-emitting devices from which light of white (W), yellow (Y), magenta (M), cyan (C), and the like is obtained may be formed. For example, when the light-emitting devices from which light of some of the above colors is obtained are added to the light-emitting devices from which light of three kinds of colors (R, G, and B) is obtained, effects such as an improvement in color purity and a reduction in power consumption can be obtained. Alternatively, a light-emitting apparatus that is capable of full-color display may be fabricated by a combination with color filters. As the kinds of color filters, red (R), green (G), blue (B), cyan (C), magenta (M), and yellow (Y) color filters and the like can be used.

When the second substrate 306 and the first substrate 301 are bonded to each other with the sealant 305, the FETs (309, 310, 311, and 312) and the light-emitting device 317 over the first substrate 301 are provided in a space 318 surrounded by the first substrate 301, the second substrate 306, and the sealant 305. Note that the space 318 may be filled with an inert gas (e.g., nitrogen or argon) or an organic substance (including the sealant 305).

An epoxy resin or glass frit can be used for the sealant 305. It is preferable to use a material that is permeable to as little moisture and oxygen as possible for the sealant 305. For the second substrate 306, a material that can be used for the first substrate 301 can be similarly used. Thus, any of the various substrates described in the other embodiments can be appropriately used. As the substrate, a glass substrate, a quartz substrate, or a plastic substrate made of FRP (Fiber-Reinforced Plastics), PVF (polyvinyl fluoride), polyester, an acrylic resin, or the like can be used. In the case where glass frit is used for the sealant, the first substrate 301 and the second substrate 306 are preferably glass substrates in terms of adhesion.

In the above manner, the active-matrix light-emitting apparatus can be obtained.

In the case where the active-matrix light-emitting apparatus is formed over a flexible substrate, the FETs and the light-emitting device may be directly formed over the flexible substrate; alternatively, the FETs and the light-emitting device may be formed over a substrate provided with a separation layer and then separated at the separation layer by application of heat, force, laser irradiation, or the like to be transferred to a flexible substrate. For the separation layer, a stack of inorganic films such as a tungsten film and a silicon oxide film, or an organic resin film of polyimide or the like can be used, for example. Examples of the flexible substrate include, in addition to a substrate over which a transistor can be formed, a paper substrate, a cellophane substrate, an aramid film substrate, a polyimide film substrate, a cloth substrate (including a natural fiber (e.g., silk, cotton, or hemp), a synthetic fiber (e.g., nylon, polyurethane, or polyester), a regenerated fiber (e.g., acetate, cupro, rayon, or regenerated polyester), or the like), a leather substrate, and a rubber substrate. With the use of any of these substrates, high durability, high heat resistance, a reduction in weight, and a reduction in thickness can be achieved.

Note that the structures described in this embodiment can be used in an appropriate combination with the structures described in the other embodiments.

Embodiment 5

In this embodiment, examples of a variety of electronic devices and an automobile completed using the light-emitting device of one embodiment of the present invention or a light-emitting apparatus including the light-emitting device of one embodiment of the present invention will be described. Note that the light-emitting apparatus can be used mainly in a display portion of the electronic device described in this embodiment.

Electronic devices shown in FIG. 4A to FIG. 4E can include a housing 7000, a display portion 7001, a speaker 7003, an LED lamp 7004, operation keys 7005 (including a power switch or an operation switch), a connection terminal 7006, a sensor 7007 (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared ray), a microphone 7008, and the like.

Figure 4A:
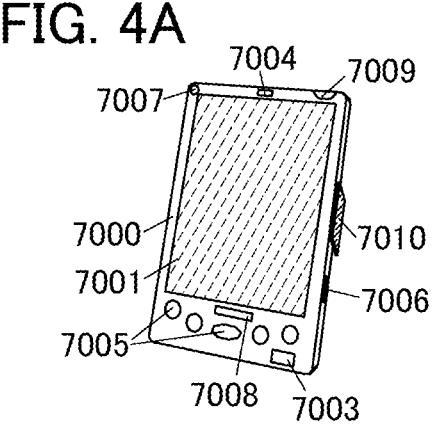
FIG. 4A is a diagram illustrating a mobile computer.

FIG. 4A is a mobile computer which can include a switch 7009, an infrared port 7010, and the like in addition to the above components.

Figure 4B:
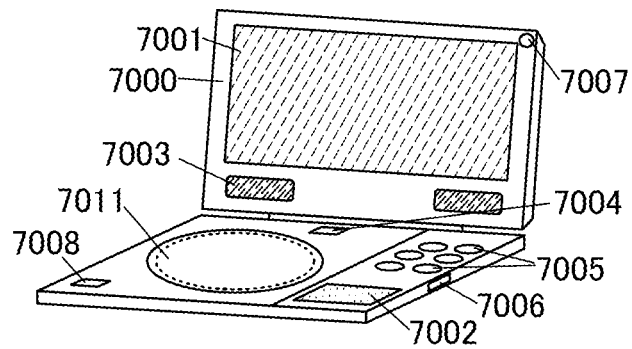
FIG. 4B is a diagram illustrating a portable image reproducing device.

FIG. 4B is a portable image reproducing device (e.g., a DVD player) which is provided with a recording medium and can include a second display portion 7002, a recording medium reading portion 7011, and the like in addition to the above components.

Figure 4C:
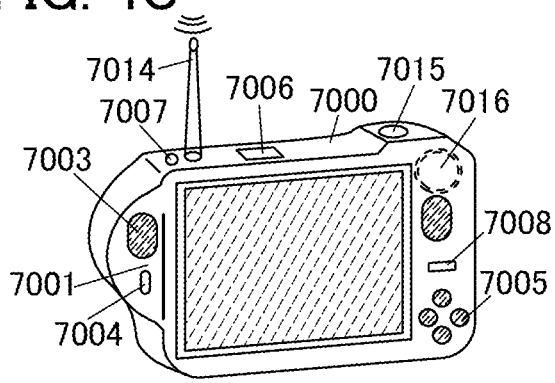
FIG. 4C is a diagram illustrating a digital camera.

FIG. 4C is a digital camera with a television reception function, which can include an antenna 7014, a shutter button 7015, an image receiving portion 7016, and the like in addition to the above components.

Figure 4D:
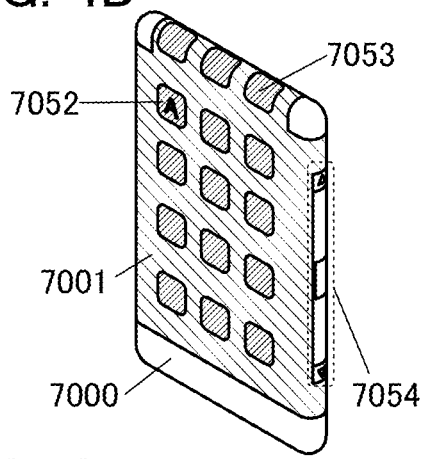
FIG. 4D is a diagram illustrating a portable information terminal.

FIG. 4D is a portable information terminal. The portable information terminal has a function of displaying information on three or more surfaces of the display portion 7001. Here, an example in which information 7052, information 7053, and information 7054 are displayed on different surfaces is shown. For example, the user can check the information 7053 displayed in a position that can be observed from above the portable information terminal, with the portable information terminal put in a breast pocket of his/her clothes. The user can see the display without taking out the portable information terminal from the pocket and decide whether to answer the call, for example.

Figure 4E:
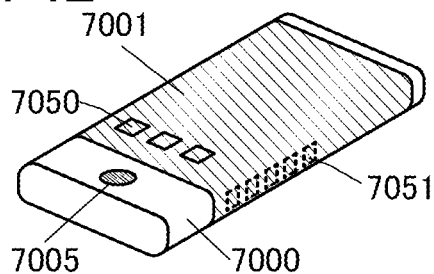
FIG. 4E is a diagram illustrating a portable information terminal.

FIG. 4E is a portable information terminal (e.g., a smartphone) and can include the display portion 7001, the operation key 7005, and the like in the housing 7000. Note that the speaker 7003, the connection terminal 7006, the sensor 7007, or the like may be provided in the portable information terminal. The portable information terminal can display characters and image information on its plurality of surfaces. Here, an example in which three icons 7050 are displayed is shown. Information 7051 indicated by dashed rectangles can be displayed on another surface of the display portion 7001. Examples of the information 7051 include notification of reception of an e-mail, SNS, or an incoming call, the title and sender of an e-mail, SNS, or the like, the date, the time, remaining battery, and the reception strength of an antenna. Alternatively, the icon 7050 or the like may be displayed in the position where the information 7051 is displayed.

Figure 4F:
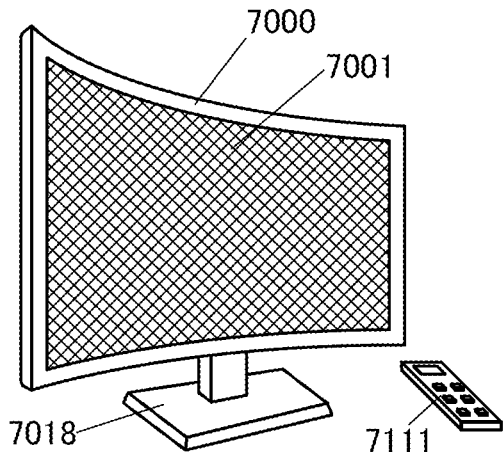
FIG. 4F is a diagram illustrating a television set.

FIG. 4F is a large-size television set (also referred to as TV or a television receiver), which can include the housing 7000, the display portion 7001, and the like. Shown here is a structure where the housing 7000 is supported by a stand 7018. The television set can be operated with a separate remote controller 7111 or the like. Note that the display portion 7001 may include a touch sensor, in which case the television set may be operated by touch on the display portion 7001 with a finger or the like. The remote controller 7111 may be provided with a display portion for displaying information output from the remote controller 7111. With operation keys or a touch panel provided in the remote controller 7111, channels and volume can be operated and images displayed on the display portion 7001 can be operated.

The electronic devices shown in FIG. 4A to FIG. 4F can have a variety of functions. For example, they can have a function of displaying a variety of information (e.g., a still image, a moving image, and a text image) on the display portion, a touch panel function, a function of displaying a calendar, date, time, or the like, a function of controlling processing with a variety of software (programs), a wireless communication function, a function of being connected to a variety of computer networks with a wireless communication function, a function of transmitting and receiving a variety of data with a wireless communication function, and a function of reading out a program or data stored in a recording medium and displaying it on the display portion. Furthermore, the electronic device including a plurality of display portions can have a function of displaying image information mainly on one display portion while displaying text information mainly on another display portion, a function of displaying a three-dimensional image by displaying images on a plurality of display portions with a parallax taken into account, or the like. Furthermore, the electronic device including an image receiving portion can have a function of taking a still image, a function of taking a moving image, a function of automatically or manually correcting a taken image, a function of storing a taken image in a recording medium (an external recording medium or a recording medium incorporated in the camera), a function of displaying a taken image on the display portion, or the like. Note that functions that the electronic devices shown in FIG. 4A to FIG. 4F can have are not limited to those, and the electronic devices can have a variety of functions.

Figure 4G:
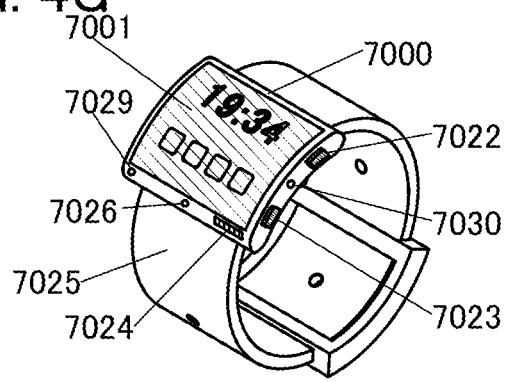
FIG. 4G is a diagram illustrating a portable information terminal.

FIG. 4G is a watch-type portable information terminal, which can be used as a smart watch, for example. The watch-type portable information terminal includes the housing 7000, the display portion 7001, operation buttons 7022 and 7023, a connection terminal 7024, a band 7025, a microphone 7026, a sensor 7029, a speaker 7030, and the like. The display surface of the display portion 7001 is bent, and display can be performed along the bent display surface.

Furthermore, mutual communication between the portable information terminal and, for example, a headset capable of wireless communication can be performed, allowing hands-free calling. With the connection terminal 7024, the portable information terminal can perform mutual data transmission with another information terminal and charging. Wireless power feeding can also be employed for the charging operation.

The display portion 7001 mounted in the housing 7000 also serving as a bezel includes a non-rectangular display region. The display portion 7001 can display an icon indicating time, another icon, and the like. The display portion 7001 may be a touch panel (an input/output device) including a touch sensor (an input device).

Note that the smart watch shown in FIG. 4G can have a variety of functions. For example, the smart watch can have a function of displaying a variety of information (e.g., a still image, a moving image, and a text image) on the display portion, a touch panel function, a function of displaying a calendar, date, time, or the like, a function of controlling processing with a variety of software (programs), a wireless communication function, a function of being connected to a variety of computer networks with a wireless communication function, a function of transmitting and receiving a variety of data with a wireless communication function, and a function of reading out a program or data stored in a recording medium and displaying it on the display portion.

Moreover, a speaker, a sensor (a sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), a microphone, and the like can be included inside the housing 7000.

Note that the light-emitting apparatus of one embodiment of the present invention and the display device including the light-emitting device of one embodiment of the present invention can be used in the display portions of the electronic devices described in this embodiment, enabling the electronic devices to have a long lifetime.

Figure 5A:
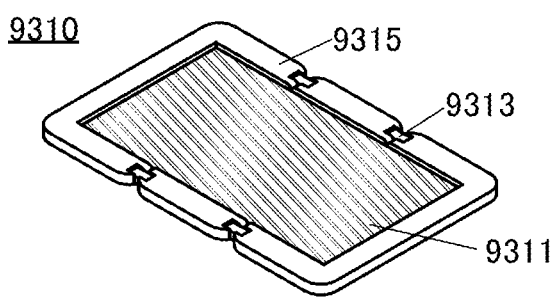
FIG. 5A is a diagram illustrating an electronic device.
Figure 5B:
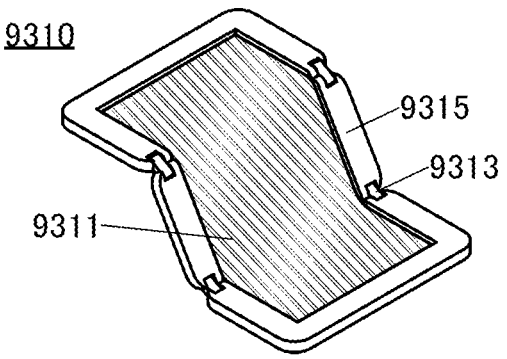
FIG. 5B is a diagram illustrating the electronic device.
Figure 5C:
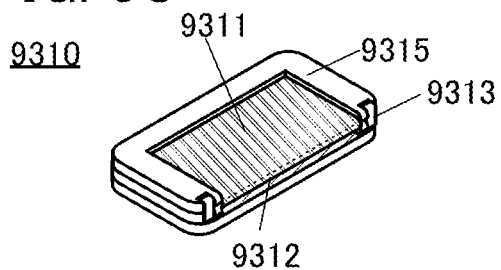
FIG. 5C is a diagram illustrating the electronic device.

Another electronic device including the light-emitting apparatus is a foldable portable information terminal shown in FIG. 5A to FIG. 5C. FIG. 5A shows a portable information terminal 9310 which is opened. FIG. 5B shows the portable information terminal 9310 in a state in the middle of change from one of an opened state and a folded state to the other. FIG. 5C shows the portable information terminal 9310 which is folded. The portable information terminal 9310 is excellent in portability when folded, and is excellent in display browsability when opened because of a seamless large display region.

A display portion 9311 is supported by three housings 9315 joined together by hinges 9313. Note that the display portion 9311 may be a touch panel (an input/output device) including a touch sensor (an input device). By bending the display portion 9311 at a portion between two housings 9315 with the use of the hinges 9313, the portable information terminal 9310 can be reversibly changed in shape from an opened state to a folded state. The light-emitting apparatus of one embodiment of the present invention can be used for the display portion 9311. An electronic device having a long lifetime can be achieved. A display region 9312 in the display portion 9311 is a display region that is positioned at a side surface of the portable information terminal 9310 which is folded. On the display region 9312, information icons, file shortcuts of frequently used applications or programs, and the like can be displayed, allowing confirmation of information and start of an application to be smoothly performed.

Figure 6A:
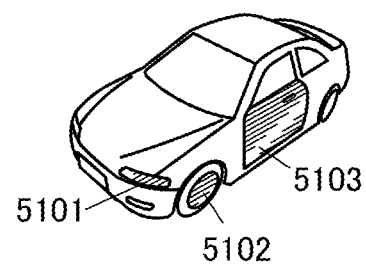
FIG. 6A is a diagram illustrating an automobile.
Figure 6B:
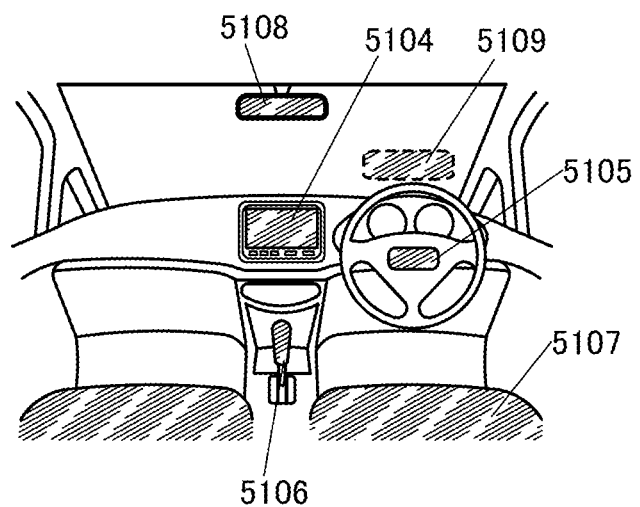
FIG. 6B is a diagram illustrating the automobile.

FIG. 6A and FIG. 6B show an automobile including the light-emitting apparatus. That is, the light-emitting apparatus can be integrated into an automobile. Specifically, the light-emitting apparatus can be used in lights 5101 (including lights of the rear part of the car), a tire wheel 5102, a part or the whole of a door 5103, or the like on the outer side of the automobile shown in FIG. 6A. The light-emitting apparatus can also be used in a display portion 5104, a steering wheel 5105, a shifter 5106, a seat 5107, an inner rearview mirror 5108, or the like on the inner side of the automobile shown in FIG. 6B. Apart from that, the light-emitting apparatus may be used in a part of glass window 5109.

In the above manner, the electronic devices and automobiles in which the light-emitting apparatus or the display device of one embodiment of the present invention is used can be obtained. In that case, a long-lifetime electronic device can be achieved. Note that the light-emitting apparatus or the display device can be used for electronic devices and automobiles in a variety of fields without being limited to those described in this embodiment.

Note that the structures described in this embodiment can be used in an appropriate combination with any of the structures described in the other embodiments.

Embodiment 6

In this embodiment, a structure of a lighting device fabricated using the light-emitting apparatus of one embodiment of the present invention or the light-emitting device which is part of the light-emitting apparatus will be described with reference to FIG. 7.

Figure 7A:
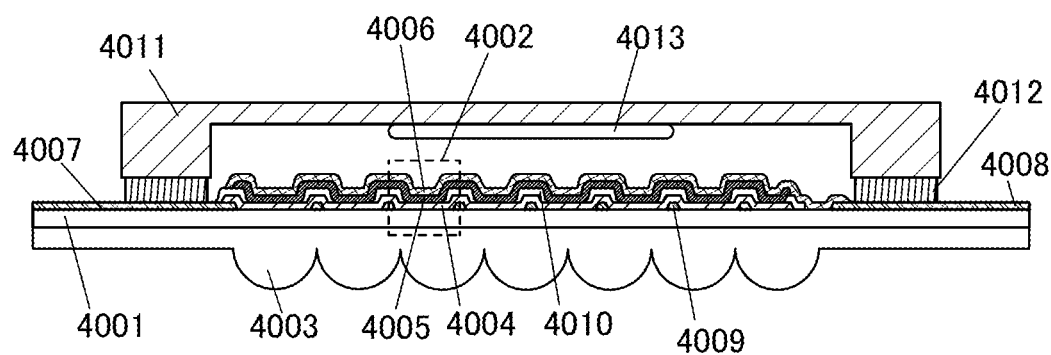
FIG. 7A is a diagram illustrating a lighting device.
Figure 7B:
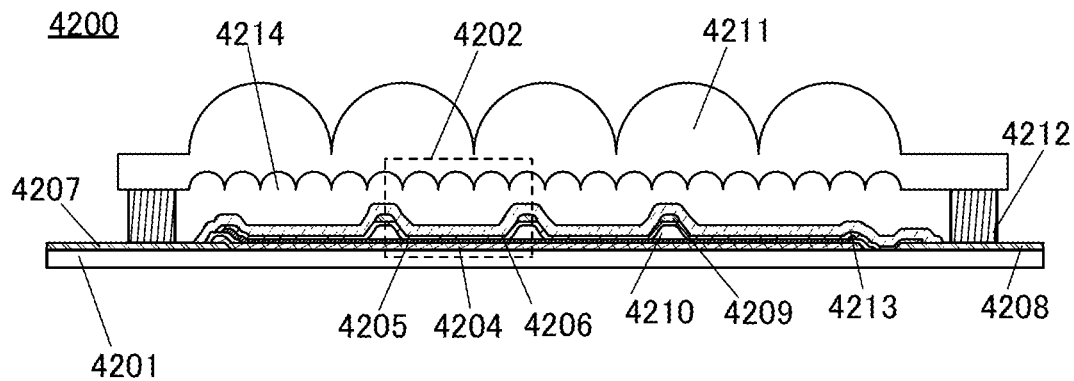
FIG. 7B is a diagram illustrating a lighting device.

FIG. 7A and FIG. 7B show examples of cross-sectional views of lighting devices. FIG. 7A is a bottom-emission lighting device in which light is extracted from the substrate side, and FIG. 7B is a top-emission lighting device in which light is extracted from the sealing substrate side.

A lighting device 4000 shown in FIG. 7A includes a light-emitting device 4002 over a substrate 4001. In addition, the lighting device 4000 includes a substrate 4003 with unevenness on the outside of the substrate 4001. The light-emitting device 4002 includes a first electrode 4004, an EL layer 4005, and a second electrode 4006.

The first electrode 4004 is electrically connected to an electrode 4007, and the second electrode 4006 is electrically connected to an electrode 4008. In addition, an auxiliary wiring 4009 electrically connected to the first electrode 4004 may be provided. Note that an insulating layer 4010 is formed over the auxiliary wiring 4009.

The substrate 4001 and a sealing substrate 4011 are bonded to each other with a sealant 4012. A desiccant 4013 is preferably provided between the sealing substrate 4011 and the light-emitting device 4002. The substrate 4003 has the unevenness shown in FIG. 7A, which increases the extraction efficiency of light generated in the light-emitting device 4002.

A lighting device 4200 shown in FIG. 7B includes a light-emitting device 4202 over a substrate 4201. The light-emitting device 4202 includes a first electrode 4204, an EL layer 4205, and a second electrode 4206.

The first electrode 4204 is electrically connected to an electrode 4207, and the second electrode 4206 is electrically connected to an electrode 4208. An auxiliary wiring 4209 electrically connected to the second electrode 4206 may also be provided. In addition, an insulating layer 4210 may be provided under the auxiliary wiring 4209.

The substrate 4201 and a sealing substrate 4211 with unevenness are bonded to each other with a sealant 4212. A barrier film 4213 and a planarization film 4214 may be provided between the sealing substrate 4211 and the light-emitting device 4202. The sealing substrate 4211 has the unevenness shown in FIG. 7B, whereby the extraction efficiency of light generated in the light-emitting device 4202 can be increased.

Application examples of such lighting devices include a ceiling light for indoor lighting. Examples of the ceiling light include a ceiling direct mount light and a ceiling embedded light. Such a lighting device is fabricated using the light-emitting apparatus and a housing or a cover in combination.

For another example, such lighting devices can be used for a foot light that illuminates a floor so as to improve safety on the floor. For example, the foot light can be effectively used in a bedroom, on a staircase, or on a passage. In that case, the size or shape of the foot light can be changed depending on the area or structure of a room. The foot light can be a stationary lighting device fabricated using the light-emitting apparatus and a support base in combination.

Such lighting devices can also be used for a sheet-like lighting device (sheet-like lighting). The sheet-like lighting, which is attached to a wall when used, is space-saving and thus can be used for a wide variety of uses. Furthermore, the area of the sheet-like lighting can be easily increased. The sheet-like lighting can also be used on a wall or housing having a curved surface.

Besides the above examples, the light-emitting apparatus which is one embodiment of the present invention or the light-emitting device which is a part of the light-emitting apparatus can be used as part of furniture in a room, so that a lighting device which has a function of the furniture can be obtained.

As described above, a variety of lighting devices that include the light-emitting apparatus can be obtained. Note that these lighting devices are also embodiments of the present invention.

The structures described in this embodiment can be used in an appropriate combination with the structures described in the other embodiments.

Example 1

Synthesis Example 1

In this example, a synthesis method of 8-(2-naphthyl)-4-phenyl-2-(9'-phenyl-3,3'-bi-9H-carbazol-9-yl)-[1]benzofuro[3,2-d]pyrimidine (abbreviation: 4Ph-8βN-2PCCzBfpm), which is an organic compound of one embodiment of the present invention represented by Structural Formula (100) in Embodiment 1, will be described. Note that the structure of 4Ph-8βN-2PCCzBfpm is shown below.

[Chemical Formula 17]

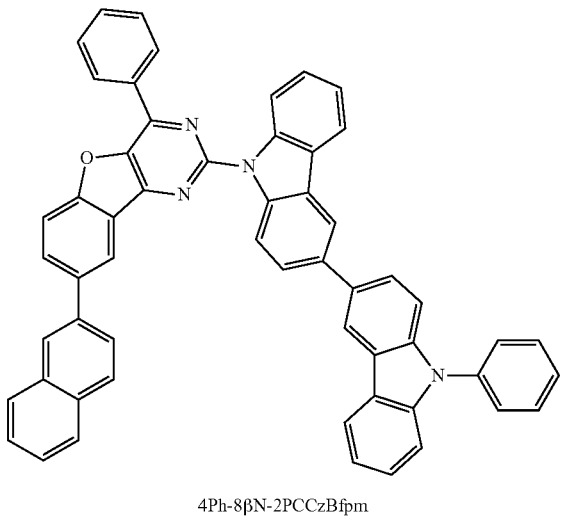

4Ph-8βN-2PCCzBfpm

Step 1; Synthesis of 2,8-dichloro-4-phenyl[1]benzofuro[3,2-d]pyrimidine

First, 10 g (37 mmol) of 2,4,8-trichloro[1]benzofuro[3,2-d]pyrimidine, 4.5 g (371 mmol) of phenylboronic acid, 37 mL of a 2M aqueous solution of potassium carbonate, 180 mL of toluene, and 18 mL of ethanol were put into a 500 mL three-neck flask; then, the flask was degassed and the air in the flask was replaced with nitrogen. To this mixture, 1.3 g (1.8 mmol) of bis(triphenylphosphine)palladium(II) dichloride was added, followed by stirring at 80° C. for 16 hours.

After a predetermined time elapsed, the obtained reaction mixture was concentrated, water was added, and the mixture was suction-filtered. The obtained residue was washed with ethanol to give a solid. The solid was dissolved in heated toluene, followed by suction filtration through a filter medium in which Celite, alumina, and Celite were stacked in this order. The obtained filtrate was concentrated to give 11 g of a target white solid in a yield of 91%. The synthesis scheme in Step 1 is shown in Formula (a-1) below.

[Chemical Formula 18]

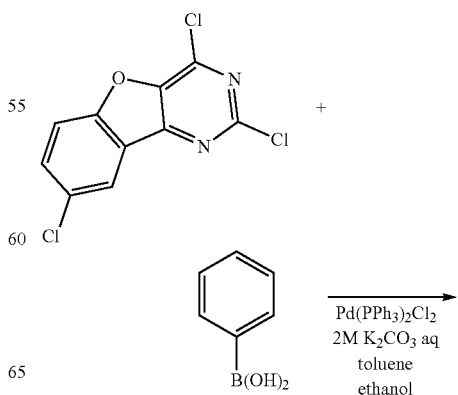

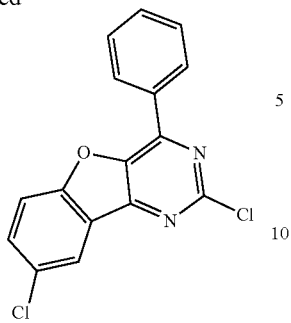

Step 2; Synthesis of 8-chloro-4-phenyl-2-(9'-phenyl-3,3'-bi-9H-carbazol-9-yl)-[1]benzofuro[3,2-d]pyrimidine Next, 5.0 g (16 mmol) of 2,8-dichloro-4-phenyl[1]benzofuro[3,2-d]pyrimidine, which was obtained in Step 1, 6.5 g (16 mmol) of 9-phenyl-3,3'-bi-9H-carbazole, 3.1 g (32 mmol) of tert-sodium butoxide, and 150 mL of xylene were put into a 300 mL three-neck flask; then, the air in the flask was replaced with nitrogen. Then, 224 mg (0.64 mmol) of di-tert-butyl(1-methyl-2,2-diphenylcyclopropyl)phosphine (abbreviation: cBRIDP) and 58 mg (0.16 mmol) of allylpalladium(II)chloride dimer were added thereto, and the mixture was heated and stirred at 90° C. for 7 hours.

Water was added to the obtained reaction mixture, and an aqueous layer was subjected to extraction with toluene. The obtained solution of the extract and an organic layer were combined and washed with saturated saline, and anhydrous magnesium sulfate was added to the organic layer for drying. The obtained mixture was gravity-filtered and the filtrate was concentrated to give a solid. This solid was purified by silica gel column chromatography. As a developing solvent, a mixed solvent of toluene:hexane=1:1 was used. The obtained fraction was concentrated to give 5.5 g of a target yellow solid in a yield of 50%. The synthesis scheme in Step 2 is shown in Formula (a-2) below.

[Chemical Formula 19]

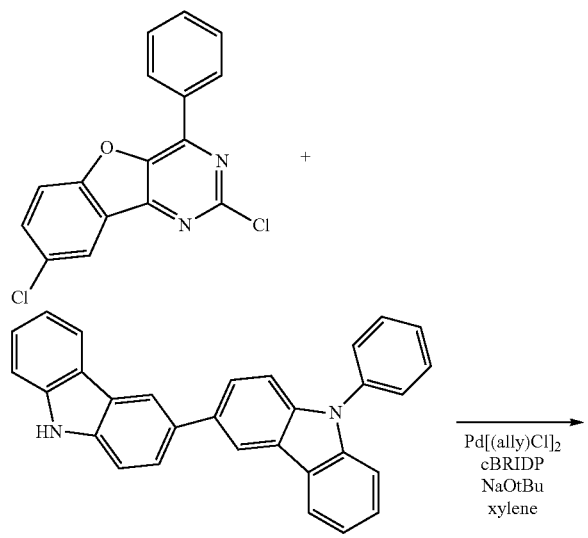

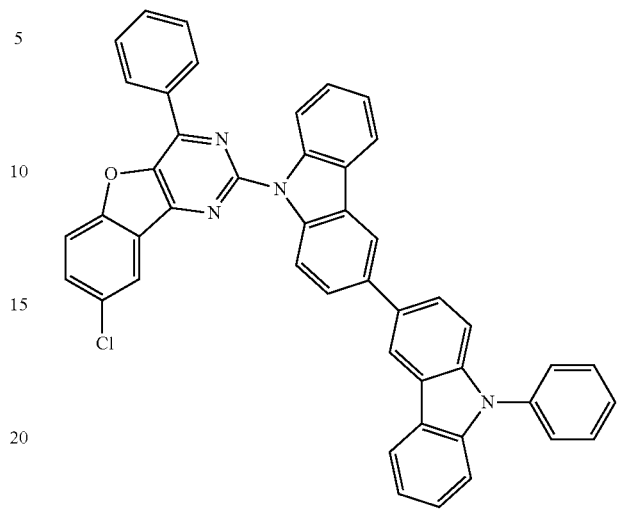

(a-2)

Step 3; Synthesis of 4Ph-8βN-2PCCzBfpm

Next, 2.3 g (3.3 mmol) of 8-chloro-4-phenyl-2-(9'-phenyl-3,3'-bi-9H-carbazol-9-yl)-[1]benzofuro[3,2-d]pyrimidine, which was obtained in Step 2 above, 0.62 g (3.6 mmol) of 2-naphthylboronic acid, 1.5 g (9.81 mmol) of cesium fluoride, and 35 mL of xylene were put into a three-neck flask; then, the air in the flask was replaced with nitrogen.

The temperature of this mixture was raised to 60° C., 60 mg (0.065 mmol) of tris(dibenzylideneacetone)dipalladium (0) and 79 mg (0.2 mmol) of 2'-(dicyclohexylphosphino) acetophenone ethylene ketal were added thereto, and the mixture was heated and stirred at 100° C. for 13.5 hours. Furthermore, 30 mg (0.032 mmol) of tris(dibenzylideneacetone)dipalladium(0) and 39 mg (0.095 mmol) of 2'-(dicyclohexylphosphino)acetophenone ethylene ketal were added thereto, and the mixture was heated and stirred at 110° C. for 7 hours and then at 120° C. for 7 hours.

Water was added to the resulting solid, followed by suction filtration, and the residue was washed with ethanol. The solid was dissolved in heated toluene, followed by suction filtration through a filter medium in which Celite, alumina, and Celite were stacked in this order. The obtained filtrate was concentrated to give 1.84 g of a yellow solid in a yield of 74%. The synthesis scheme in Step 3 is shown in Formula (a-3) below.

[Chemical Formula 20]

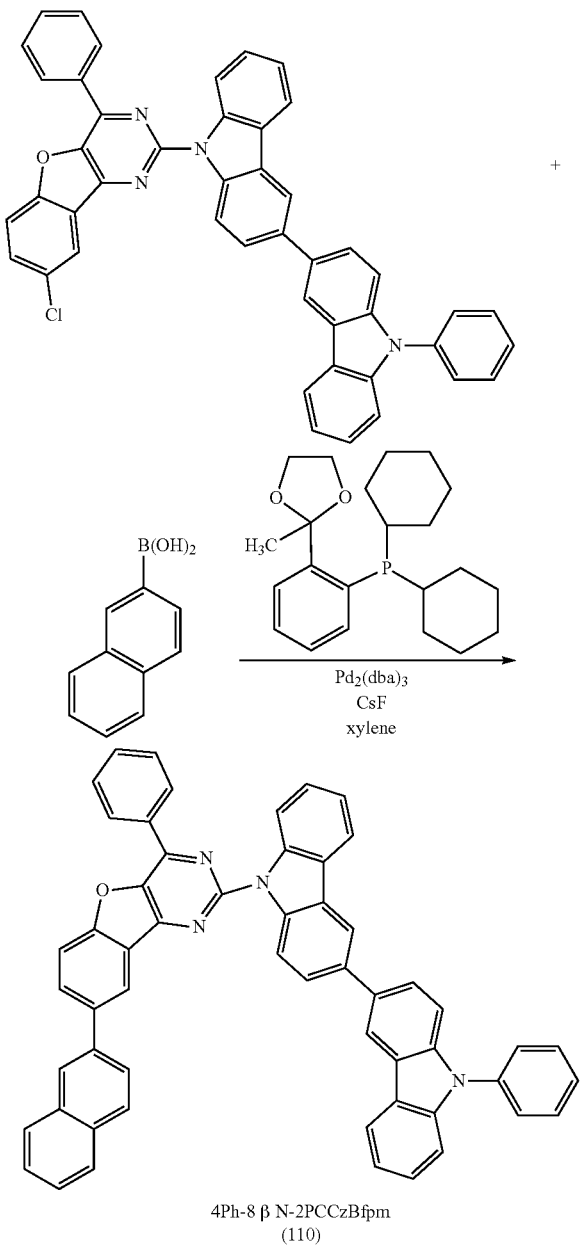

By a train sublimation method, 0.99 g of the obtained yellow solid was sublimated and purified. The conditions of the sublimation purification were such that the solid was heated at a pressure of 1×10⁻² Pa and a temperature of 380° C. After the sublimation purification, 0.72 g of a target yellow solid was obtained at a collection rate of 72%. Furthermore, 0.72 g of the yellow solid was sublimated and purified by a train sublimation method. The sublimation purification was performed under the conditions of a pressure of 2.36 Pa and a heating temperature of 385° C. After the sublimation purification, 0.58 g of a target yellow solid was obtained at a collection rate of 85%.

Figure 8:
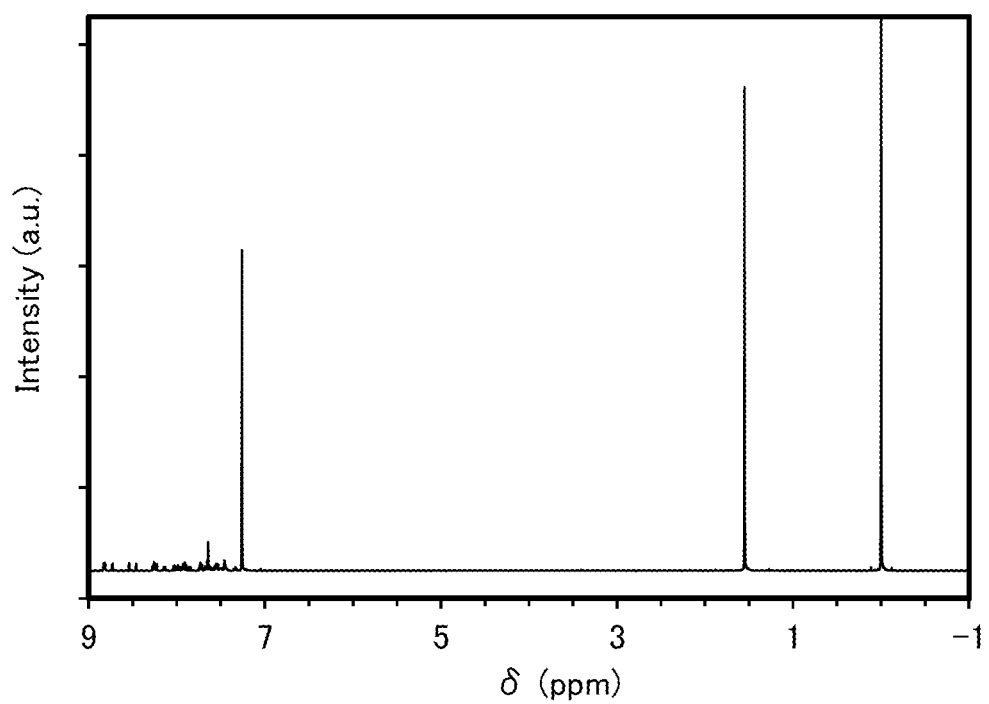
FIG. 8 is a $^1$H-NMR chart of an organic compound represented by Structural Formula (100).

The following shows analysis results by nuclear magnetic resonance (¹H-NMR) spectroscopy of the yellow solid obtained in Step 3 above. FIG. 8 shows a ¹H-NMR chart. The results reveal that 4Ph-8βN-2PCCzBfpm, the organic compound of one embodiment of the present invention represented by Structural Formula (100) above, was obtained in this example.

¹H-NMR. δ (CDCl₃): 7.34 (t, 1H), 7.44-7.69 (m, 13H), 7.73 (t, 2H), 7.86 (dd, 1H), 7.89-8.04 (m, 6H), 8.14 (dd, 1H), 8.23 (s, 1H), 8.26 (t, 2H), 8.46 (d, 1H), 8.54 (d, 1H), 8.73 (d, 1H), 8.82 (d, 2H), 9.01 (d, 1H), 9.06 (d, 1H).

<<Physical Properties of 4Ph-8βN-2PCCzBfpm>>

Next, the ultraviolet-visible absorption spectrum (hereinafter, simply referred to as "absorption spectrum") and emission spectrum of a toluene solution of 4Ph-8βN-2PCCzBfpm were measured.

Figure 9:
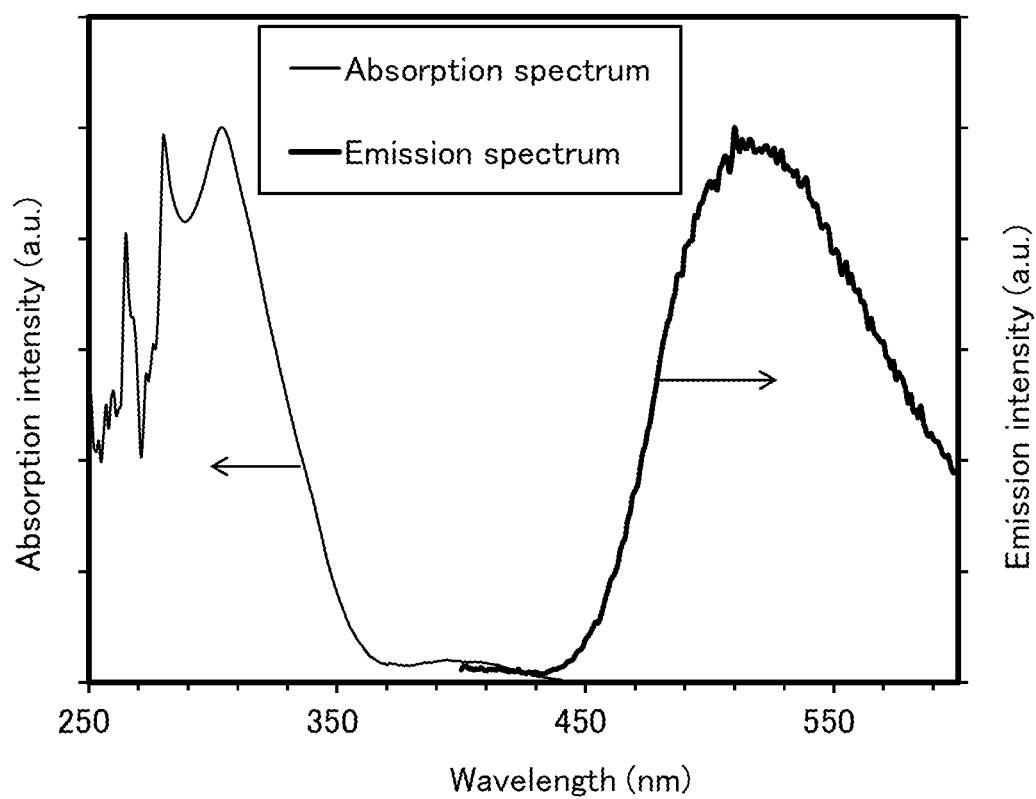
FIG. 9 shows the ultraviolet-visible absorption spectrum and the emission spectrum of the organic compound represented by Structural Formula (100).

The absorption spectrum was measured with an ultraviolet-visible spectrophotometer (V550, manufactured by JASCO Corporation). The emission spectrum was measured with a fluorescence spectrophotometer (FS920, manufactured by Hamamatsu Photonics K.K.). FIG. 9 shows the obtained measurement results of the absorption spectrum and the emission spectrum of the toluene solution. The horizontal axis represents wavelength and the vertical axis represents absorption intensity.

The results in FIG. 9 show that the toluene solution of 4Ph-8βN-2PCCzBfpm exhibited absorption peaks at around 394 nm and 304 nm, and an emission wavelength peak at around 510 nm (excitation wavelength: 345 nm).

Figure 10:
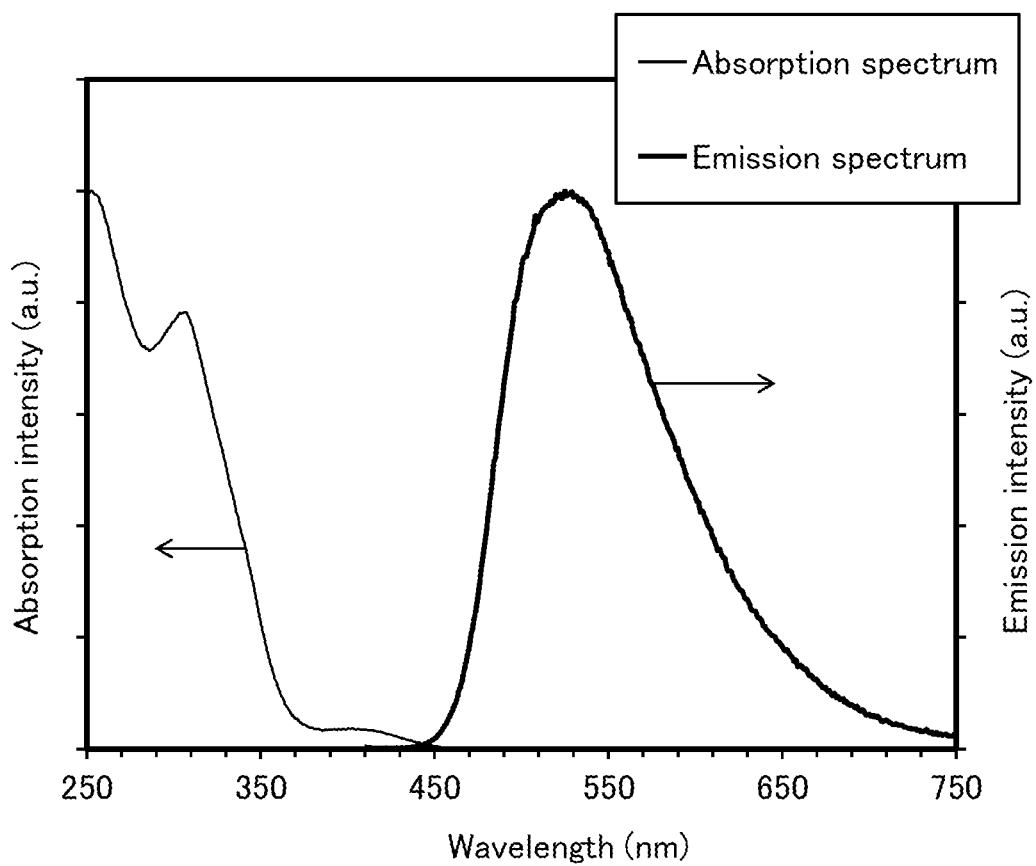
FIG. 10 shows the ultraviolet-visible absorption spectrum and the emission spectrum of the organic compound represented by Structural Formula (100).

Next, the absorption spectrum and emission spectrum of a solid thin film of 4Ph-8βN-2PCCzBfpm were measured. In the measurement of the absorption spectrum of the solid thin film, the solid thin film formed on a quartz substrate by a vacuum evaporation method was used and measurement was performed with an ultraviolet-visible spectrophotometer (U-4100, manufactured by Hitachi High-Technologies Corporation). In the measurement of the emission spectrum of the solid thin film, the solid thin film similar to the above was used and measurement was performed with a fluorescence spectrophotometer (FS920, manufactured by Hamamatsu Photonics K.K.). FIG. 10 shows the obtained measurement results of the absorption spectrum and emission spectrum of the solid thin film. The horizontal axis represents wavelength and the vertical axes represent absorption intensity and emission intensity.

FIG. 10 shows that the solid thin film of 4Ph-8βN-2PCCzBfpm exhibited absorption peaks at around 401 nm and 307 nm and an emission wavelength peak at around 525 nm (excitation wavelength: 400 nm).

It was found that 4Ph-8βN-2PCCzBfpm, which is the organic compound of one embodiment of the present invention, has a high T1 level and is a host material suitable for a phosphorescent material (a guest material) that emits light in the vicinity of green to red regions. Note that 4Ph-8βN-2PCCzBfpm, which is the organic compound of one embodiment of the present invention, can also be used as a host material for a substance that emits phosphorescence in the visible region or a light-emitting substance.

Example 2

Synthesis Example 2

In this example, a synthesis method of 8-(dibenzothiophen-4-yl)-4-phenyl-2-(9'-phenyl-3,3'-bi-9H-carbazol-9-yl)-[1]benzofuro[3,2-d]pyrimidine (abbreviation: 4Ph-8DBt-2PCCzBfpm), which is an organic compound of one embodiment of the present invention represented by Structural Formula (101) in Embodiment 1, will be described. Note that the structure of 4Ph-8DBt-2PCCzBfpm is shown below.

[Chemical Formula 21]

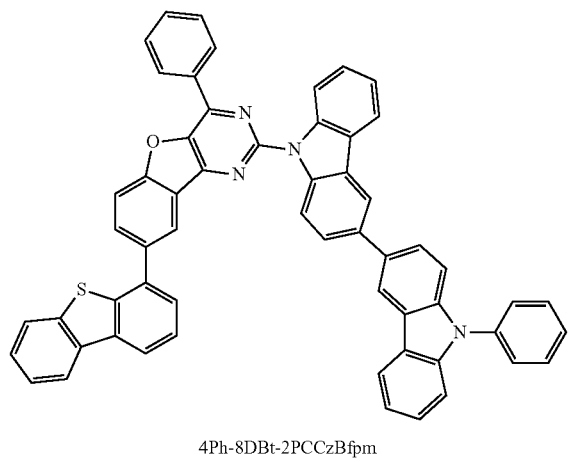

4Ph-8DBt-2PCCzBfpm

<Synthesis of 4Ph-8DBt-2PCCzBfpm>

First, 2.25 g (3.3 mmol) of 8-chloro-4-phenyl-2-(9'-phenyl-3,3'-bi-9H-carbazol-9-yl)[1]benzofuro[3,2-d]pyrimidine, which was obtained in Step 2 in Example 1, 0.82 g (3.6 mmol) of 4-dibenzothiopheneboronic acid, 1.5 g (9.8 mmol) of cesium fluoride, and 35 mL of xylene were put into a three-neck flask; then, the air in the flask was replaced with nitrogen.

The temperature of this mixture was raised to 60° C., 60 mg (0.065 mmol) of tris(dibenzylideneacetone)dipalladium (0) and 77 mg (0.2 mmol) of 2'-(dicyclohexylphosphino)acetophenone ethylene ketal were added thereto, and the mixture was heated and stirred at 100° C. for 16 hours. Furthermore, 30 mg (0.032 mmol) of tris(dibenzylideneacetone)dipalladium(0) and 36 mg (0.1 mmol) of 2'-(dicyclohexylphosphino)acetophenone ethylene ketal were added thereto, and the mixture was heated and stirred at 110° C. for 7 hours and then at 120° C. for 7 hours.

Water was added to the obtained reaction product, followed by suction filtration, and the residue was washed with ethanol. The solid was dissolved in toluene, followed by suction filtration through a filter medium in which Celite, alumina, and Celite were stacked in this order. The obtained filtrate was concentrated and recrystallized with toluene to give 1.87 g of a target yellow solid in a yield of 68%. The synthesis scheme is shown in Formula (b-1) below.

[Chemical Formula 22]

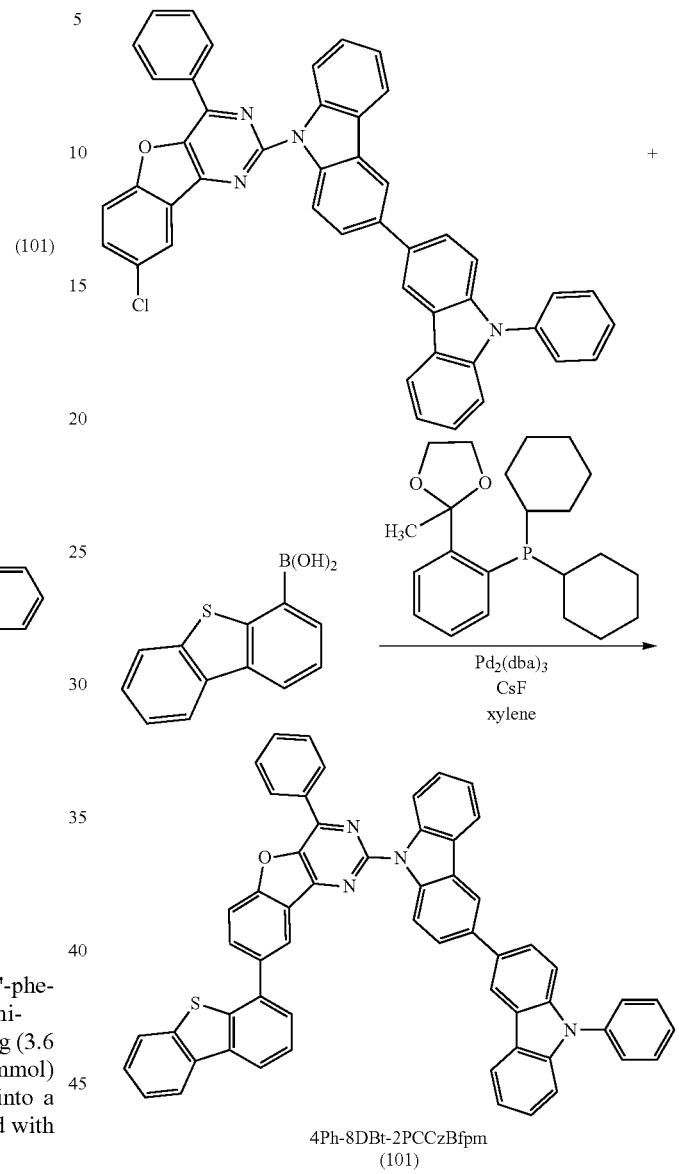

4Ph-8DBt-2PCCzBfpm
(101)

By a train sublimation method, 0.90 g of the obtained yellow solid was sublimated and purified. The conditions of the sublimation purification were such that the solid was heated at a pressure of $1.58 \times 10^{-2}$ Pa and a temperature of 400° C. After the sublimation purification, 0.78 g of a target yellow solid was obtained at a collection rate of 86%.

Figure 11:
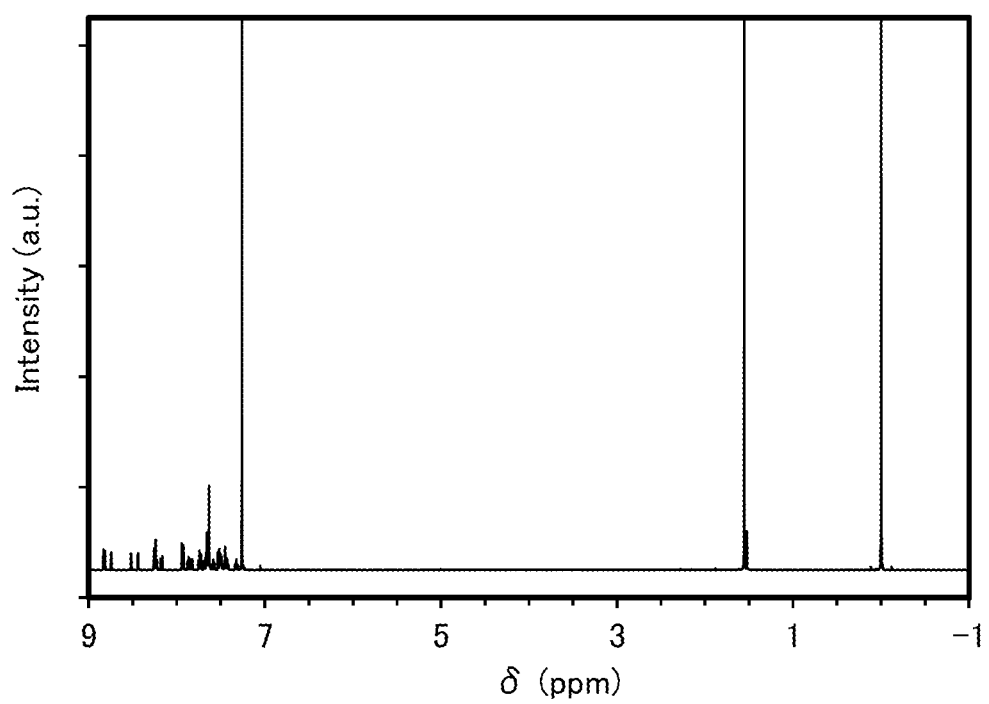
FIG. 11 is a $^1$H-NMR chart of an organic compound represented by Structural Formula (101).

The following shows analysis results by nuclear magnetic resonance ($^1$H-NMR) spectroscopy of the yellow solid obtained in the above reaction. FIG. 11 shows a $^1$H-NMR chart. The results reveal that 4Ph-8DBt-2PCCzBfpm, the organic compound of one embodiment of the present invention represented by Structural Formula (101) above, was obtained in this example.

$^1$H-NMR. δ (CDCl$_3$): 7.33 (t, 1H), 7.41-7.53 (m, 7H), 7.59 (t, 1H), 7.62-7.70 (m, 7H), 7.72-7.75 (m, 2H), 7.83 (dd, 1H), 7.87 (dd, 1H), 7.93-7.95 (m, 2H), 8.17 (dd, 1H), 8.23-8.26 (m, 4H), 8.44 (d, 1H), 8.52 (d, 1H), 8.75 (d, 1H), 8.2 (d, 2H), 9.02 (d, 1H), 9.07 (d, 1H).

<<Physical Properties of 4Ph-8DBt-2PCCzBfpm>>

Next, the ultraviolet-visible absorption spectrum (hereinafter, simply referred to as "absorption spectrum") and emission spectrum of a toluene solution of 4Ph-8DBt-2PCCzBfpm were measured.

Figure 12:
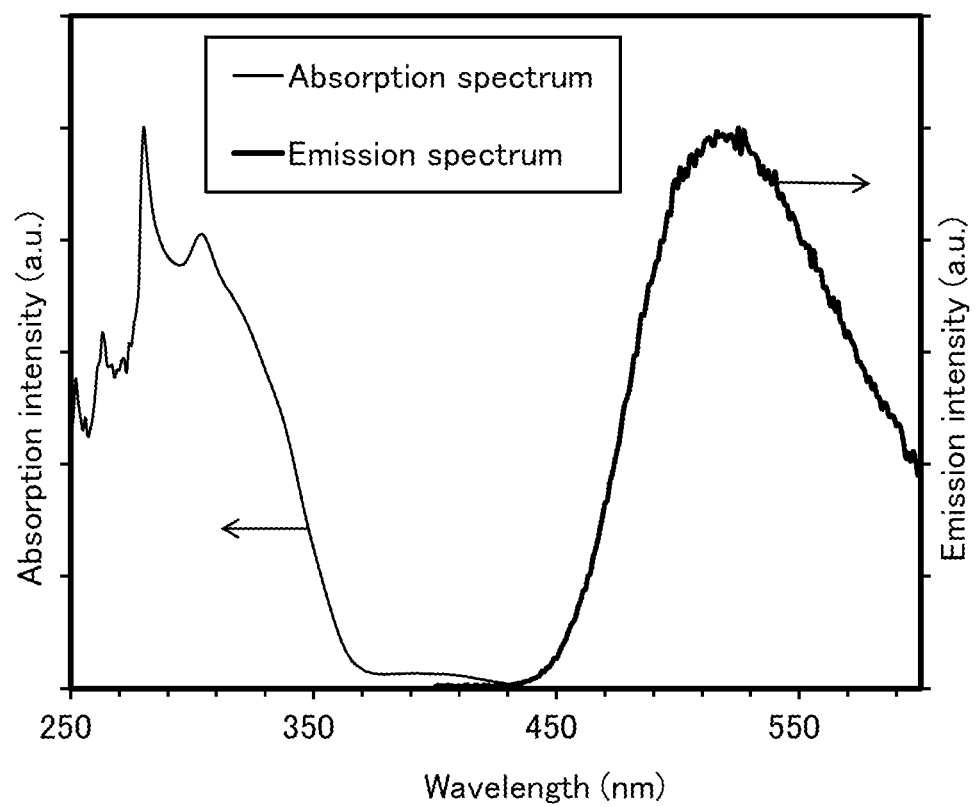
FIG. 12 shows the ultraviolet-visible absorption spectrum and the emission spectrum of the organic compound represented by Structural Formula (101).

The absorption spectrum was measured with an ultraviolet-visible spectrophotometer (V550, manufactured by JASCO Corporation). The emission spectrum was measured with a fluorescence spectrophotometer (FS920, manufactured by Hamamatsu Photonics K.K.). FIG. 12 shows the obtained measurement results of the absorption spectrum and the emission spectrum of the toluene solution. The horizontal axis represents wavelength and the vertical axis represents absorption intensity.

The results in FIG. 12 show that the toluene solution of 4Ph-8DBt-2PCCzBfpm exhibited absorption peaks at around 403 nm and 304 nm, and an emission wavelength peak at around 525 nm (excitation wavelength: 345 nm).

Figure 13:
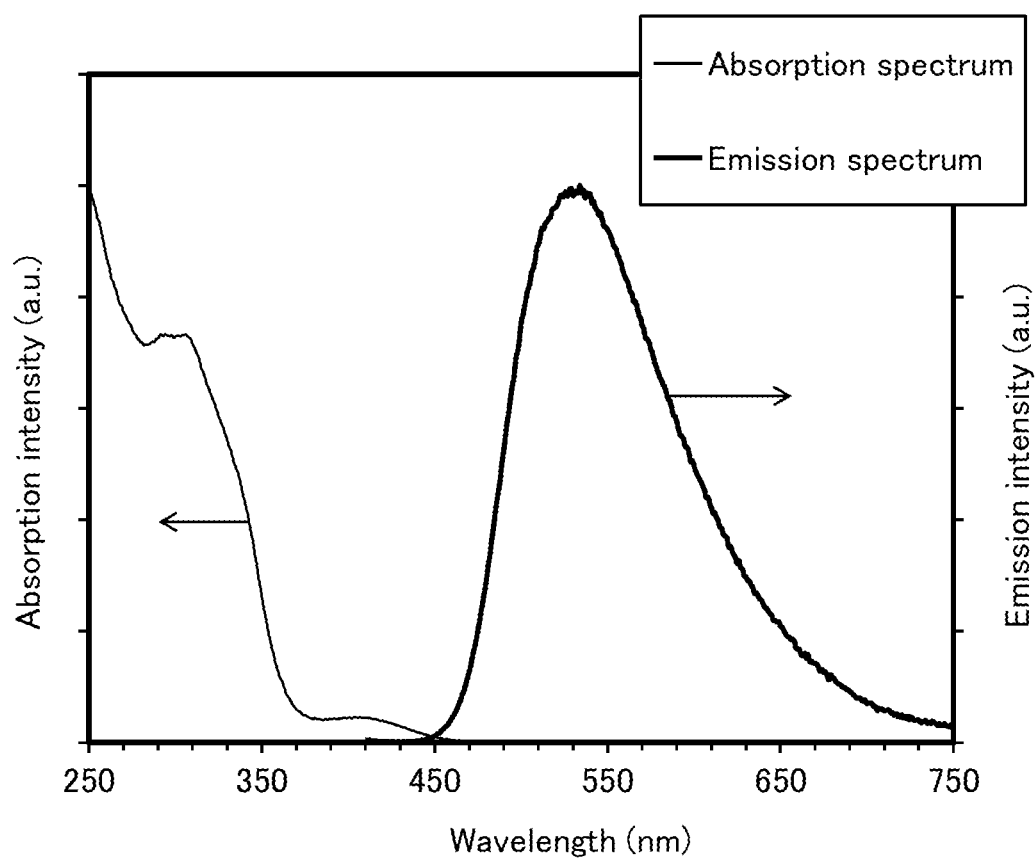
FIG. 13 shows the ultraviolet-visible absorption spectrum and the emission spectrum of the organic compound represented by Structural Formula (101).

Next, the absorption spectrum and emission spectrum of a solid thin film of 4Ph-8DBt-2PCCzBfpm were measured. In the measurement of the absorption spectrum of the solid thin film, the solid thin film formed on a quartz substrate by a vacuum evaporation method was used and measurement was performed with an ultraviolet-visible spectrophotometer (U-4100, manufactured by Hitachi High-Technologies Corporation). In the measurement of the emission spectrum of the solid thin film, the solid thin film similar to the above was used and measurement was performed with a fluorescence spectrophotometer (FS920, manufactured by Hamamatsu Photonics K.K.). FIG. 13 shows the obtained measurement results of the absorption spectrum and emission spectrum of the solid thin film. The horizontal axis represents wavelength and the vertical axes represent absorption intensity and emission intensity.

FIG. 13 shows that the solid thin film of 4Ph-8DBt-2PCCzBfpm exhibited absorption peaks at around 404 nm and 308 nm and an emission wavelength peak at around 534 nm (excitation wavelength: 400 nm).

It is found that 4Ph-8DBt-2PCCzBfpm, which is the organic compound of one embodiment of the present invention, has a high T1 level and is a host material suitable for a phosphorescent material (a guest material) that emits light in the vicinity of green to red regions. Note that 4Ph-8DBt-2PCCzBfpm, which is the organic compound of one embodiment of the present invention, can also be used as a host material for a substance that emits phosphorescence in the visible region or a light-emitting substance.

Example 3

Figure 14:
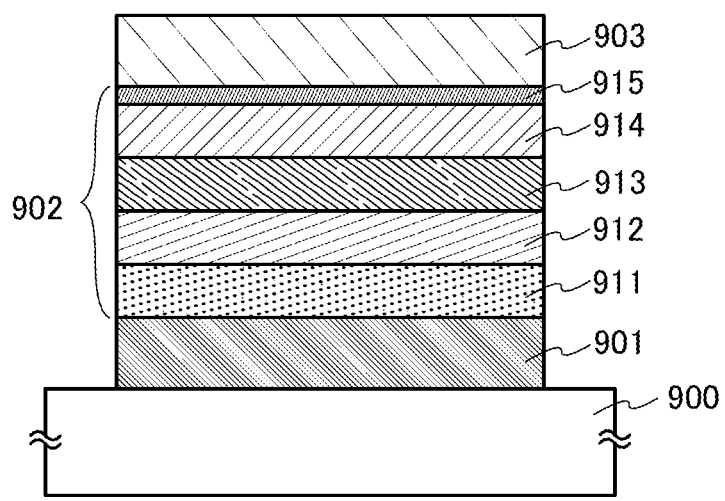
FIG. 14 is a diagram illustrating a light-emitting device.

Described in this example are the device structures, fabrication methods, and characteristics of a light-emitting device 1 as one embodiment of the present invention, which uses in a light-emitting layer 8-(2-naphthyl)-4-phenyl-2-(9'-phenyl-3,3'-bi-9H-carbazol-9-yl)-[1]benzofuro[3,2-d]pyrimidine (abbreviation: 4Ph-8βN-2PCCzBfpm) (Structural Formula (100)) described in Example 1 and bis[2-(2-pyridinyl-κN²)phenyl-κC][2-(4-phenyl-2-pyridinyl-κN²)phenyl-κC]iridium(III) (abbreviation: [Ir(ppy)₂(4dppy)]) as a guest material (a phosphorescent material), a light-emitting device 2 as one embodiment of the present invention, which uses in a light-emitting layer 8-(dibenzothiophen-4-yl)-4-phenyl-2-(9'-phenyl-3,3'-bi-9H-carbazol-9-yl)-[1]benzofuro[3,2-d]pyrimidine (abbreviation: 4Ph-8DBt-2PCCzBfpm) (Structural Formula (101)) described in Example 2 and [Ir(ppy)₂(4dppy)]) as a guest material, and a comparative light-emitting device 3 used for comparison, which uses in a light-emitting layer 4-phenyl-2-(9'-phenyl-3,3'-bi-9H-carbazol-9-yl)benzofuro[3,2-d]pyrimidine (abbreviation: 4Ph-2PCCzBfpm) and [Ir(ppy)₂(4dppy)]) as a guest material. FIG. 14 shows the device structure of the light-emitting devices used in this example, and Table 1 shows specific compositions. The chemical formulae of the materials used in this example are shown below.

TABLE 1

| | First electrode | Hole-injection layer | Hole-transport layer | Light-emitting layer | Electron-transport layer | Electron-injection layer | Second electrode |
| --- | --- | --- | --- | --- | --- | --- | --- |
| Light-emitting device 1 | ITSO (70 nm) | DBT3P-II:MoOx (2:1 50 nm) | PCBBiIBP (20 nm) | * | 4Ph-8βN-2PCCzBfpm (20 nm) | NBphen (15 nm) | LiF (1 nm) Al (200 nm) |
| Light-emitting device 2 | ITSO (70 nm) | DBT3P-II:MoOx (2:1 50 nm) | PCBBiIBP (20 nm) | ** | 4Ph-8DBt-2PCCzBfpm (20 nm) | NBphen (15 nm) | LiF (1 nm) Al (200 nm) |
| Comparative light-emitting device 3 | ITSO (70 nm) | DBT3P-II:MoOx (2:1 50 nm) | PCBBiIBP (20 nm) | *** | 4Ph-2PCCzBfpm (20 nm) | NBphen (15 nm) | LiF (1 nm) Al (200 nm) |

* 4Ph-8βN-2PCCzBfpm:[Ir(ppy)₂(4dppy)] (1:0.1 40 nm)
** 4Ph-8DBt-2PCCzBfpm:[Ir(ppy)₂(4dppy)] (1:0.1 40 nm)
*** 4Ph-2PCCzBfpm:[Ir(ppy)₂(4dppy)] (1:0.1 40 nm)

[Chemical Formula 23]

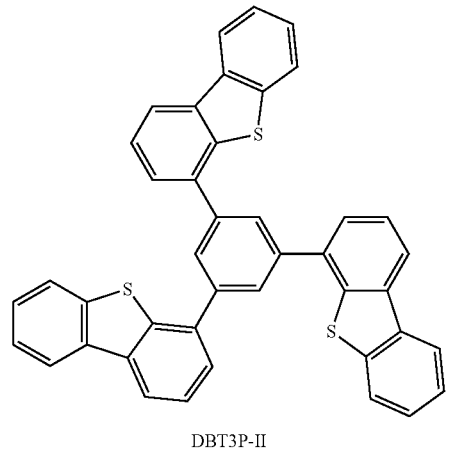

DBT3P-II

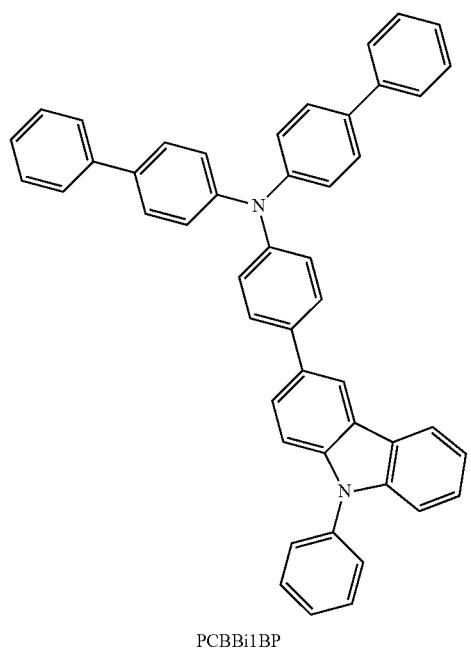
PCBBi1BP
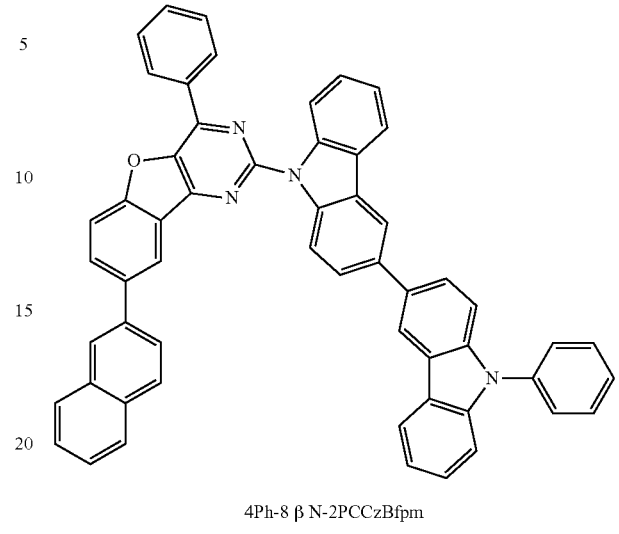
(100)
4Ph-8βN-2PCCzBfpm
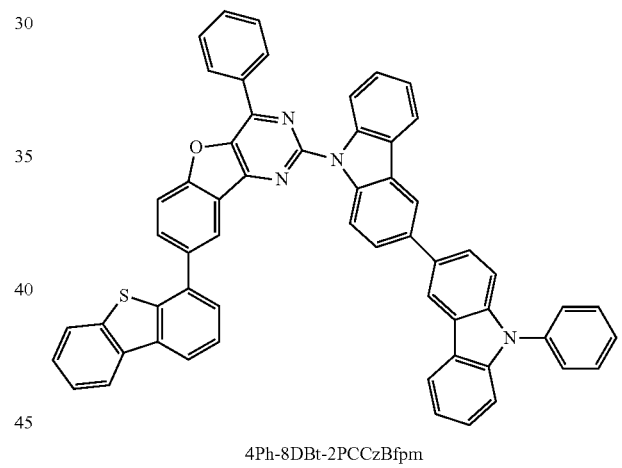
(101)
4Ph-8DBt-2PCCzBfpm
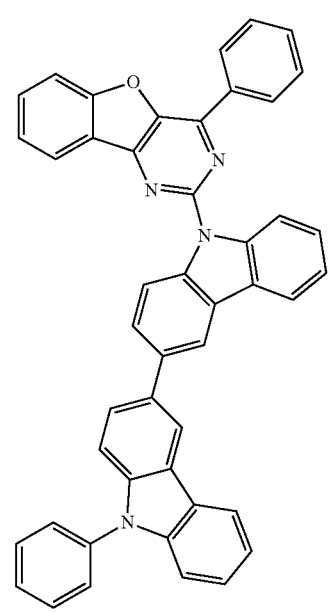
4Ph-2PCCzBfpm
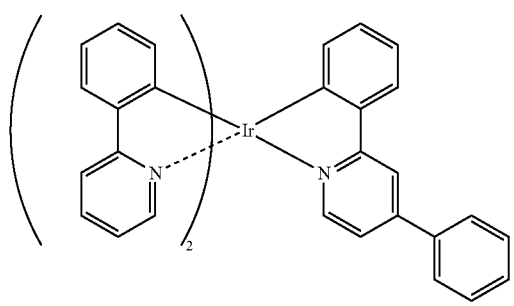
[Ir(ppy)₂(4dppy)]

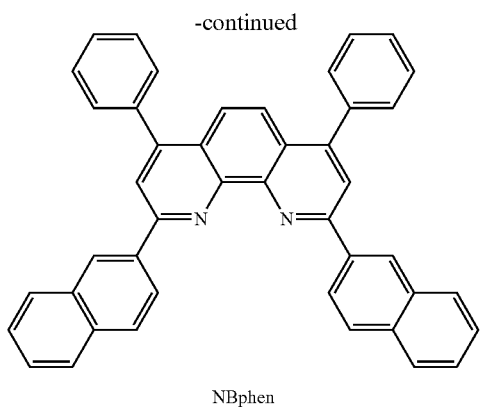

NBphen

<<Fabrication of Light-Emitting Devices>>

The light-emitting devices described in this example each have a structure shown in FIG. 14, in which a hole-injection layer 911, a hole-transport layer 912, a light-emitting layer 913, an electron-transport layer 914, and an electron-injection layer 915 are stacked in this order over a first electrode 901 formed over a substrate 900, and a second electrode 903 is stacked over the electron-injection layer 915.

First, the first electrode 901 was formed over the substrate 900. The electrode area was set to 4 mm$^2$ (2 mm×2 mm). A glass substrate was used as the substrate 900. The first electrode 901 was formed to a thickness of 70 nm using indium tin oxide containing silicon oxide (ITSO) by a sputtering method.

As pretreatment, a surface of the substrate was washed with water, baking was performed at 200° C. for 1 hour, and then UV ozone treatment was performed for 370 seconds. After that, the substrate was transferred into a vacuum evaporation apparatus in which the pressure was reduced to about 1×10$^{-4}$ Pa, vacuum baking at 170° C. for 30 minutes was performed in a heating chamber in the vacuum evaporation apparatus, and then the substrate was naturally cooled down for about 30 minutes.

Next, the hole-injection layer 911 was formed over the first electrode 901. For the formation of the hole-injection layer 911, the pressure in the vacuum evaporation apparatus was reduced to 1×10$^{-4}$ Pa, and then 4,4',4''-(benzene-1,3,5-triyl)tri(dibenzothiophene) (abbreviation: DBT3P-II) and molybdenum oxide were co-evaporated such that DBT3P-II: molybdenum oxide was 2:1 (mass ratio) and the thickness was 50 nm.

Then, the hole-transport layer 912 was formed over the hole-injection layer 911. The hole-transport layer 912 was formed to a thickness of 20 nm by evaporation using 4,4'-diphenyl-4''-(9-phenyl-9H-carbazol-3-yl)triphenylamine (abbreviation: PCBBi1BP).

Next, the light-emitting layer 913 was formed over the hole-transport layer 912.

For the light-emitting layer 913 in the light-emitting device 1, co-evaporation using bis[2-(2-pyridinyl-N$^2$)phenyl-κC][2-(4-phenyl-2-pyridinyl-κN$^2$)phenyl-κC]iridium (III) (abbreviation: [Ir(ppy)$_2$(4dppy)]) as a guest material (a phosphorescent material) in addition to 4Ph-8βN-2PCCzBfpm was performed such that the weight ratio was 4Ph-8βN-2PCCzBfpm: [Ir(ppy)$_2$(4dppy)]=1:0.1. The thickness was set to 40 nm. For the light-emitting device 2, co-evaporation using [Ir(ppy)$_2$(4dppy)] as a guest material (a phosphorescent material) in addition to 4Ph-8DBt-2PCCzBfpm was performed such that the weight ratio was 4Ph-8DBt-2PCCzBfpm: [Ir(ppy)$_2$(4dppy)]=1:0.1. The thickness was set to 40 nm. For the comparative light-emitting device 3, co-evaporation using [Ir(ppy)$_2$(4dppy)] as a guest material (a phosphorescent material) in addition to 4Ph-2PCCzBfpm was performed such that the weight ratio was 4Ph-2PCCzBfpm: [Ir(ppy)$_2$(4dppy)]=1:0.1. The thickness was set to 40 nm.

Next, the electron-transport layer 914 was formed over the light-emitting layer 913.

The electron-transport layer 914 in the light-emitting device 1 was formed in the following manner: 4Ph-8βN-2PCCzBfpm and 2,9-bis(naphthalen-2-yl)-4,7-diphenyl-1,10-phenanthroline (abbreviation: NBphen) were sequentially deposited by evaporation to thicknesses of 20 nm and 15 nm, respectively. The electron-transport layer 914 in the light-emitting device 2 was formed in the following manner: 4Ph-8DBt-2PCCzBfpm and NBphen were sequentially deposited by evaporation to thicknesses of 20 nm and 15 nm, respectively. The electron-transport layer 914 in the comparative light-emitting device 3 was formed in the following manner: 4Ph-2PCCzBfpm and NBphen were sequentially deposited by evaporation to thicknesses of 20 nm and 15 nm, respectively.

Then, the electron-injection layer 915 was formed over the electron-transport layer 914. The electron-injection layer 915 was formed to a thickness of 1 nm by evaporation using lithium fluoride (LiF).

After that, the second electrode 903 was formed over the electron-injection layer 915. The second electrode 903 was formed to a thickness of 200 nm by an evaporation method using aluminum. In this example, the second electrode 903 functions as a cathode.

Through the above steps, the light-emitting devices in each of which an EL layer was provided between a pair of electrodes over the substrate 900 were formed. The hole-injection layer 911, the hole-transport layer 912, the light-emitting layer 913, the electron-transport layer 914, and the electron-injection layer 915 described in the above steps are functional layers forming the EL layer in one embodiment of the present invention. Furthermore, in all the evaporation steps in the above fabrication method, an evaporation method by a resistance-heating method was used.

The light-emitting devices fabricated as described above are sealed using a different substrate (not shown). At the time of the sealing using the different substrate (not shown), the different substrate (not shown) coated with a sealant that solidifies by ultraviolet light was fixed onto the substrate 900 in a glove box containing a nitrogen atmosphere, and the substrates were bonded to each other such that the sealant would be attached to the periphery of the light-emitting device formed over the substrate 900. At the time of the sealing, the sealant was irradiated with 365-nm ultraviolet light at 6 J/cm$^2$ to be solidified, and the sealant was subjected to heat treatment at 80° C. for 1 hour to be stabilized.

<<Operation Characteristics of Light-Emitting Devices>>

Figure 15:
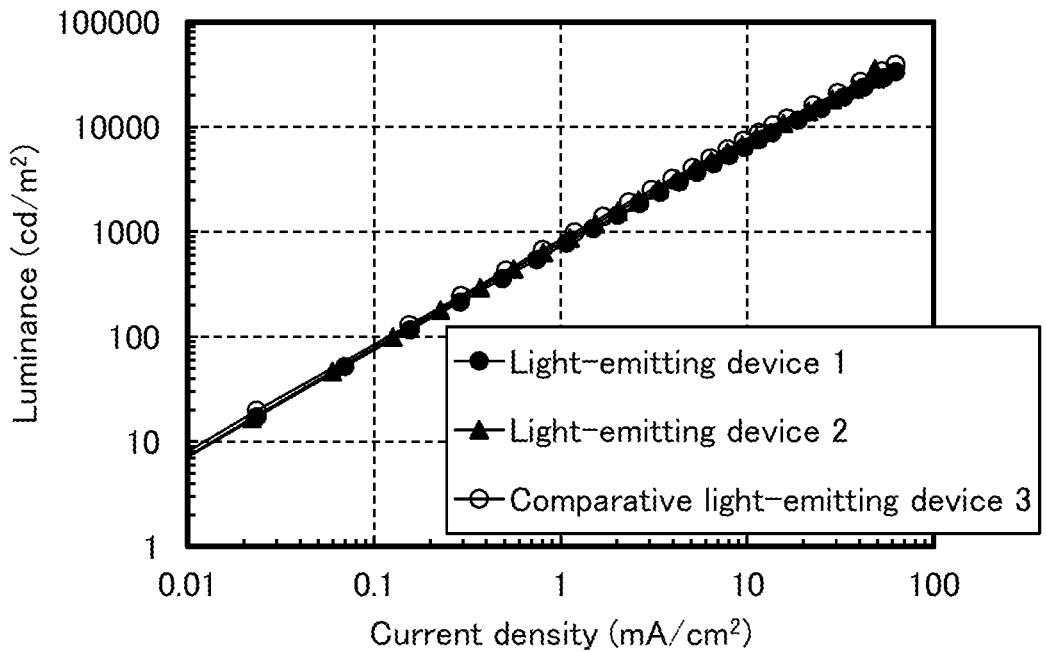
FIG. 15 is a graph showing the current density-luminance characteristics of a light-emitting device 1, a light-emitting device 2, and a comparative light-emitting device 3.
Figure 16:
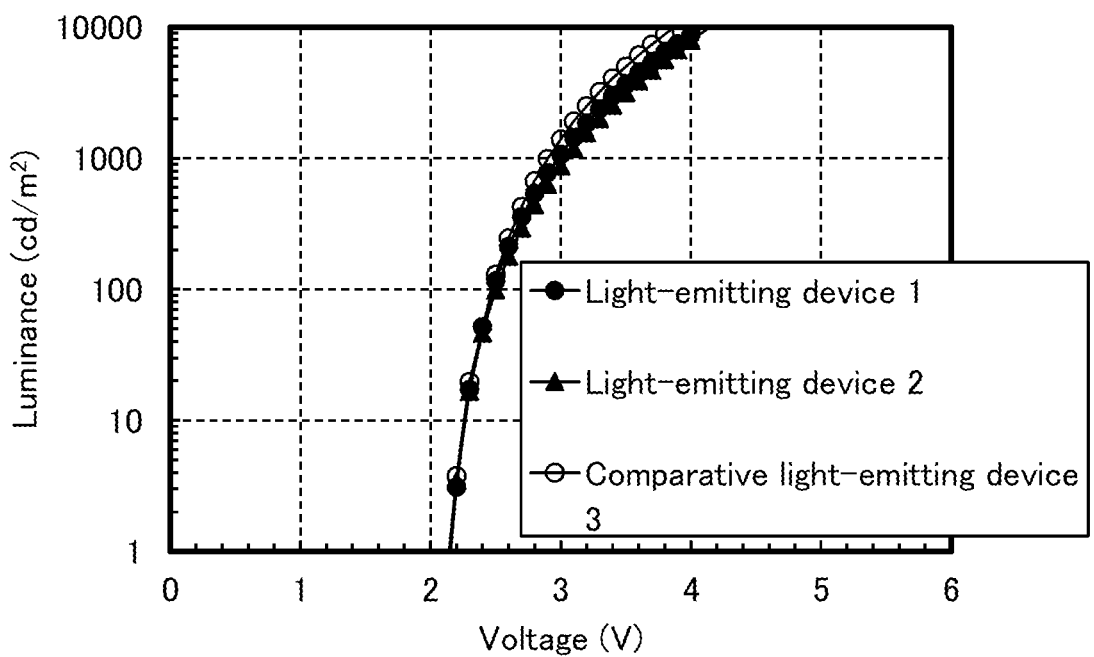
FIG. 16 is a graph showing the voltage-luminance characteristics of the light-emitting device 1, the light-emitting device 2, and the comparative light-emitting device 3.
Figure 17:
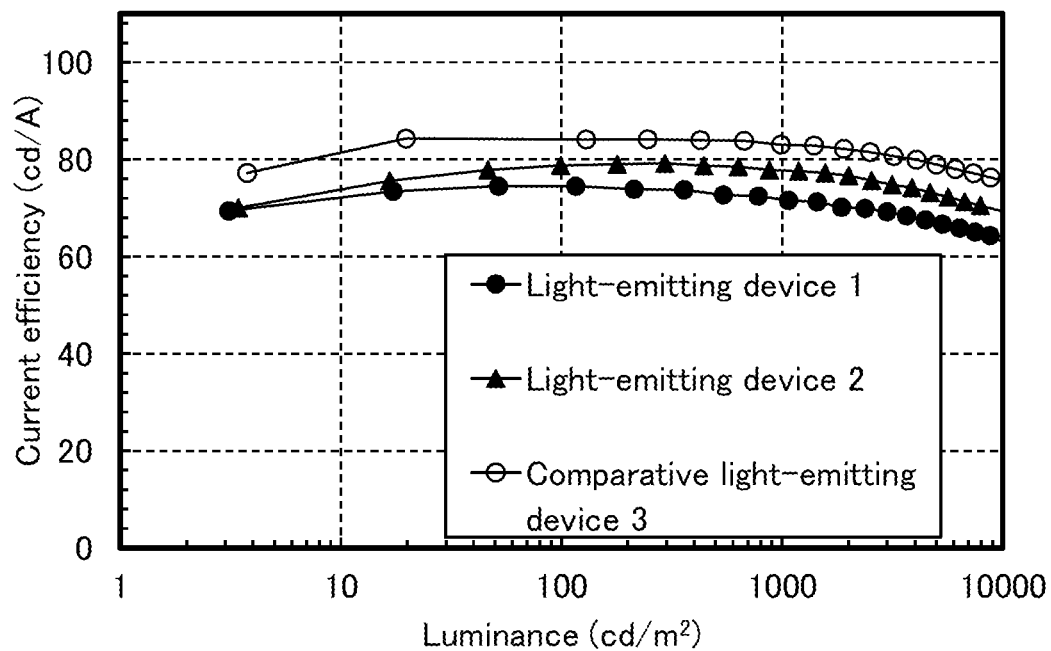
FIG. 17 is a graph showing the luminance-current efficiency characteristics of the light-emitting device 1, the light-emitting device 2, and the comparative light-emitting device 3.
Figure 18:
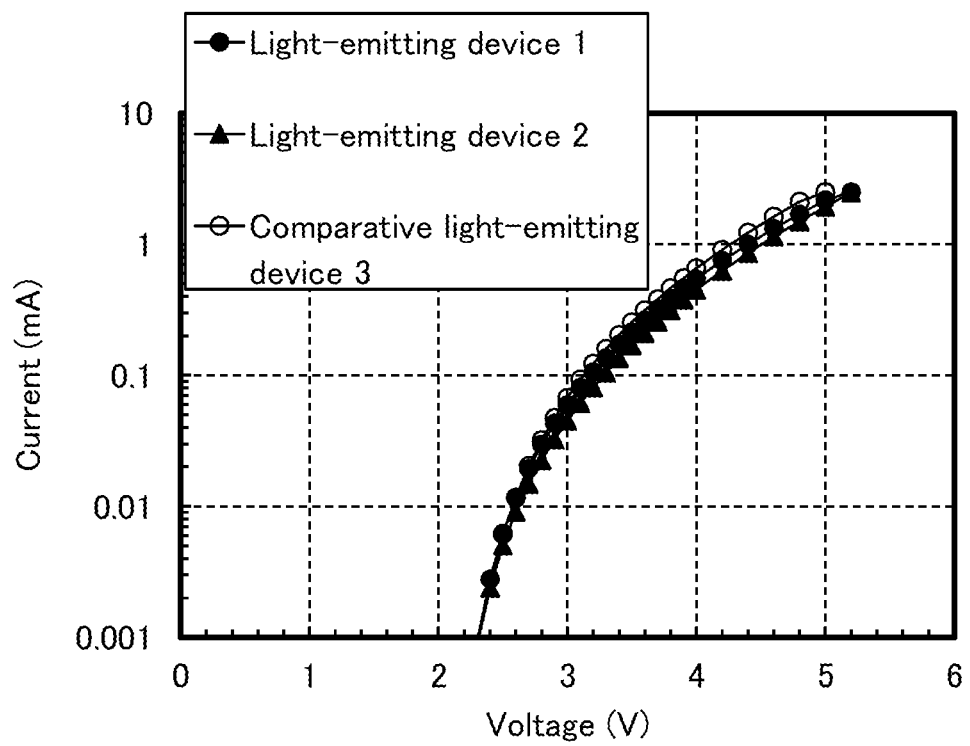
FIG. 18 is a graph showing the voltage-current characteristics of the light-emitting device 1, the light-emitting device 2, and the comparative light-emitting device 3.

Operation characteristics of each of the fabricated light-emitting devices were measured. Note that the measurement was carried out at room temperature (in an atmosphere maintained at 25° C.). As the results of the operation characteristics of the light-emitting devices, the current density-luminance characteristics are shown in FIG. 15, the voltage-luminance characteristics are shown in FIG. 16, the luminance-current efficiency characteristics are shown in FIG. 17, and the voltage-current characteristics are shown in FIG. 18.

Table 2 below shows the initial values of the main characteristics of each of the light-emitting devices at around 1000 cd/m$^2$.

TABLE 2

| | Voltage (V) | Current (mA) | Current density (mA/cm$^2$) | Chromaticity (x, y) | Luminance (cd/m$^2$) | Current efficiency (cd/A) | Power efficiency (lm/W) | External quantum efficiency (%) |
|---|---|---|---|---|---|---|---|---|
| Light-emitting device 1 | 3.0 | 0.060 | 1.5 | (0.47, 0.52) | 1100 | 72 | 75 | 23 |
| Light-emitting device 2 | 3.0 | 0.045 | 1.1 | (0.46, 0.53) | 880 | 78 | 82 | 24 |
| Comparative light-emitting device 3 | 2.9 | 0.048 | 1.2 | (0.45, 0.54) | 990 | 83 | 90 | 25 |

Figure 19:
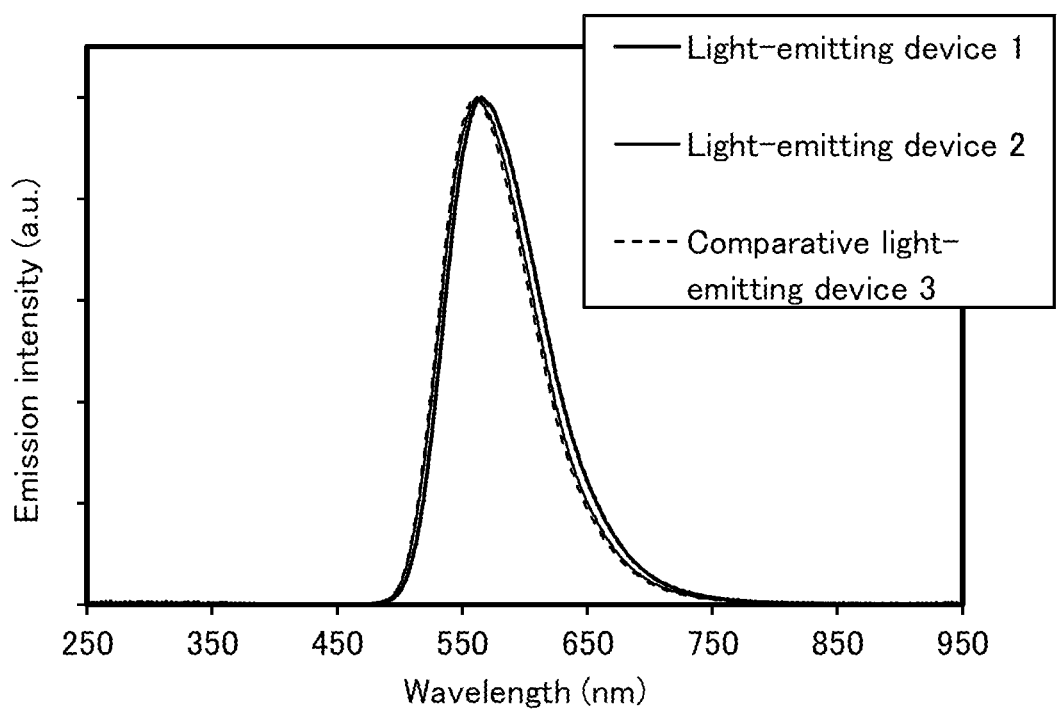
FIG. 19 is a graph showing the emission spectra of the light-emitting device 1, the light-emitting device 2, and the comparative light-emitting device 3.

FIG. 19 shows the emission spectra of the light-emitting devices to which current flows at a current density of 2.5 mA/cm$^2$. As shown in FIG. 19, the emission spectra of the light-emitting device 1, the light-emitting device 2, and the comparative light-emitting device 3 have peaks at around 561 nm, suggesting that each peak is derived from light emission of [Ir(ppy)$_2$(4dppy)] contained in the light-emitting layer 913.

Figure 20:
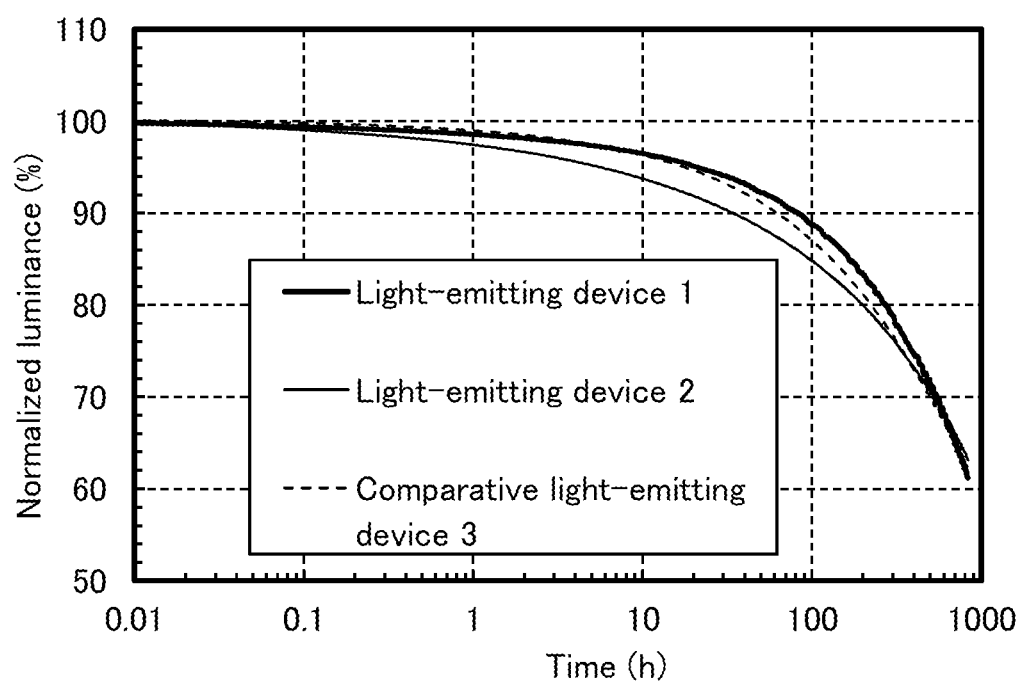
FIG. 20 is a graph showing the reliability of the light-emitting device 1, the light-emitting device 2, and the comparative light-emitting device 3.

Next, reliability tests were performed on each of the light-emitting devices. FIG. 20 shows the results of the reliability tests. In FIG. 20, the vertical axis represents normalized luminance (%) with an initial luminance of 100%, and the horizontal axis represents driving time (h) of the device. As the reliability tests, constant current driving tests where a constant current was supplied at a current density of 50 mA/cm$^2$ were performed.

Example 4

Fabricated in this example are a light-emitting device 4 as one embodiment of the present invention, which uses in a light-emitting layer 4Ph-8βN-2PCCzBfpm (Structural Formula (100)) described in Example 1 and [Ir(dmdppr-m5CP)$_2$(dpm)] as a guest material (a phosphorescent material), and a comparative light-emitting device 5 used for comparison, which uses in a light-emitting layer 9-phenyl-9'-(4-phenyl-2-quinazolinyl)-3,3'-bi-9H-carbazole (abbreviation: PCCzQz) and bis{4,6-dimethyl-2-[5-(5-cyano-2-methylphenyl)-3-(3,5-dimethylphenyl)-2-pyrazinyl-κN]phenyl-κC}(2,2,6,6-tetramethyl-3,5-heptanedionato-κ$^2$O,O') iridium(III) (abbreviation: [Ir(dmdppr-m5CP)$_2$(dpm)]) as a guest material (a phosphorescent material); and the measurement results of their characteristics are shown.

Note that the device structure of the light-emitting device 4 and the comparative light-emitting device 5 fabricated in this example is similar to that in FIG. 14 shown in Example 4, and the specific composition of each layer of the device structure is as shown in Table 3. Note that the electron-transport layer of the light-emitting device 4 and the comparative light-emitting device 5 has a stacked-layer structure of 2-[3'-(9,9-dimethyl-9H-fluoren-2-yl)-1,1'-biphenyl-3-yl]-4,6-diphenyl-1,3,5-triazine (abbreviation: mFBPTzn) and NBphen. Chemical formulae of materials used in this example are shown below.

TABLE 3

| | First electrode | Hole-injection layer | Hole-transport layer | Light-emitting layer | Electron-transport layer | Electron-injection layer | Second electrode |
|---|---|---|---|---|---|---|---|
| Light-emitting device 4 | ITSO (70 nm) | DBT3P-II:MoOx (2:1 75 nm) | PCBBiF (20 nm) | * | mFBPTzn (30 nm) NBphen (15 nm) | LiF (1 nm) | Al (200 nm) |
| Comparative light-emitting device 5 | ITSO (70 nm) | DBT3P-II:MoOx (2:1 75 nm) | PCBBiF (20 nm) | ** | mFBPTzn (30 nm) NBphen (15 nm) | LiF (1 nm) | Al (200 nm) |

* 4Ph-8βN-2PCCzBfpm:[Ir(ppy)$_2$(4dppy)] (1:0.1 40 nm)
** PCCzQz:[Ir(ppy)$_2$(4dppy)] (1:0.1 40 nm)

[Chemical Formula 24]

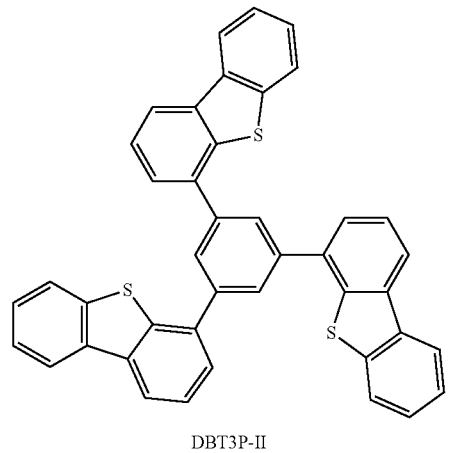

DBT3P-II

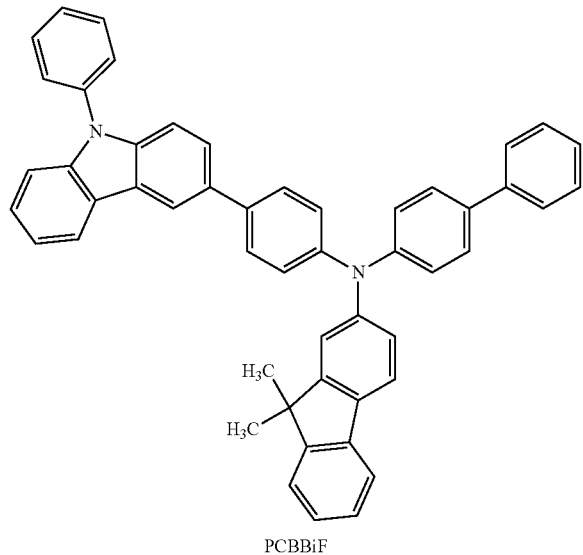

PCBBiF

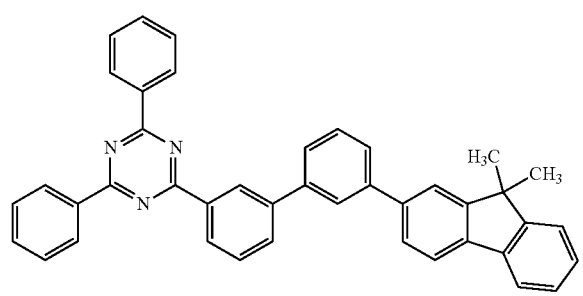

mFBPTzn

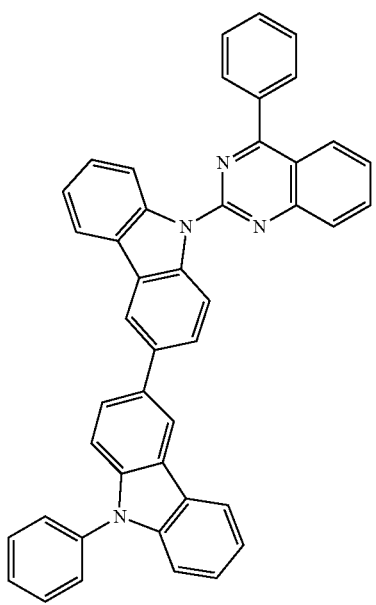

PCCzQz

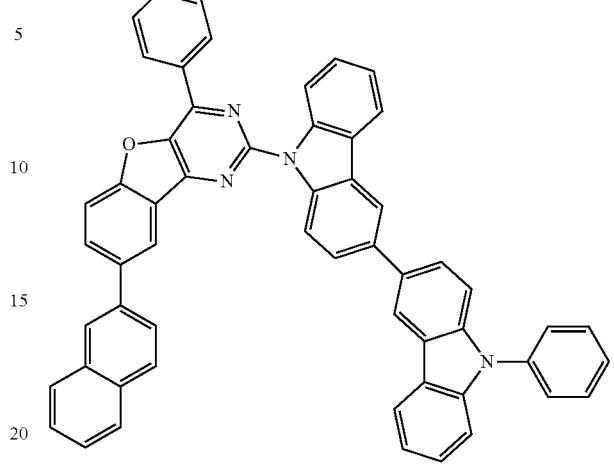

4Ph-8 β N-2PCCzBfpm (100)

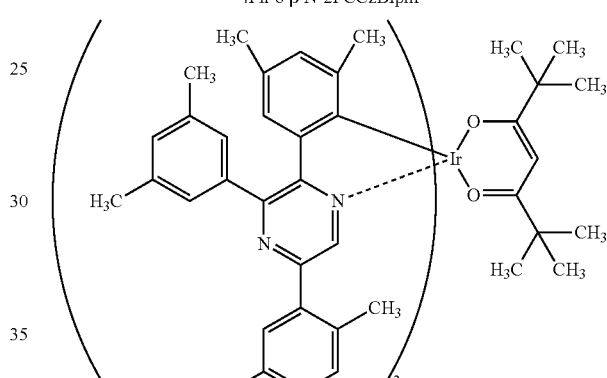

[Ir(dmdppr-m5CP)2(dpm)]

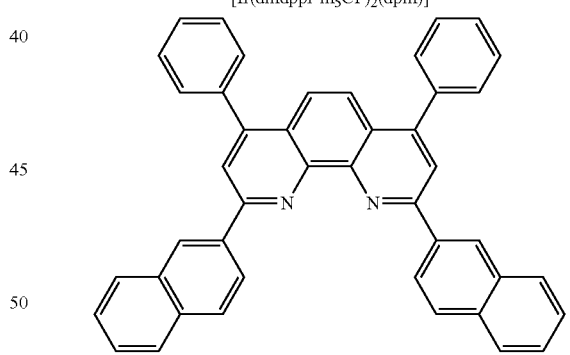

NBphen

<<Operation Characteristics of Light-Emitting Devices>>

Operation characteristics of the fabricated light-emitting device 4 and comparative light-emitting device 5 were measured. Note that the measurement was carried out at room temperature (in an atmosphere maintained at 25° C.).

Figure 21:
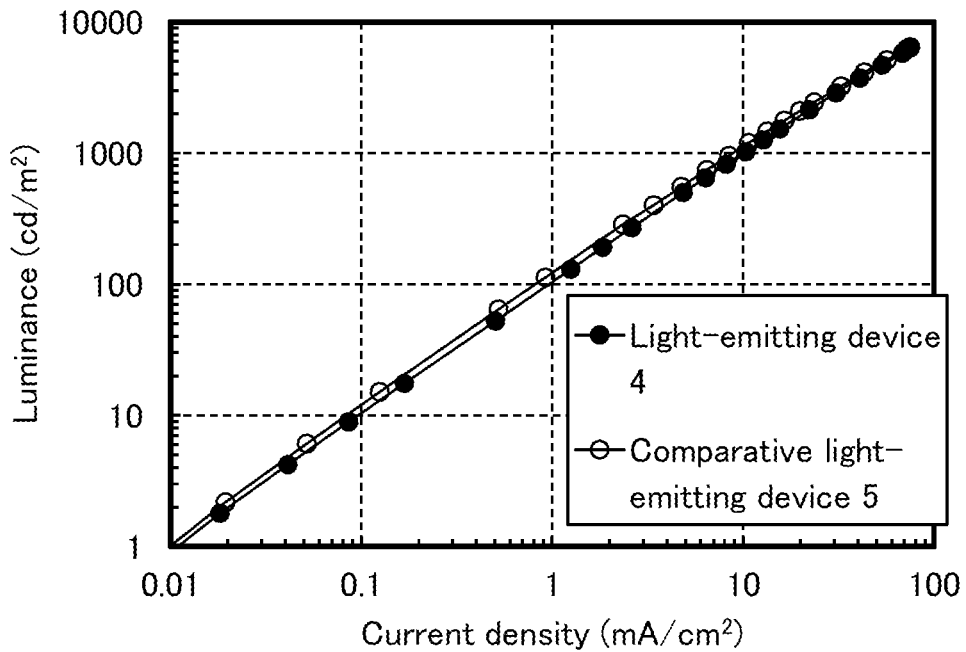
FIG. 21 is a graph showing the current density-luminance characteristics of a light-emitting device 4 and a comparative light-emitting device 5.
Figure 22:
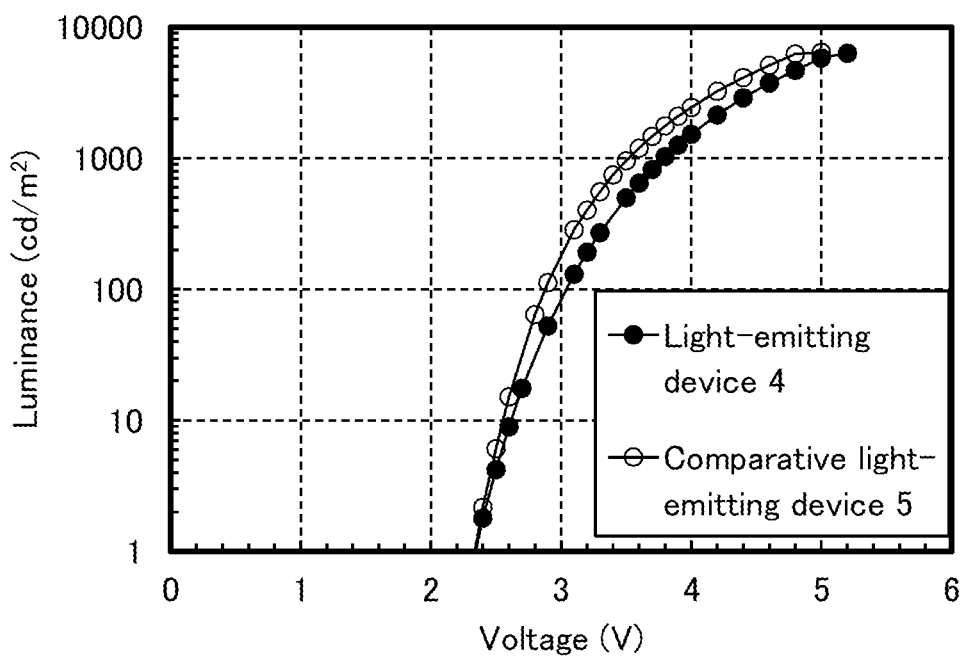
FIG. 22 is a graph showing the voltage-luminance characteristics of the light-emitting device 4 and the comparative light-emitting device 5.
Figure 23:
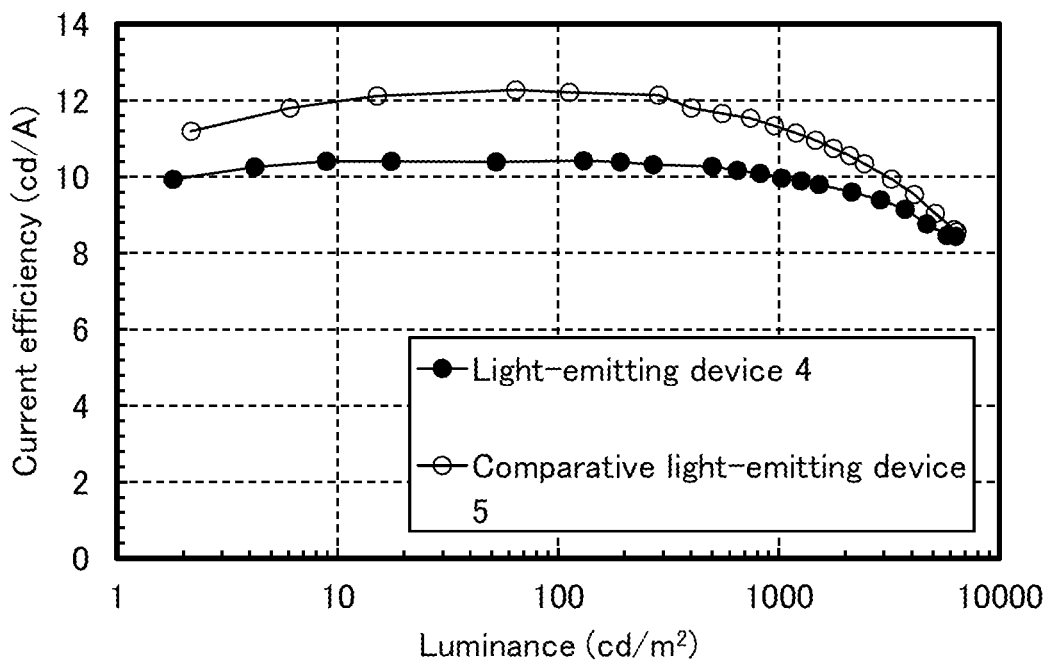
FIG. 23 is a graph showing the luminance-current efficiency characteristics of the light-emitting device 4 and the comparative light-emitting device 5.
Figure 24:
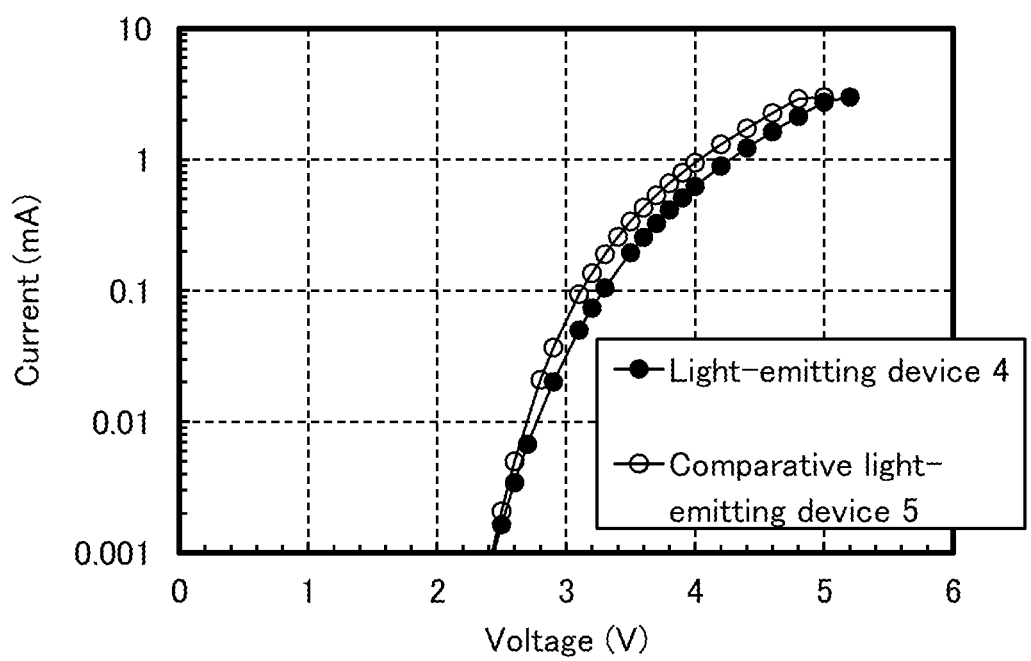
FIG. 24 is a graph showing the voltage-current characteristics of the light-emitting device 4 and the comparative light-emitting device 5.

The current density-luminance characteristics of each of the light-emitting devices are shown in FIG. 21, the voltage-luminance characteristics are shown in FIG. 22, the luminance-current efficiency characteristics are shown in FIG. 23, and the voltage-current characteristics are shown in FIG. 24.

Table 4 below shows the initial values of the main characteristics of each of the light-emitting devices at around 1000 cd/m$^2$.

TABLE 4

|  | Voltage (V) | Current (mA) | Current density (mA/cm$^2$) | Chromaticity (x, y) | Luminance (cd/m$^2$) | Current efficiency (cd/A) | Power efficiency (lm/W) | External quantum efficiency (%) |
|---|---|---|---|---|---|---|---|---|
| Light-emitting device 4 | 3.8 | 0.41 | 10 | (0.71, 0.29) | 1000 | 10 | 8.2 | 23.0 |
| Comparative light-emitting device 5 | 3.5 | 0.3 | 8.4 | (0.71, 0.29) | 960 | 11 | 10 | 24 |

Figure 25:
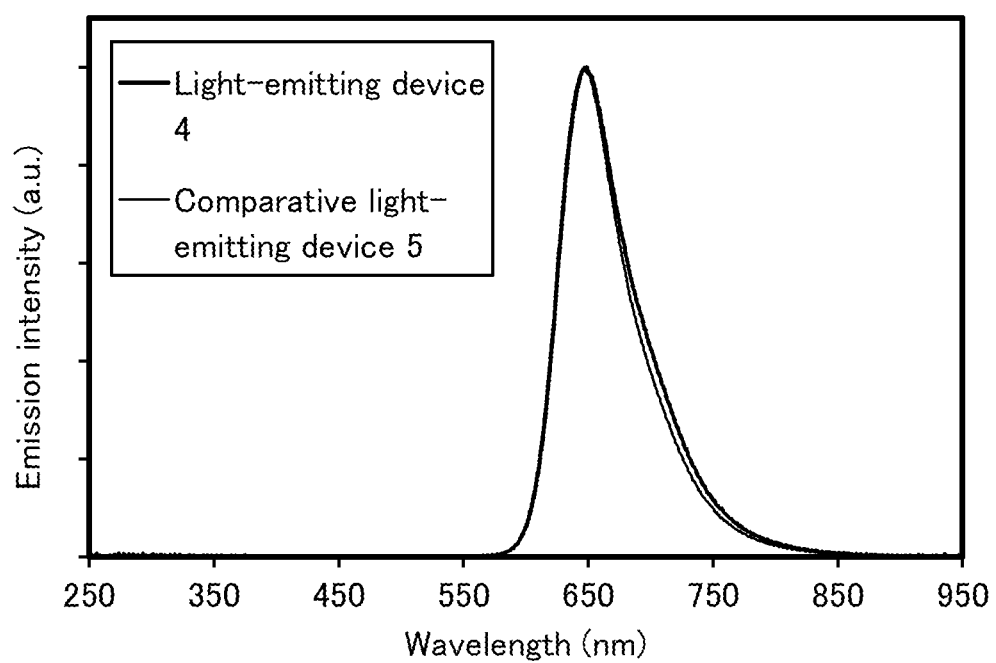
FIG. 25 is a graph showing the emission spectra of the light-emitting device 4 and the comparative light-emitting device 5.

FIG. 25 shows the emission spectra of the light-emitting devices to which current flows at a current density of 2.5 mA/cm$^2$. As shown in FIG. 25, the emission spectra of the light-emitting devices have peaks at around 647 nm, suggesting that each peak is derived from light emission of [Ir(dmdppr-m5CP)$_2$(dpm)] contained in the light-emitting layer 913.

Figure 26:
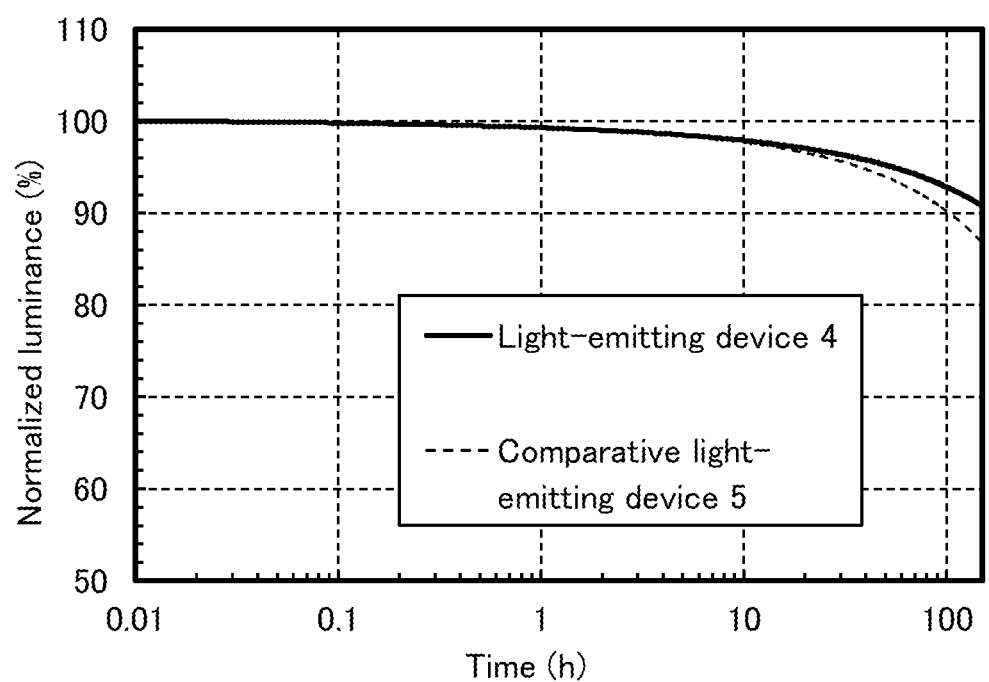
FIG. 26 is a graph showing the reliability of the light-emitting device 4 and the comparative light-emitting device 5.

Next, reliability tests were performed on each of the light-emitting devices. FIG. 26 shows the results of the reliability tests. In FIG. 26, the vertical axis represents normalized luminance (%) with an initial luminance of 100%, and the horizontal axis represents driving time (h) of the device. As the reliability tests, constant current driving tests where a constant current was supplied at a current density of 75 mA/cm$^2$ were performed.

REFERENCE NUMERALS

101: first electrode, 102: second electrode, 103: EL layer, 103a, 103b: EL layer, 104: charge-generation layer, 111, 111a, 111b: hole-injection layer, 112, 112a, 112b: hole-transport layer, 113, 113a, 113b: light-emitting layer, 114, 114a, 114b: electron-transport layer, 115, 115a, 115b: electron-injection layer, 200R, 200G, 200B: optical path length, 201: first substrate, 202: transistor (FET), 203R, 203G, 203B, 203W: light-emitting device, 204: EL layer, 205: second substrate, 206R, 206G, 206B: color filter, 206R', 206G', 206B': color filter, 207: first electrode, 208: second electrode, 209: black layer (black matrix), 210R, 210G: conductive layer, 301: first substrate, 302: pixel portion, 303: driver circuit portion (source line driver circuit), 304a, 304b: driver circuit portion (gate line driver circuit), 305: sealant, 306: second substrate, 307: lead wiring, 308: FPC, 309: FET, 310: FET, 311: FET, 312: FET, 313: first electrode, 314: insulator, 315: EL layer, 316: second electrode, 317: light-emitting device, 318: space, 900: substrate, 901: first electrode, 902: EL layer, 903: second electrode, 911: hole-injection layer, 912: hole-transport layer, 913: light-emitting layer, 914: electron-transport layer, 915: electron-injection layer, 4000: lighting device, 4001: substrate, 4002: light-emitting device, 4003: substrate, 4004: first electrode, 4005: EL layer, 4006: second electrode, 4007: electrode, 4008: electrode, 4009: auxiliary wiring, 4010: insulating layer, 4011: sealing substrate, 4012: sealant, 4013: desiccant, 4200: lighting device, 4201: substrate, 4202: light-emitting device, 4204: first electrode, 4205: EL layer, 4206: second electrode, 4207: electrode, 4208: electrode, 4209: auxiliary wiring, 4210: insulating layer, 4211: sealing substrate, 4212: sealant, 4213: barrier film, 4214: planarization film, 5101: light, 5102: wheel, 5103: door, 5104: display portion, 5105: steering wheel, 5106: shifter, 5107: seat, 5108: inner rearview mirror, 5109: part of glass window, 7000: housing, 7001: display portion, 7002: second display portion, 7003: speaker, 7004: LED lamp, 7005: operation key, 7006: connection terminal, 7007: sensor, 7008: microphone, 7009: switch, 7010: infrared port, 7011: recording medium reading portion, 7014: antenna, 7015: shutter button, 7016: image receiving portion, 7018: stand, 7022, 7023: operation button, 7024: connection terminal, 7025: band, 7026: microphone, 7029: sensor, 7030: speaker, 7052, 7053, 7054: information, 9310: portable information terminal, 9311: display portion, 9312: display region, 9313: hinge, 9315: housing This application is based on Japanese Patent Application Serial No. 2019-076333 filed on Apr. 12, 2019, the entire contents of which are hereby incorporated herein by reference.

The invention claimed is:

1. An organic compound represented by Formula (G1):

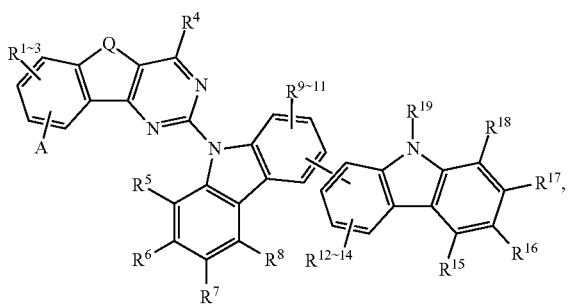

(G1)

wherein Q represents oxygen, wherein A represents a naphthyl ring, and wherein each of $R^1$ to $R^{19}$ independently represents any one of hydrogen, an alkyl group having 1 to 6 carbon atoms, a substituted or unsubstituted cycloalkyl group having 3 to 7 carbon atoms in a ring, and a substituted or unsubstituted aryl group having 6 to 13 carbon atoms in a ring.

2. The organic compound according to claim 1, wherein the organic compound is represented by Formula (G2):

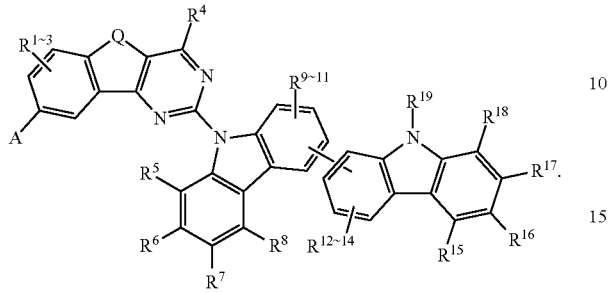

3. The organic compound according to claim 1, wherein the organic compound is represented by Formula (G2):

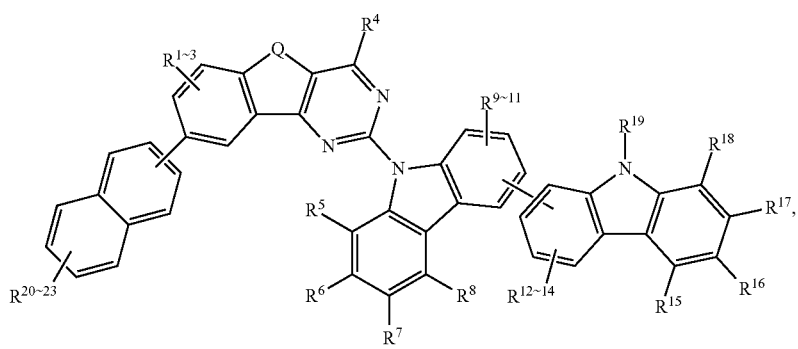

and
wherein each of $R^{20}$ to $R^{23}$ independently represents any one of hydrogen, an alkyl group having 1 to 6 carbon atoms, a substituted or unsubstituted cycloalkyl group having 3 to 7 carbon atoms in a ring, and a substituted or unsubstituted aryl group having 6 to 13 carbon atoms in a ring.

4. The organic compound according to claim 1, wherein the organic compound is represented by Formula (100):

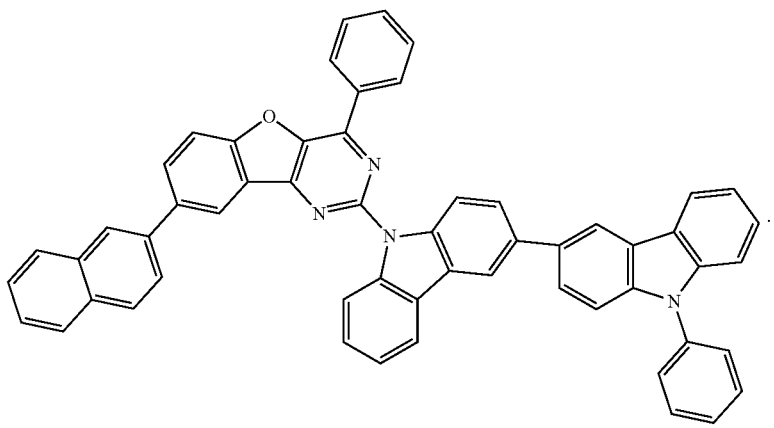

5. A light-emitting device comprising:
the organic compound according to claim 1.

6. A light-emitting device comprising:
an EL layer between a pair of electrodes,
wherein the EL layer comprises the organic compound according to claim 1.

7. A light-emitting device comprising:
a first electrode;
a light-emitting layer over the first electrode, the light-emitting layer comprising the organic compound according to claim 1; and
a second electrode over the light-emitting layer.

8. A light-emitting apparatus comprising:
the light-emitting device according to claim 7; and
at least one of a transistor and a substrate.

9. An electronic device comprising:
the light-emitting apparatus according to claim 8; and
at least one of a microphone, a camera, an operation button, an external connection portion, and a speaker.

10. A lighting device comprising:
the light-emitting device according to claim 7; and
at least one of a housing, a cover, and a support.

* * * * *